United States Patent [19]

Kitamura et al.

[11] Patent Number: 5,167,863
[45] Date of Patent: Dec. 1, 1992

[54] OPTICALLY ACTIVE COMPOUND, LIQUID CRYSTAL COMPOSITION CONTAINING SAID COMPOUND, AND LIQUID CRYSTAL OPTICAL MODULATOR USING SAID COMPOSITION

[75] Inventors: Teruo Kitamura; Katsumi Kondo, both of Katsuta; Akio Mukoh, Mito; Koichi Matsumura, Ibaraki; Mitsuru Kawada, Amagasaki; Yoshihiro Sugihara, Toyonaka, all of Japan

[73] Assignees: Hitachi, Ltd., Tokyo; Takeda Chemical Industries, Ltd., Osaka, both of Japan

[21] Appl. No.: 552,494

[22] Filed: Jul. 16, 1990

Related U.S. Application Data

[63] Continuation of Ser. No. 287,282, Dec. 21, 1988, abandoned.

[30] Foreign Application Priority Data

Dec. 24, 1987 [JP] Japan .................. 62-325464
Apr. 1, 1988 [JP] Japan .................. 63-78039

[51] Int. Cl.⁵ .............. C09K 19/12; C07C 69/76; C07C 69/00
[52] U.S. Cl. .............. 252/299.65; 252/299.66; 252/299.63; 252/299.61; 560/59; 560/60; 560/73; 560/102; 560/108; 560/109; 560/141
[58] Field of Search ............ 252/299.65, 299.64, 252/299.66; 560/73, 59, 60, 141, 102, 108, 109

[56] References Cited

U.S. PATENT DOCUMENTS 4,650,600  3/1987  Heppke et al. ............. 252/299.65

FOREIGN PATENT DOCUMENTS 3333677   9/1983   Fed. Rep. of Germany .
3534777   9/1985   Fed. Rep. of Germany .
3604899   2/1986   Fed. Rep. of Germany .
60-218358 11/1985   Japan .
61-68449  4/1986   Japan .

OTHER PUBLICATIONS

Patent Abstracts of Japan, vol. 13, No. 151.
Patent Abstracts of Japan, vol. 13, No. 278.

Primary Examiner—Robert L. Stoll
Assistant Examiner—Philip Tucker
Attorney, Agent, or Firm—Antonelli, Terry, Stout & Kraus

[57] ABSTRACT

There are disclosed an optically active compound represented by the general formula:

$$R_1-Q_1-M-Q_2-\overset{*}{C}H-(CH_2)_n-\overset{*}{C}H-Q_3-R_4$$
$$\phantom{R_1-Q_1-M-Q_2-}\underset{R_2}{|}\phantom{-(CH_2)_n-}\underset{R_3}{|}$$

wherein $n$, $R_1$, $R_2$, $R_3$, $R_4$, $Q_1$, $Q_2$, $Q_3$, and $M$ are defined as in the detailed explanation, and *-marked carbon atoms are each an asymmetric carbon atom; a liquid crystal composition comprising at least one optically active compound of said general formula and a liquid crystal optical modulator using the composition thereof.

13 Claims, 1 Drawing Sheet

OPTICALLY ACTIVE COMPOUND, LIQUID CRYSTAL COMPOSITION CONTAINING SAID COMPOUND, AND LIQUID CRYSTAL OPTICAL MODULATOR USING SAID COMPOSITION

This is a continuation of application Ser. No. 07/287,282, filed Dec. 21, 1988 now abandoned.

BACKGROUND OF THE INVENTION

1. Field of the Invention

The present invention relates to an optically active compound and a liquid crystal composition containing said compound The compound and composition containing said compound, of the present invention show a ferroelectric liquid crystal phase, and accordingly are useful as an electrooptic switching element such as liquid crystal display device or the like and can be used in liquid crystal optical modulators.

2. Discussion on the Related Arts

Liquid crystal display devices have various excellent features such as low-voltage operability, low power consumption, being thin and light-weight, and easy on the eye to be a light-receiving type. Accordingly, they are in wide use as various display devices.

Liquid crystal display devices using a nematic liquid crystal called a twisted nematic mode (TN mode) are in use currently. However, display devices using this nematic liquid crystal have had a drawback of being very slow in response as compared to luminescent type display devices such as CRT, EL and the like. Consequently, when such display devices are applied in a display device, particularly a large scale display device capable of displaying a large amount of information, it is impossible to obtain a display of good contrast. Thus, the liquid crystal display devices using a nematic liquid crystal have had a limitation for wide applications. There has recently been developed a liquid crystal device using a nematic liquid crystal called a super twisted nematic type (STN mode) or SBE and capable of giving a display of improved contrast. Even in this STN type liquid crystal display device, however, the response is not sufficient and therefore said device finds a limitation in application to a display capable of displaying a still larger amount of information. Hence, various attempts are under way to develop a new liquid crystal display system giving an excellent response.

Ferroelectric liquid crystals have a memory function and give a high speed response, and accordingly their application to a large scale display is highly expected. As liquid crystals having ferroelectric properties, there are known those showing a chiral smectic C phase, a chiral smectic H phase, a chiral smectic J phase, etc. Of these ferroelectric liquid crystals, those showing a chiral smectic C phase are thought to have highest practical usability.

Ferroelectric liquid crystals showing a chiral smectic C phase were first synthesized in 1975 by R. B. Meyer et al., and their typical examples include 2-methylbutyl 4-(4'-n-decyloxybenzylideneamino)cinnamate (hereinafter abbreviated to DOBAMBC) [J. Physique, 36, L-69 (1975)].

A thin film liquid crystal cell was prepared response of μ sec order [N. A. Clark et al., Appl. Phys. Lett., 36, 89 (1980)]. Since that time, there was started the development of optical modulation devices (e.g. liquid crystal device, photo-printer head) using a ferroelectric liquid crystal showing a chiral smectic C phase (hereinafter may be referred to simply as "ferroelectric liquid crystal").

As a result, a number of ferroelectric liquid crystal compounds showing a chiral smectic C phase have been developed since then and various ferroelectric liquid crystal compounds are known currently. However, no ferroelectric liquid crystal compound is found yet which has satisfactory reliability and capability for use in a display device, particularly a large scale one, etc.

In order for a ferroelectric liquid crystal to be practically used as a liquid crystal display device, etc., the liquid crystal must be superior in high speed response, orientation, memory function, threshold, temperature dependences of these properties, etc. Also, the ferroelectric liquid crystal is required to show a chiral smectic C phase over a wide temperature range so that it can operate at a sufficiently wide temperature range including room temperature and further to have excellent physical and chemical stabilities.

In order for a ferroelectric liquid crystal to have, in particular, excellent physical and chemical stabilities, good high speed response and good memory function, the liquid crystal must have a large spontaneous polarization.

Among the so far developed ferroelectric liquid crystal, no compound is found yet which satisfies the above requirements. For example, the above mentioned DOBAMBC, being a liquid crystal of Schiff's base type, is insufficient in chemical stability to water, light, etc. and moreover, has a small spontaneous polarization of 4 $nC/cm^2$ or below.

Ester type liquid crystals are reported as a ferroelectric liquid crystal which is chemically stable. However, these liquid crystals are not satisfactory because they have no sufficiently large spontaneous polarization and no sufficiently wide temperature range of chiral smectic C phase.

In order to obtain a large spontaneous polarization, there were synthesized those compounds having two asymmetric carbon atoms as an optically active group essential for the expression of chiral smectic C phase.

These compounds include, for example, liquid crystal compounds having a dichiral epoxide side chain [David M. Walba et al., Journal of American Chemical Society, 108, 7424 (1986)] and liquid crystal compounds having a halogen atom and a methyl group on two adjacent asymmetric carbon atoms [Japanese Patent Application Kokai (Laid-Open) Nos. 168780/1985, 218358/1985, 68449/1986, 40/1987, 46/1987, 103043/1987, 111950/1987, 142131/1987, 175443/1987, etc.].

As a typical example of the above liquid crystal compounds, there is (s)-3-methyl-2-chlorobutyl 4-(4'-octylcarbonyloxy) biphenylcarboxylate [Japanese Patent Application Kokai (Laid-Open) No. 68449/1986]. This liquid crystal compound has a very large spontaneous polarization of 180 $nC/cm^2$ but, being an aliphatic chloro compound, has poor chemical stability. Hence, there was synthesized 4'-octylcarbonyloxy-4-[(s)-2-methoxy-(s)-3-methylpentyloxycarbonyl]biphenyl [Japanese Patent Application Kokai (Laid-Open) No. 228036/1987]. This compound has excellent chemical stability but has an insufficient spontaneous polarization of 17 $nC/cm^2$.

SUMMARY OF THE INVENTION

The present inventors made study in order to find out a ferroelectric liquid crystal compound having excellent physical and chemical stabilities and a large spontaneous polarization and, as a result, have completed the present invention. That is, the present inventors made study on liquid crystal compounds obtained by combining a chemically stable ester compound with an optically active group having two asymmetric carbon atoms and, as a result, have completed the present invention.

Specifically, the present invention has been achieved by using, as an optically active group having two asymmetric carbon atoms, a structure containing no halogen-carbon bond which is contained in conventional liquid crystal compounds and gives poor chemical stability and bonding said structure to (a) a six-membered ring (e.g. benzene) constituting the skeleton of a liquid crystal compound to be synthesized and also to (b) an alkyl group constituting one terminal group of said liquid crystal compound, in a particular pattern.

DETAILED DISCUSSION OF PREFERRED EMBODIMENTS

Figure 1:
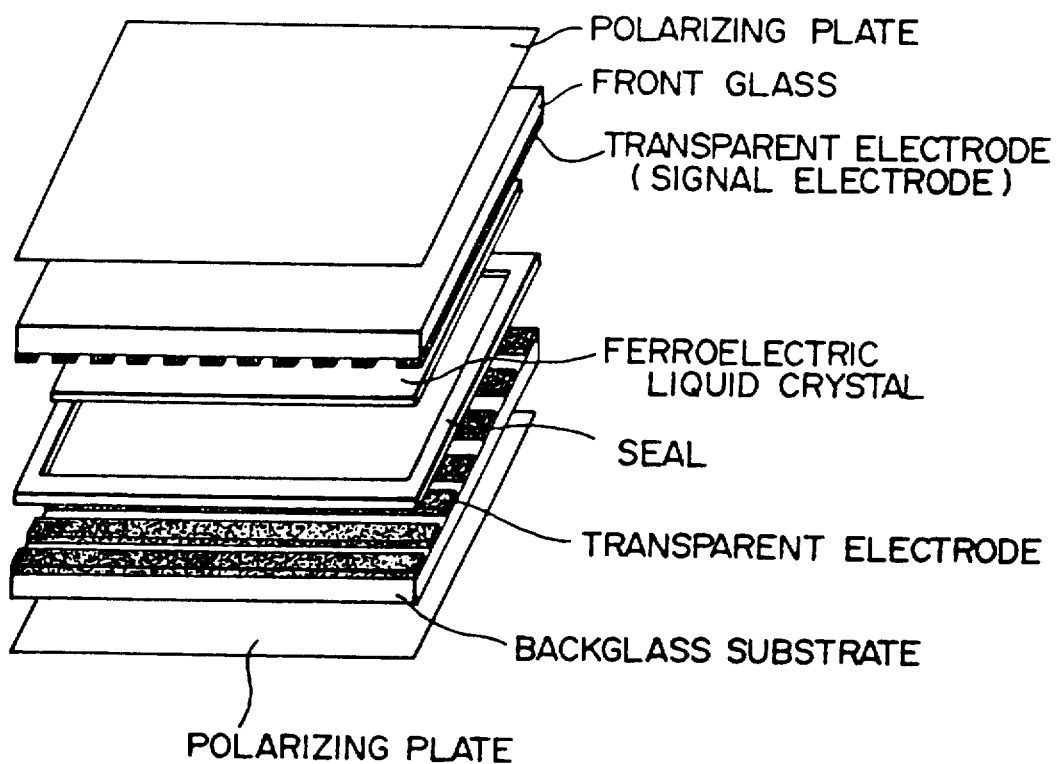
FIG. 1 is a schematic illustration of an example of the liquid crystal display device using the liquid crystal composition of the present invention.

The first aspect of the present invention is directed to an optically active compound represented by the general formula [I]:

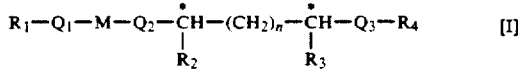

[I]

wherein n is 0 or 1 (when n is 0, —$(CH_2)_n$— is a single bond), $R_1$ is an alkyl group of 3–14 carbon atoms, $R_2$ and $R_3$ are independently a lower alkyl group of 1–3 carbon atoms, $R_4$ is an alkyl group of 1–10 carbon atoms, $Q_1$, $Q_2$ and $Q_3$ are independently a single bond, an ether bond, a carboxylic acid ester bond, a carbonyl or a carbonyldioxy bond, M is

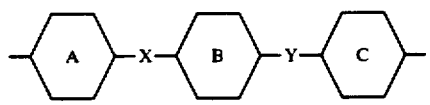

or

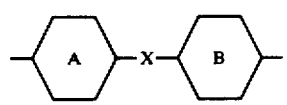

(X and Y are independently a single bond, a carboxylic acid ester bond, a methyleneoxy bond or an ethylene bond, and

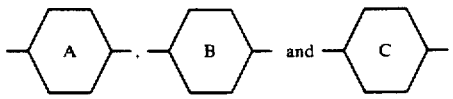

are independently a homocyclic or heterocyclic six-membered ring-1,4-diyl group which may contain 1-2 oxygen or nitrogen atoms as a ring-forming atom), and *-marked carbon atoms are each an asymmetric carbon atom.

The second aspect of the present invention is directed to a liquid crystal composition comprising at least one optically active compound represented by the general formula [I].

The third aspect of the present invention is directed to a liquid crystal optical modulator using a liquid crystal composition of the above second aspect.

The compound [I] according to the present invention can be classified into the following compounds [I'] and [I"] depending upon the basic skeleton M.

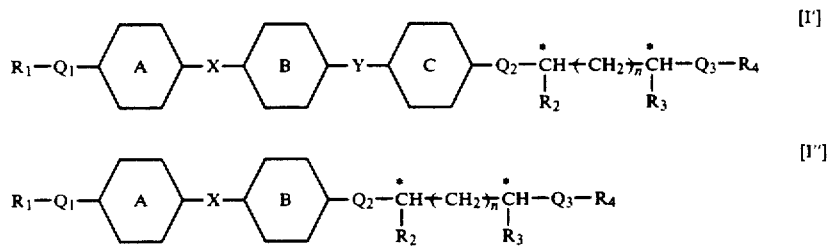

In the above compounds [I], [I'] and [I"], the alkyl group of 3–14 carbon atoms represented by $R_1$ can be of straight chain or branched chain. Specifically, there can be mentioned straight alkyl chain such as propyl, butyl, pentyl, hexyl, heptyl, octyl, nonyl, decyl, undecyl, dodecyl, tridecyl, tetradecyl and the like, as well as branched alkyl chain such as isopropyl, isobutyl, sec-butyl, tert-butyl, isopentyl, neopentyl, tert-pentyl, isohexyl, 1-methylpentyl, 2-methylpentyl, 5-methylhexyl, 2,3,5-trimethylhexyl, 2,7,8-trimethyldecyl, 4-ethyl-5-methylnonyl and the like. Of these, preferable are straight alkyl chain of 6–12 carbon atoms such as hexyl, heptyl, octyl, decyl, undecyl, dodecyl and the like. As the lower alkyl groups of 1–3 carbon atoms represented by $R_2$ and $R_3$, there can be mentioned straight alkyl chain or branched alkyl chain such as methyl, ethyl, propyl and isopropyl. Of these, methyl is preferable. The alkyl group of 1–10 carbon atoms represented by $R_4$ can be of straight chain or branched chain. Specifically, there can be mentioned straight alkyl chain such as methyl, ethyl, propyl, butyl, pentyl, hexyl, heptyl, octyl, nonyl, decyl and the like, as well as branched alkyl chain such as isopropyl, isobutyl, sec-butyl, tert-butyl, isopentyl, neopentyl, tert-pentyl, isohexyl, 1-methylpentyl, 2-methylpentyl, 5-methylhexyl, 4-ethylhexyl, 2,3,5-trimethylhexyl, 4-ethyl-5-methylhexyl and the like. Of these, preferable are straight alkyl chain of 1–8 carbon atoms such as methyl, ethyl, propyl, butyl, pentyl, heptyl and octyl.

It is generally preferable that $Q_1$ be a single bond, an ether bond or a carboxylic acid ester bond and $Q_2$ and $Q_3$ be independently an ether bond or a carboxylic acid ester bond. As the carboxylic acid ester bond represented by $Q_1$, $Q_2$ and $Q_3$, there can be mentioned a

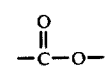

ester bond or a

ester bond.

As the preferable bonds of $Q_1$, $Q_2$ and $Q_3$, there can be mentioned a single bond, an ether bond or

ester bond for $Q_1$, a

ester bond, a

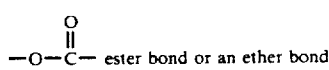

for $Q_2$ and an ether bond, 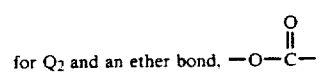

ester bond or an ether bond for $Q_2$ and an ether bond,

ester bond for $Q_3$.

As the carboxylic acid ester bond represented by X and Y, there can be mentioned a

ester bond and a

ester bond; and as the ethyleneoxy bond represented by X and Y, there can be mentioned —CH$_2$O— and —OCH$_2$—.

The six-membered ring-1,4-diyl group represented by

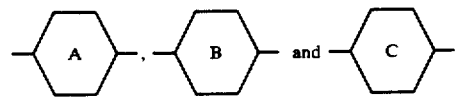

refers to a benzene ring having two bonds at the para-positions. As specific examples of such a group, there can be mentioned, for example, p-phenylene, 1,4-cyclohexylene, 2,5-(1,3-dioxane)diyl, 2,5-pyridinediyl, 2,5pyrimidinediyl, 2,5-(1,4-pyrazine)diyl and 3,6-(1,2-pyridazine)diyl. These rings can be substituted with a halogen, cyano, methyl and methoxy group.

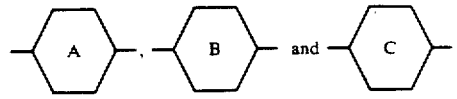

may be the same or different. 2,5-(1,3-dioxane)diyl can be

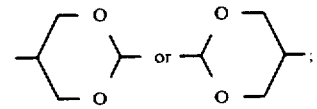

2,5-pyridinediyl can be

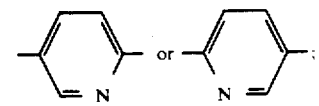

and 2,5-pyrimidinediyl can be

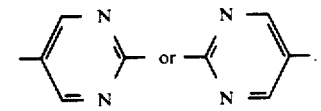

When M is

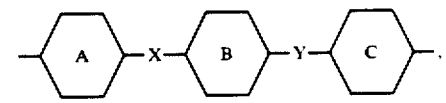

preferable combinations of A, B, C, X and Y include a case that one of X and Y is a single bond, the other of them is a carboxylic acid ester bond, and all of

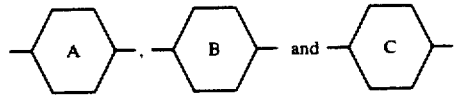

are p-phenylene or at least one of them is 2,5-pyrimidinediyl. When M is

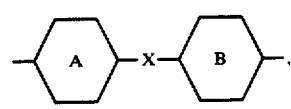

preferable combinations of A, B and X include a case that X is a single bond or a carboxylic acid ester bond and both of

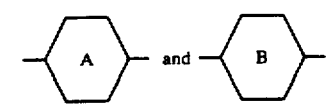

are p-phenylene or either of them is 2,5-pyrimidinediyl.

The compound [I] has two asymmetric carbon atoms within the molecule and therefore has four different optical isomers, that is, (R,R) type, (R,S) type, (S,R) type and (S,S) type.

The optically active compound [I] of the present invention has a structure in which each asymmetric carbon atom is bonded to oxygen or carbonyl, and therefore the compound generally shows high spontaneous polarization. In addition, most of the compounds [I] show a chiral smectic C (Sc*) phase which is a liquid crystal phase suitable for a display method utilizing the ferroelectric property of liquid crystal, and the temperature range of the chiral smectic C phase is low and wide.

The optically active compound of the present invention is very stable to heat, light, water and air. Accordingly, in putting the compound to practical use as a liquid crystal material, there can be eliminated inconveniences such as arrangements of an apparatus for prevention of overheating, a glass frit seal for prevention of moisture absorption or permeation, etc.

The optically active compound [I] of the present invention has excellent conformability with conventionally known liquid crystal compounds such as Schiff's base type, biphenyl type, henylcyclohexane type, heterocyclic type and the like. Therefore, the compound can be made into a liquid crystal composition having excellent properties, by incorporating it into said liquid crystal compounds.

As the liquid crystal compounds into which the optically active compound [I] of the present invention can be incorporated, there can be mentioned, for example, ferroelectric liquid crystal compounds as well as liquid crystal compounds showing a smectic C phase. The ferroelectric liquid crystal compounds include, for example, biphenyl type liquid crystals described in Japanese Patent Application Kokai (Laid-Open) Nos. 118744/1984 and 13729/1985, ester type liquid crystals described in Japanese Patent Application Kokai (Laid-Open) Nos. 128357/1984, 51147/1985, 22051/1986 and 249953/1986, and pyrimidine type liquid crystals described in Japanese Patent Application Kokai (Laid-Open) Nos. 260564/1985, 24756/1986, 85368/1986 and 215373/1986. The liquid crystal compounds showing a smectic C phase include, for example, ester type liquid crystal compounds described in Japanese Patent Application Kokai (Laid-Open) No. 228036/1987, and cyclohexane type liquid crystals and heterocyclic type liquid crystals described in the materials of the 16th Friburg Liquid Crystal Forum (Mar. 21, 1986) and the materials of the First International Symposium on ferroelectric Liquid Crystals (Sept. 21, 1987).

The ferroelectric liquid crystal compound of the present invention can also be incorporated into the nematic or cholesteric liquid crystals described in "Flüssige Kristalle in Tabellen" I & II VEB Verlag, Leipzig and further can be mixed with any of commercially available nematic liquid crystal compounds. When the ferroelectric liquid crystal compound of the present invention is incorporated into nematic liquid crystals, the chirality of the present compound is effectively utilized and its addition amount can freely control the twisting direction of cholesteric pitch and length of pitch of the nematic liquid crystal composition obtained.

The liquid crystal display device according to the present invention can be produced from the above mentioned liquid crystal composition of the present invention according to a conventional process. The present composition can be used in, for example, a liquid crystal display device having a structure as shown in FIG. 1. The device can be obtained as a guest host type display device by the use of a dichroic dye.

The optically active compound [I] of the present invention can be produced according to the following process.

Process 1

[Case in the general formula [I], the bond $Q_2$ between the skeletal component and the dichiral side chain component is a

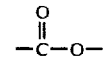

bond] (scheme 1)

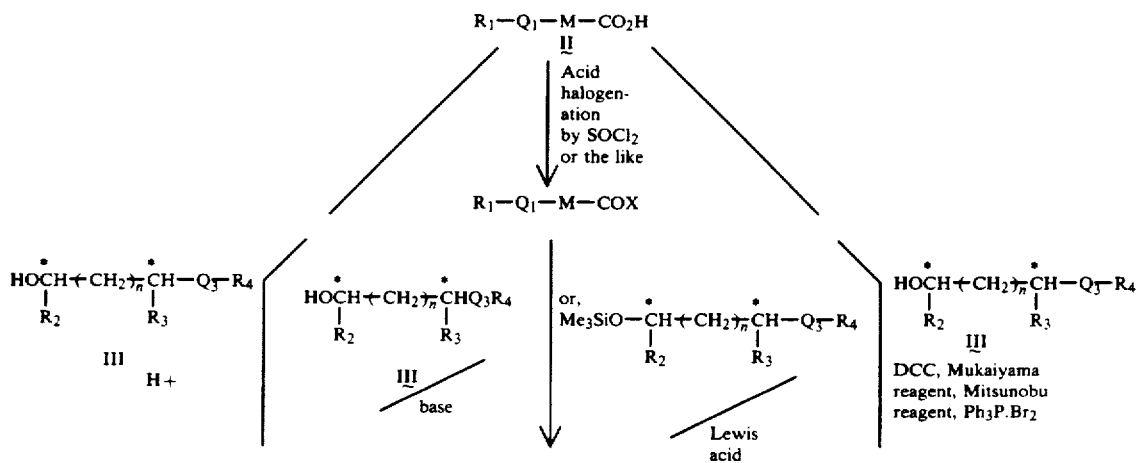

-continued
Scheme 1

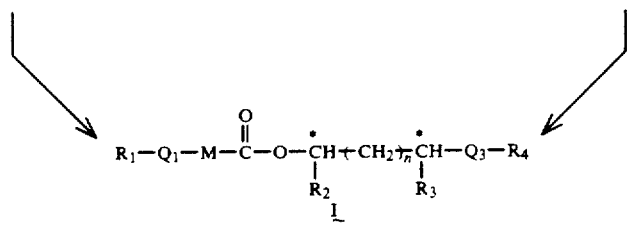

In the scheme 1, n, $R_1$, $R_2$, $R_3$, $R_4$, $Q_1$, $Q_3$, M and * mark have the same definitions as given previously, and X is a halogen atom.

As shown in the scheme 1, a compound [I] can be obtained from a carboxylic acid [II] as the basic skeleton of the compound [I] and an optically active dichiral secondary alcohol [III]. This condensation reaction can be carried out according to a known conventional method. That is, the basic skeletal carboxylic acid [II] and the optically active dichiral secondary alcohol [III] are subjected to a dehydration and condensation reaction in an organic solvent in the presence of a proton acid to produce the compound [I]. As the proton acid, there can be used, for example, inorganic acids such as sulfuric acid, hydrochloric acid, perchloric acid and the like, organic sulfonic acids such as p-toluenesulfonic acid, benzenesulfonic acid, trifluoromethanesulfonic acid, methanesulfonic acid and the like, and strongly acidic ion exchange resins such as Amberlist ® and the like. As the organic solvent used in this condensation reaction, there can be mentioned, for example, hydrocarbons such as hexane, benzene, toluene and the like, halogenated hydrocarbons such as chloroform, methylene chloride, carbon tetrachloride, 1,2-dichloroethane and the like, ethers such as diethyl ether, tetrahydrofuran, dioxane and the like, ethyl acetate, acetonitrile and dimethylformamide.

The desired optically active compound [I] thus produced can be isolated from the reaction mixture and purified by an ordinary separation and purification procedures (e.g. extraction, solvent operation, column chromatography, liquid chromatography, recrystallization, fractional crystallization).

The desired optically active compound [I] can also be obtained in a pure form by converting the basic skeletal carboxylic acid [II] into a corresponding acid halide with thionyl chloride, thionyl bromide or the like, subjecting the acid halide and an optically active dichiral secondary alcohol [III] to an esterification reaction in an appropriate organic solvent in the presence of an organic base (e.g. pyridine, triethylamine) at a low temperature, room temperature or an elevated temperature for few to several hours, optionally few to several days, and carrying out an ordinary separation and purification procedures.

The condensation reaction of the scheme 1 can also be carried out by appropriately selecting a known condensation method other than mentioned above, such as (a) a method using an activating reagent [e.g. N,N'-dicyclohexylcarbodiimide (DCC)*[1], Mukaiyama reagent *[2] represented by 1-methyl-2-halopyridinium iodide, diethyl azodicarboxylate DEAD and triphenylphosphite (Ph₃P) (Mitsunobu's reagent)*[3], triphenylphosphine dibromide*[4] or (b) a method*[5] comprising in converting the skeletal carboxylic acid [II] into a corresponding acid halide with thionyl chloride or thionyl bromide or the like and then condensing the acid halide with an trimethylsilyl ether of an optically active dichiral secondary alcohol [III] in the presence of a catalytic amount of a Lewis acid (e.g. zinc chloride).

Process 2

[Case in the general formula [I], the bond $Q_2$ between the skeletal component and the dichiral side chain component is an ether (—O—) bond] (scheme 2)

Scheme 2

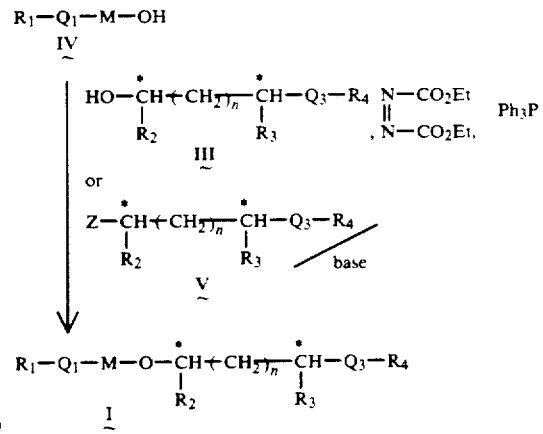

In the above scheme 2, n, $R_1$, $R_2$, $R_3$, $R_4$, $Q_1$, $Q_3$, M and * mark have the same definitions as given previously. In the formula V, Z is a halogen atom, an organic sulfonyloxy group or the like.

The compound [I] can also be obtained by a known condensation reaction between a basic skeletal alcohol or phenolic hydroxy compound [IV] and an optically active dichiral secondary alcohol [III]. For example, the compound [I] can be obtained by a condensation reaction*[6] using the above mentioned diethyl azodicarboxylate (DEAD) and triphenylphosphine (Ph₃P), or by reacting a dichiral secondary alcohol [III] with an organic sulfonyl chloride in the presence of an organic base (e.g. pyridine, triethylamine) or an inorganic base (e.g. sodium hydride) in an appropriate organic solvent to convert the alcohol into a corresponding organic sulfonic acid ester and then subjecting the ester to an etherification reaction with a basic skeletal phenolic hydroxy compound or alcohol [IV] in the presence of an inorganic base (e.g. potassium carbonate, sodium hydride) or a strong organic base. As the organic sulfonyl chloride referred to herein, there can be mentioned, for example, aromatic sulfonic acid chlorides such as p-toluenesulfonyl chloride, o-toluenesulfonyl chloride, p-chlorobenzenesulfonyl chloride, benzenesulfonyl chloride, α-naphthalenesulfonyl chloride, β-naphthalenesulfonyl chloride and the like; methanesulfonyl chloride; and trifluoromethanesulfonyl chloride. As the organic solvent used in the etherification reaction of the scheme 2, there can be mentioned hydrocarbons, halogenated hydrocarbons, ethers (e.g. diethyl ether, tetrahydrofuran, dioxane), ethyl acetate, acetonitrile, benzene, toluene, dimethylformamide (DMF), dimethyl sulfoxide (DMSO), hexamethylphosphoric triamide (HMPA), etc. The activation of the optically active dichiral secondary alcohol [III] includes, besides the above mentioned conversion into an organic sulfonic acid ester, conversion into a halide. The conversion of the optically active dichiral secondary alcohol [III] into a halide can be effected by a method in which said organic sulfonic acid ester is reacted with a metal halide (e.g. sodium iodide, potassium iodide) or a method in which the dichiral secondary alcohol [III] is directly reacted with a halogenating agent (e.g. thionyl chloride, thionyl bromide). The thus synthesized halide of the dichiral secondary alcohol [III] can be subjected to an etherification reaction with the basic skeletal phenolic hydroxy compound or alcohol [IV] in the presence of an inorganic base (e.g. potassium carbonate, sodium hydroxide) or a strong organic base in an organic solvent. The desired ether compound [I] thus produced can be isolated from the reaction mixture and purified by an ordinary separation and purification procedures (e.g. extraction, solvent operation, column chromatography, liquid chromatography, recrystallization).

Process 3

[Case in the general formula [I], the bond $Q_2$ between the skeletal component and the dichiral side chain component is a

bond]

Scheme 3

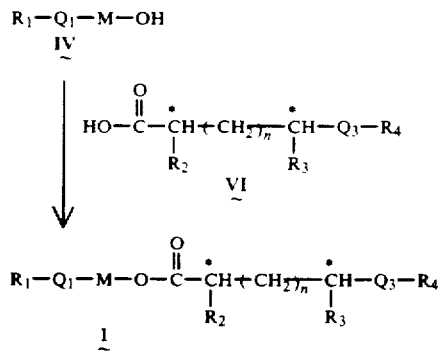

In the scheme 3, n, $R_1$, $R_2$, $R_3$, $R_4$, $Q_1$, $Q_3$, M and * mark have the same definitions as given previously.

The compound [I] can also be obtained by a known condensation reaction between a basic skeletal alcohol or phenolic hydroxy compound [IV] and an optically active dichiral carboxylic acid [VI] as shown in Scheme 3. This condensation reaction can be carried out according to a known conventional method.

In the above, the representative processes for producing the liquid crystal ester compound [I] and the liquid crystal ether compound [I] both of the present invention are described. However, the process for producing the liquid crystal compound [I] of the present invention is not restricted to the above processes in which the basic skeletal compound [II] or [IV] and the optically active dichiral secondary alcohol [III], the optically active dichiral derivative [V] or the optically active dichiral carboxylic acid [VI] are condensed. The liquid crystal compound [I]can be also be produced, for example, by condensing an alcohol or phenolic hydroxy compound containing an optically active dichiral component as a basic skeleton and a carboxylic acid or a phenolic hydroxy compound as another skeleton, or by condensing a carboxylic acid or phenolic hydroxy compound containing an optically active dichiral component as a basic skeleton and an alcohol or phenolic hydroxy compound as another skeleton.

When $Q_2$ is a group other than the above-mentioned ones, e.g., a carbonyl bond, single bond, carbonyldioxy bond, the compound [I] can also be produced according to the conventional method.

The optically active dichiral alcohol [III]and optically active dichiral derivative [V], both of which are materials for the important dichiral component of the present liquid crystal compound [I], can be derived from optically active dichiral compounds which are easily available as a reagent, and can also be obtained by a chemical asymmetric synthesis*7, a biological asymmetric synthesis*8 using an enzyme or a microorganism, or an optical resolution*9. The thus obtained optically active dichiral secondary alcohol [III] can be subjected to inversion of configuration on asymmetric carbon by a chemical or biological method to convert it into other optical isomer(s). As the typical methods for inverting the hydroxyl group of optically active secondary alcohol, there are known, for example, a method*10 in which the hydroxyl group is converted into an organic sulfonic acid ester and then subjected to an intramolecular nucleophilic substitution reaction to effect inversion, a method*11 in which an optically active secondary alcohol is activated by N,N'-dicyclohexylcarbodiimide (DCC) in the presence of cuprous chloride and then reacted with an appropriate carboxylic acid to effect inversion, and a method*12 in which an optically active secondary alcohol is reacted with diethyl azodicarboxylic acid (DEAD), triphenylphosphine (Ph$_3$P) and an appropriate carboxylic acid to effect inversion.

As a typical example of the optically active dichiral secondary alcohol [III] which is a material for the important dichiral component of the optically active compound [I] of the present invention, there can be mentioned a compound represented by the following formula.

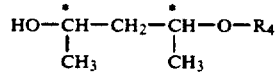

In the above formula, $R_4$ is a straight chain or branched chain alkyl group of 1-10 carbon atoms.) This is a compound of the formula [III] in which $R_2$ and $R_3$ are each $CH_3$, n is 1 and $Q_3$ is O (oxygen), and specifically is an optically active 3-alkyloxy-2-pentanol.

When $R_4$ is a straight alkyl chain of 1-10 carbon atoms, the compound includes optically active 3-methoxy-2-pentanol, 3-ethoxy-2-pentanol, 3-propoxy-2-pentanol, 3-butoxy-2-pentanol, 3-pentyloxy-2-pentanol, 3-hexyloxy-2-pentanol, 3-heptyloxy-2-pentanol, 3- octyloxy-2-pentanol, 3-nonyloxy-2-pentanol, 3-decyloxy-2-pentanol, etc.

When R$_4$ is a branched alkyl chain of 1–10 carbon atoms, the above compound includes optically active 3-isopropoxy-2-pentanol, 3-isobutoxy-2-pentanol, 3-tert-butoxy-2-pentanol, 3-(2-methylpentyloxy)-2-pentanol, 3-(3-methylpentyloxy)-2-pentanol, etc. Of these, preferable are compounds having, as R$_4$, a straight alkyl chain group of 3–6 carbon atoms, that is, 3-propoxy-2-pentanol, 3-butoxy-2-pentanol, 3-pentyloxy-2-pentanol, and 3-hexyloxy-2-pentanol.

The alkyl ester of 4-hydroxy-2-methylvaleric acid shown below is also a typical example of the optically active dichiral secondary alcohol [III].

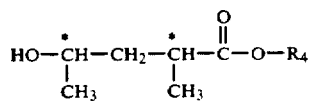

(In the above formula, R$_4$ is a straight alkyl chain or branched alkyl chain of 1–10 carbon atoms.) This is a compound of the formula [III] in which R$_2$ and R$_3$ are each CH$_3$, n is 1 and Q$_3$ is

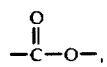

and specifically is an alkyl ester of optically active 4-hydroxy-2-methylvaleric acid.

When R$_4$ is a straight alkyl chain of 1–10 carbon atoms, the compound includes methyl ester, ethyl ester, propyl ester, butyl ester, pentyl ester, hexyl ester, heptyl ester, octyl ester, nonyl ester and decyl ester of optically active 4-hydroxy-2-methylvaleric acid. Of these, preferable are compounds of a straight alkyl chain of 3–6 carbon atoms, that is, propyl ester, butyl ester, pentyl ester and hexyl ester of optically active 4-hydroxy-2-methylvaleric acid.

The 3-acyloxy-2-pentanol shown below is also a typical example of the optically active dichiral secondary alcohol [III].

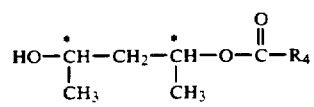

(In the above formula, R$_4$ is a straight alkyl chain or branched alkyl chain of 1–10 carbon atoms). This is a compound of the formula [III] in which R$_2$ and R$_3$ are each CH$_3$, n is 1 and Q$_3$ is

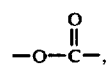

and specifically is an optically active 3-acyloxy-2-pentanol.

When R$_4$ is a straight alkyl chain of 1–10 carbon atoms, the compound includes optically active 3-acetyloxy-2-pentanol, optically active 3-propionyloxy-2-pentanol, optically active 3-butyryloxy-2-pentanol, optically active 3-pentanoyloxy 2-pentanol, optically active 3-hexanoyloxy-2-pentanol, optically active 3—heptanoyloxy-2-pentanol, optically active 3-octanoyloxy-2-pentanol, optically active 3-nonanoyloxy-2-pentanol and optically active 3-decyloxy-2-pentanol. When R$_4$ is a branched alkyl chain of 1–10 carbon atoms, the compound includes optically active 3-isobutyryloxy-2-pentanol, 3-isovaleryloxy-2-pentanol, 3-pyvaroyloxy-1-methylpropanol, etc.

When the radical $-(CH_2)_n$ of the optically active compound [I] of the present invention is a single bond, the optically active dichiral secondary alcohol [III] which is an important material for constituting the dichiral portion of the compound [I] includes, as a typical example, a 2-alkoxy-1-methylpropanol represented by the following formula:

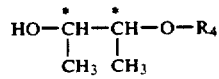

wherein R$_4$ is an alkyl group of 1–10 carbon atoms.

This alcohol specifically includes 3-methoxy-2-butanol, 3-ethoxy-2-butanol, 3-propoxy-2-butanol, 3-butoxy-2-butanol, 3-pentyloxy-2-butanol, 3-hexyloxy-2-butanol, 3-heptyloxy-2-butanol, 3-octyloxy-2-butanol, 3-nonyloxy-2-butanol, 3-decyloxy-2-butanol, 3-isopropoxy-2-butanol, 3-isobutoxy-2-butanol, 3-tert-butoxy-2-butanol, 3-(2-methylpentyloxy)-2-butanol, 3-(3-methyl-pentyloxy)-2-butanol, etc.

The optically active dichiral secondary alcohol [III] further includes an alkyl ester of a 3-hydroxy-2-methylbutyric acid represented by the following formula:

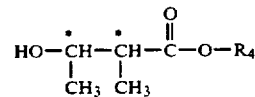

wherein R$_4$ is an alkyl group of 1–10 carbon atoms.

This compound specifically includes methyl ester, ethyl ester, propyl ester, butyl ester, pentyl ester, hexyl ester, heptyl ester, octyl ester, nonyl ester, decyl ester, isopropyl ester, isobutyl ester, tert-butyl ester, 2-methylpentyl ester, 3-methylpentyl ester of 3-hydroxy-2-methylbutyric acid, etc.

The optically active dichiral secondary alcohol [III] furthermore includes a 3-acyloxy-2-butanol represented by the following formula:

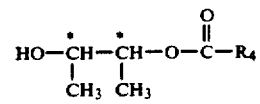

wherein R$_4$ is an alkyl group of 1–10 carbon atoms.

This compound specifically includes 3-acetyloxy-2-butanol, 3-propionyloxy-2-butanol, 3-butyryloxy-2-butanol, 3-pentanoyloxy-2-butanol, 3-hexanoyloxy-2-butanol, 3-heptanoyloxy-2-butanol, 3-octanoyloxy-2-butanol, 3-nonanoyloxy-2-butanol, 3-decyloxy-2-butanol, 3-isobutyryloxy-2-butanol, 3-isovaleryloxy-2-butanol, 3-pyvaroyloxy-2-butanol, etc.

The optically active dichiral carboxylic acid [VI] which is also an important material for constituting the dichiral portion of the optically active compound [I] of the present invention includes a 3-alkyloxy-2-methylbutyric acid represented by the following formula:

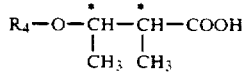

wherein $R_4$ is an alkyl group of 1-10 carbon atoms.

This acid specifically includes 3-methoxy-2-methylbutyric acid, 3-ethoxy-2-methylbutyric acid, 3-propoxy-2-methylbutyric acid, 3-butoxy-2-methylbutyric acid, pentyloxy-2-methylbutyric acid, 3-hexyloxy-2-methylbutyric acid, 3-heptyloxy-2-methylbutyric acid, 3-nonyloxy-2-methylbutyric acid, 3-decyloxy-2-butyric acid, 3-isopropoxy-2-methylbutyric acid, 3-isobutoxy-2-methylbutyric acid, 3-tert-butoxy-2-methylbutyric acid, 3-(2-methylpentyloxy)-2-methylbutyric acid, 3-(3-methylpentyloxy)-2-methylbutyric acid, etc.

The skeletal carboxylic acid, which is a material for the sekletal component of the optically active compound of the present invention and which is represented by the general formula [II], more specifically by the general formulas [II'] and [II''], is explained specifically.

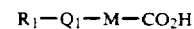 [II]

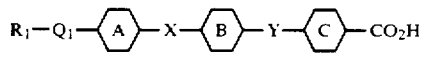 [II']

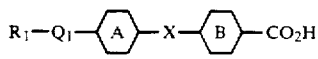 [II'']

When in the general formula [II'], $R_1$ is a straight alkyl chain or branched alkyl chain of 3-14 carbon atoms, $Q_1$ is a single bond or an ether bond

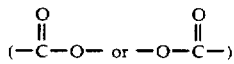

or
a single bond and

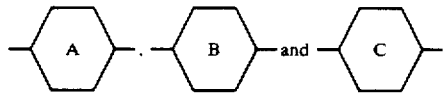

are a phenyl ring, the skeletal carboxylic acid [II] includes 4-(4'-alkyloxy or alkyl-4-biphenylcarbonyloxy)benzoic acid, 4-(4'-alkyloxy or alkyl-4-biphenyloxycarbonyl)benzoic acid, 4'-(4-alkyloxy or alkylphenylcarbonyloxy)-4-biphenylcarboxylic acid, 4'-(4-alkyloxy or alkylphenyloxycarbonyl)-4-biphenylcarboxylic acid, 4-{4-[4-(alkyloxy or alkyl)phenylcarbonyloxy]-4'-phenylcarbonyloxy}benzoic acid, 4-{4-[4-(alkyloxy or alkyl)phenyloxycarbonyl]-4'-phenylcarbonyloxy}benzoic acid, 4-{4-[4-(alkyloxy or alkyl)phenylcarbonyloxy]-4'-phenyloxycarbonyl}benzoic acid, 4-{4-[4-(alkyloxy or alkyl)phenyloxycarbonyl]-4'-phenyloxycarbonyl}benzoic acid, etc. When in the general formula [II''], $R_1$ is a straight alkyl chain or branched alkyl chain of 3-14 carbon atoms, $Q_1$ is a single bond or an ether bond, X is an ester bond

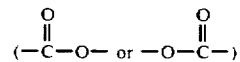

or a single bond

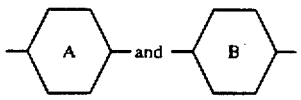

are a phenyl ring, the skeletal carboxylic acid [II] includes 4'-alkyloxy or alkyl-4-biphenylcarboxylic acid, 4-[4-(alkyloxy or alkyl)phenylcarbonyloxy]benzoic acid and 4-[4-(alkyloxy or alkyl)phenyloxycarbonyl]benzoic acid. As other typical examples of the skeletal carboxylic acid [II], there can be mentioned 4''-alkyloxy(or alkyl)-4-terphenylcarboxylic acid, 4'-(trans-4-alkyloxy or alkylcyclohexylcarbonyloxy)-4-biphenylcarboxylic acid, trans-4-(4'-alkyloxy or alkyl-4-biphenylcarbonyloxy)cyclohexanecarboxylic acid, 2-[4-(4-alkyloxy or alkylphenylcarbonyloxy)phenyl]pyridimidinyl-5-carboxylic acid, 2-(4'-alkyloxy or alkyl-4-biphenyl)-pyrimidinyl-5-carboxylic acid, 4'-(5-alkyloxy or alkylpyrimidinyl-2-oxycarbonyl)biphenyl-4-carboxylic acid, 4'-[2-(5-alkyloxy or alkyl)-2-(pyridyl)ethyl]biphenyl 4-carboxylic acid, 4-[4-(trans-5-alkyloxy or alkyl-1,3-dioxane-2-yl)phenylcarbonyloxy]benzoic acid, 4,-[4-(trans-5-alkyloxy or alkyl-1,3-dioxane-2-yl)]biphenyl-4-carboxylic acid, 2-[4-(4-alkyloxy or alkylphenylcarbonyloxy) phenyl)pyrazinyl-5-carboxylic acid, 2-(4'-alkyloxy or alkyl-4-biphenyl)pyrazinyl-5-carboxylic acid, 4'-(5-alkyloxy or alkylpyrazinyl-2-oxycarbonyl)-biphenyl-4-carboxylic acid, etc.

The skeletal alcohol or phenolic hydroxy compound which is a material for the skeletal component of the liquid crystal compound of the present invention is represented by the general formula [IV], more preferably the general formulas [IV'] and [IV''].

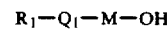 [IV]

[IV']

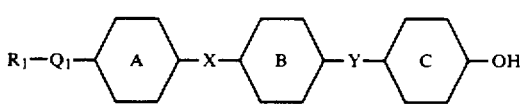

[IV'']

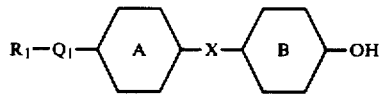

The skeletal alcohol or phenolic hydroxy compound is an alcohol or hydroxyl group derivative of the above mentioned carboxylic acid, obtained by replacing the carboxyl group of the latter with a hydroxyl group. Specific examples of the alcohol or phenolic hydroxy compound include 4-hydroxyphenyl ester of 4'-alkyloxy or alkylbiphenyl-4-carboxylic acid, 4'-alkyloxy or alkyl-4-biphenyl ester of 4'-hydroxybenzoic acid, 4'-hydroxy-4-biphenyl ester of 4-alkyloxy or alkylbenzoic acid, 4-alkyloxy or alkylphenyl ester of 4'-hydroxybiphenyl-4-carboxylic acid, 4'-hydroxy-4-biphenyl ester of trans-4-alkyloxy or alkylcyclohexanecarboxylic acid, trans 4-hydroxycyclohexyl ester of 4'-alkyloxy or alkyl-4-biphenylcarboxylic acid, 4-(5- hydroxy-2pyrimidinyl)phenyl ester of 4-alkyloxy or alkylbenzoic acid, 2-(4'-alkyloxy or alkyl-4-biphenyl)-pyrimidine-5-ol, 5-alkyloxy or alkyl-2-pyridinyl ester of 4'-hydroxy-4-biphenylcarboxylic acid, 4'-[2-(5-alkyloxy or alkyl-2-pyridyl)ethyl]biphenyl-4-ol, 4-hydroxyphenyl ester of 4-[4-(trans-5-alkyloxy or alkyl)-1,3-dioxane-2-yl]benzoic acid and 5-alkyloxy or 5-alkyl-2-pyrazinyl ester of 4'-hydroxy-4-biphenylcarboxylic acid.

In the above, there have been listed the typical examples of the skeletal carboxylic acid [II] and the skeletal alcohol or phenolic hydroxy compound [IV] which are contained in the optically active of the present invention, as well as the typical examples of the optically active dichiral alcohol [II] which is a material for the optically active dichiral side chain component contained in the optically active compound of the present invention. While the optically active compound [I] of the present invention can be produced by appropriately combining one of the skeletal components and one of the optically active dichiral components, the properties of the optically active compound [I] of the present invention is dependent upon both of the skeleton containing the nonchiral alkyl side chain and the optically active dichiral component used. Both of the skeletal component and the optically active dichiral component are not restricted to the above mentioned examples.

*1) A. Stempel and F. W. Landgraf, J. Org. Chem., 27, 4675 (1962); A. Hassner and V. Alexanian, Tetrahedron Lett., 1978, 4475.
*2) T. Mukaiyama et al., Chemistry Lett., 1975, 1045; T. Mukaiyama et al., Chemistry Lett., 1976, 13; K. Saigo et al., Bull. Chem. Soc. Japan, 50, 1863 (1977).
*3) O. Mitsunobu and M. Yamada, Bull. Chem. Soc. Japan, 40, 2380 (1967).
*4) M. Saroja and T. N. B. Kaimal, Syn. Commun., 16, 1423 (1986).
*5) S. Kim and W. J. Lee, Syn. Commun., 16, 659 (1986).
*6) S. Bittner and Y. Assaf, Chem. & Ind., 1975, 281.
*7) "Asymmetric Synthesis," vol. 1 (1983) - Vol. 5 (1985), ed. by J. D. Morrison, Academic Press, Orland; "Asymmetric Catalysis," ed. by B. Bosnich, Martinus Nijhoff Publ., Dordecht (1986); M. A. Sutter and D. Seebach, Ann., 1983, 939.
*8) "Applications of Biochemical Systems in Organic Chemistry*, ed. by J. B. Jones, C. J. Sih and D. Perlman, John, Wiley, New York (1976); G. Frater et al., Tetrahedron, 40, 1269 (1984); R. W. Hoffmann et al., Chem. Ber., 114, 2786 (1981); K. Nakamura et al., Tetrahedron Lett., 27, 3155 (1986).
*9) J. Jacques, A. Collet, S. H. Wilen, "Enantiomers, Racemates and Resolutions." John Wiley & Sons (1981); A. W. Ingersoll, Org. Synth., Coll. Vo., 2,506 (1943); H. Nohira et al., Chemistry Lett., 1981, 857, 951.
*10) E. J. Corey et al., Tetrahedron Lett., 1975, 3183; D. T. Sawyer and M. J. Gibian, Tetrahedron, 35, 1471 (1979).
*11) J. Kaulen, Angew. Chem, 99, 800 (1987).
*12) O. Mitsunobu and E. Eguchi, Bull. Chem. Soc. Japan, 44, 3427 (1971); Review: O. Mitsunobu, Synthesis, 1981, 1.

The present invention is explained in more detail by way of Examples.

EXAMPLE 1

Production of 4-[(1R 2R)-2-butoxy-1-methylpropoxycarbonyl]phenyl ester of 4'-octyloxy-4-biphenylcarboxylic acid (a compound of the general formula [I'] in which n is 0, $R_1$ is n-$C_8H_{17}$, $R_2$ and $R_3$ are each $CH_3$, $R_4$ is n-$C_4H_9$, $Q_1$ and $Q_3$ are each —O—, X is a single bond, $Q_2$ and Y are each

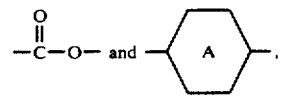

are each

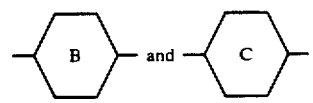

are each

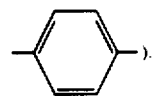

i) Production of (2R, 3R)-3-butoxy-2-butanol

The title alcohol can be produced according to the following scheme.

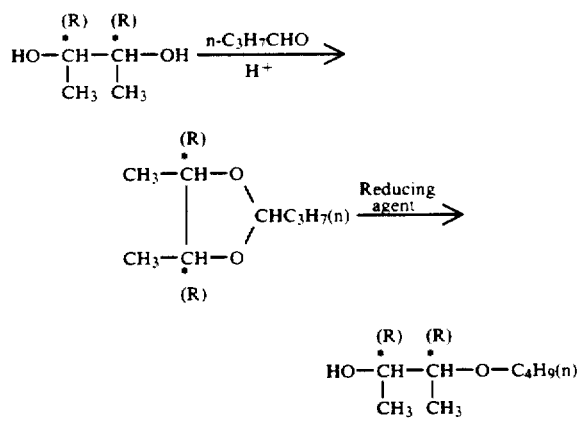

10.0 g of (2R, 3R)-(−)-2,3-butanediol and 10.4 g of n-butyl aldehyde were dissolved in 100 ml of benzene. Thereto was added 0.2 g of p-toluenesulfonic acid monohydrate. The mixture was refluxed for 2 hours with removing water according to a conventional method. After the completion of the reaction, 0.1 ml of pyridine was added and the mixture was concentrated under reduced pressure. The residue was subjected to distillation under reduced pressure (b.p. 58°-59° C./30 mmHg) to obtain 14.5 g of a butylidene derivative of (2R, 3R)-(−)-2,3-butanediol.

Under ice-cooling, 26.7 g of aluminum chloride was dissolved in 200 ml of dry ether, and thereto was added 1.90 g of lithium aluminum hydride in small portions. Thereto was dropwise added 14.5 g of the above obtained butylidene derivative under ice-cooling. The mixture was stirred overnight with cooling to room temperature. After the completion of the reaction, 150 ml of 10% sulfuric acid was added dropwise with stirring under ice-cooling. The ether layer was separated and the aqueous layer was extracted with ether twice. The combined ether layer was dried and concentrated. The residue was subjected to distillation under reduced pressure (b.p. 84°-86° C./33 mmHg) to obtain 13.4 g of (2R, 3R)-3-butoxy-2-butanol.

The ¹H-NMR and IR spectrum data of the above compound are shown below.

¹H-NMR (90 MHz, CDCl₃)

δ: 0.93 (3H, t), 1.09 (3H, d, J=5.9 Hz), 1.14 (3H, d, J=6.1 Hz), 1.20-1.73 (4H, m), 2.76 (1H, d, OH), 3.16 (1H, m), 3.30-3.76 (3H, m)

IR $\nu^{neat}_{max}$ cm⁻¹ 3150-3600 ii) Esterification 2.49 g of the (2R, 3R)-3-butoxy-2-butanol produced in the above i) was dissolved in 25 ml of dry tetrahydrofuran. Thereto were added 3.30 g of 1,1,1,3,3,3-hexamethyldisilazane and one drop of trimethylsilyl chloride, and the mixture was refluxed for 12 hours. The mixture was concentrated under reduced pressure. The residue was subjected to distillation under reduced pressure (b.p. 92°-97° C./30 mmHg) to obtain 2.93 g of trimethylsilyl ether of (2R, 3R)-3-butoxy-2-butanol.

Separately, 40 ml of thionyl chloride was added to 3.00 g of 4-(4'-octyloxy-4-biphenylcarboxyoxy)benzoic acid. The mixture was refluxed for 3 hours. Excessive thionyl chloride was removed by concentration under reduced pressure to obtain a corresponding acid chloride. Thereto were added 50 ml of dry acetonitrile, 1.47 g of the above obtained trimethylsilyl ether of (2R,3R)-3-butoxy-2-butanol and 0.09 g of zinc chloride, and the mixture was refluxed for 1 hour. After the completion of the reaction, the mixture was concentrated, and the residue was subjected to column chromatography [silica gel, developing solvent=dichloromethane) and then to recrystallization from ethanol to obtain 42 g of the title compound.

The ¹H-NMR, IR spectrum, elemental analysis and specific rotation power of the compound are shown below.

¹H-NMR (90 MHz, CDCl₃)

δ: 0.89 (6H, t), 1.20 (3H, d, J=6.4Hz), 1.32 (3H, d, J=6.4Hz), 1.15-1.95 (16H, m), 3.52 (3H, m), 4.02 (2H, t), 5.22 (1H, m), 6.90-8.30 (12H, m)

IR $\nu^{KBr}_{max}$ cm⁻¹ : 1735, 1710, 1600, 1500, 825, 760

Elemental analysis

Calcd. for C₃₆H₄₆O₆: C, 75.23; H, 8.07

Found: C, 75.30; H, 8.07

[α]²⁸_D: −17.1° (c=1.09, chloroform)

EXAMPLE 2

Production of 4-[(1S,2R)-2-butoxy-1-methylpropoxycarbonyl]phenyl ester of 4'-octyloxy-4-biphenylcarboxylic acid (a compound of the general formula [I'] in which n is 0, R₁ is n-C₈H₁₇, R₂ and R₃ are each CH₃, R₄ is n-C₄H₉, Q₁ and Q₃ are each —O—, X is a single bond, Q₂ and Y are each

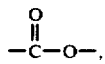

and

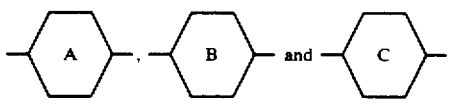

are each

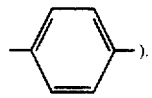

In 50 ml of dry tetrahydrofuran were dissolved 0.72 g of the (2R,3R)-3-butoxy-2-butanol produced in Example 1 i), 2.00 g of 4-(4'-octyloxy-4-biphenylcarbonyloxy)benzoic acid and 2.3 g of triphenylphosphine. Thereto was dropwise added 1.56 g of diethyl azodicarboxylate. The mixture was stirred for 30 minutes at room temperature. The mixture was concentrated under reduced pressure. The residue was subjected to column chromatography [silica gel, developing solvent=hexane-ethyl acetate (5:1)] and then to recrystallization from ethanol to obtain 1.28 g of the title compound.

The ¹H-NMR, IR spectrum, elemental analysis and specific rotation are shown below.

¹H-NMR (90 MHz, CDCl₃)

δ: 0.90 (3H, t), 0.91 (3H, t), 1.22 (3H, d, J=6.4 Hz), 1.35 (3H, d, J=6.5Hz), 1.15-2.00 (16H, m), 3.53 (3H, m), 4.02 (2H, t), 5.16 (1H, m), 6.90 −8.30 (12H, m)

IR $\nu^{KBr}_{max}$ cm⁻¹: 1735, 1710, 1600, 1500, 830, 760

Elemental analysis

Calcd. for C₃₈H₄₆O₆: C, 75.23; H, 8.07

Found C, 75.11; H, 7.87

[α]²³_D: +11.7° (c=1.04, chloroform)

EXAMPLE 3

Production of 4'-octyloxy-4-biphenyl ester of 4[(1R2R)-2-butoxy-1-methylpropoxy]benzoic acid (a compound of the general formula [I']in which n is 0, R₁ is n-C₈H₁₇, R₂ and R₃ are each CH₃, R₄ is n-C₄H₉, Q₁, Q₂ and Q₃ are each —O—, X is a single bond, Y is

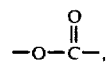

and

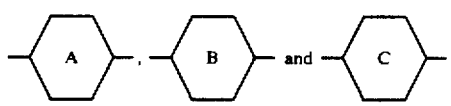

are each

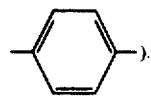

i) Production of (2S,3R)-3-butoxy-2-butanol

This optically active alcohol can be produced by subjecting the (2R,3R)-3-butoxy-2-butanol produced in Example 1 i) to the inversion of hydroxyl group according to the following scheme.

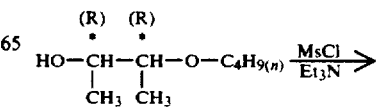

-continued

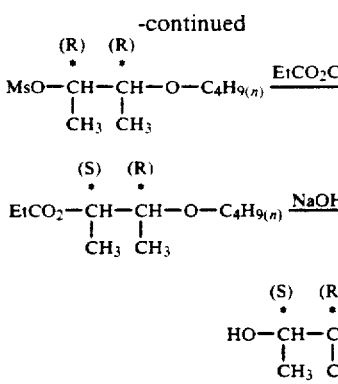

1.00 g of (2R,3R)-3-butoxy-2-butanol and 0.83 g of triethylamine were dissolved in 10 ml of dichloromethane. Thereto was dropwise added 0.94 g of methanesulfonyl chloride with ice-cooling. The mixture was stirred overnight at room temperature. The mixture was poured into water and extracted with dichloromethane. The organic layer was washed with dilute hydrochloric acid and an aqueous sodium bicarbonate solution in this order, and then dried and concentrated under reduced pressure. The residue was subjected to Kugel-rohr distillation (1 mmHg) to obtain 1.30 g of (2R,3R)-3-butoxy-2-butyl methanesulfonate.

Independently, 1.97 g of cesium carbonate was dissolved in 50 ml of methanol. Thereto was dropwise added 1.34 g of propionic acid. The mixture was stirred for 1 hour at room temperature. The mixture was concentrated under reduced pressure removed. The residue was mixed with toluene and the mixture was concentrated under reduced pressure (addition of 50 ml of toluene and concentration was carried out three times) to obtain a white powder of cesium propionate. This powder and 0.68 g of the above obtained (2R,3R)-3-butoxy-2-butyl methanesulfonate were dissolved in 50 ml of dry N,N-dimethylformamide. The mixture was heated overnight at 100° C. After the completion of the reaction, the mixture was poured into water. The resulting mixture was extracted with ether three times. The extract was washed with water (twice), dilute hydrochloric acid (once) and an aqueous sodium bicarbonate solution (once), and dried and concentrated. The reside was subjected to Kugel-rohr distillation (23 mmHg) to obtain 0.37 g of (2S,3R)-3-butoxy-2butyl propionate.

0.37 g of the compound was dissolved in 8 ml of methanol. Thereto was added 2 ml of a 1 N methanol solution of sodium hydroxide. The mixture was stirred overnight at room temperature. After the completion of the reaction, the mixture was concentrated under reduced pressure. To the residue was added water and the mixture was extracted with dichloromethane three times. The extract was dried and concentrated. The residue was subjected to Kugel-rohr distillation (22 mmHg) to obtain 0.22 g of (2S,3R)-3-butoxy-2-butanol.

The $^1$H-NMR and IR spectrum data of the compound are shown below.

$^1$H-NMR (90 MHz, CDCl$_3$)

δ: 0.92 (3H, t), 1.09 (3H, d, J=6.3Hz), 1.11 (3H, d, J=6.5Hz), 1.20–1.66 (4H, m), 2.08 (1H, d, OH), 3.13–3.62 (3H, m), 3.83 (1H, m)

IR $\nu^{neat}_{max}$ cm$^{-1}$: 3150–3650 ii) Condensation

In 10 ml tetrahydrofuran were dissolved 0.22 g of the (2S, -2-butanol produced in the above i), 0.62 g of 4'-octyloxy-4-biphenyl 4-hydroxybenzoate and 0.59 g of triphenylphosphine. Thereto was dropwise added 0.39 g of diethyl azodicarboxylate. The mixture was stirred for 1 hour at room temperature. The mixture was concentrated under reduced pressure. The residue was subjected to column chromatography (silica gel, developing solvent = dichloromethane) and then to recrystallization from ethanol to obtain 0.43 g of the title compound.

The $^1$H-NMR, IR spectrum, elementary analysis and specific rotation of the compound are shown below.

$^1$H-NMR (90 MHz, CDCl$_3$)

δ: 0.90 (6H, t), 1.20 (3H, d, J=6.4Hz), 1.31 (3H, d, J=6.2Hz), 1.10–1.97 (16H, m), 3.54 (3H, m), 4.00 (2H, t), 4.52 (1H, m), 6.80–8.20 (12H, m)

IR $\nu^{KBr}_{max}$ cm$^{-1}$: 1730, 1605, 1500, 840, 810, 760

Elementary analysis

Calcd. for C$_{35}$H$_{46}$O$_5$: C, 76.89; H, 8.48

Found C, 77.16; H, 8.53

$[\alpha]^{22}_D$: 0 (c=0.612, chloroform)

EXAMPLE b 4

Production of 4'-octyloxy-4-biphenyl ester of 4-[(1S,2R)-2-butoxy-1-methylpropoxy]benzoic acid (a compound of the general formula [I'] in which n is 0, R$_1$ is n-C$_8$H$_{17}$, R$_2$ and R$_3$ are each CH$_3$, R$_4$ is n-C$_4$H$_9$, Q$_1$, Q$_2$ and Q$_3$ are each —O—, X is a single bond, Y is

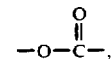

and

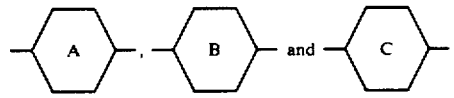

are each

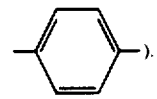

0.84 g of the (2R,3R)-3-butoxy-2-butanol produced in Example 1 i) and 2.00 g of 4-octyloxy-4-biphenyl ester of 4-hydroxybenzoic acid were subjected to the same procedure as in Example 3 ii) to obtain 1.22 g of the title compound.

The $^1$H-NMR, IR spectrum, elementary analysis and specific rotation of the compound are shown below.

$^1$H-NMR (90 MHz, CDCl$_3$)

α: 0.89 (3H, t), 0.92 (3H, t), 1.23 (3H, d, J=6.3 Hz), 1.36 (3H, d, J=6.2Hz), 1.10–2.00 (16H, m), 3.54 (3H, m), 4.00 (2H, t), 4.40 (1H, m), 6.80–8.20 (12H, m)

IR $\nu^{KBr}_{max}$ cm$^{-1}$: 1730, 1610, 1500, 840, 810, 760

Elementary analysis

Calcd. for C$_{35}$H$_{46}$O$_5$: C, 76.89; H, 8.48

Found C, 77.11; H, 8.53

$[\alpha]^{30}_D$: +6.63° (c=1.10, chloroform)

EXAMPLE 5

Production of 4-[(1S,2R)-2-butoxy-1-methylpropoxy]phenyl ester of 4'-octyloxy-4biphenylcarboxylic acid (a compound of the general formula [I'] in which n is O, R is n-C$_8$H$_{17}$, R$_2$ and R$_3$ are each CH, R$_4$ is n-C$_4$H$_9$, Q$_1$, Q$_2$ and Q$_3$ are each —O—, X is a single bond Y is

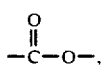

and

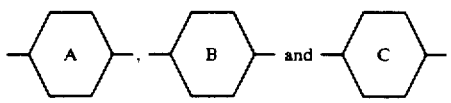

are each

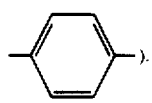

0.45 g of the (2R,3R)-3-butoxy-2-butanol produced in Example 1 i) and 1.50 g of 4-hydroxyphenyl ester of 4'-octyloxy-4-biphenylcarboxylic acid were subjected to the same procedure as in Example 3 ii) to obtain 0.63 g of the title compound.

The elementary analysis and specific rotation of the compound are shown below.
Elementary analysis
Calcd. for C$_{35}$H$_{48}$O$_5$: C 76.89; H, 8.48
Found C, 77.05; H, 8.53
[α]$^{26}_D$: +7.05° (c=1.02, chloroform)

EXAMPLE 6

Production of 4-octyloxyphenyl ester of 4'-[(1S,2R)-2-butoxy-1-methylpropoxy]-4-biphenylcarboxylic acid (a compound of the general formula [I'] in which n is 0, R$_1$ is n-C$_8$H$_{17}$, R$_2$ and R$_3$ are each CH$_3$, R$_4$ is n-C$_4$H$_9$, Q$_1$, Q$_2$ and Q$_3$ are each —O—, X is

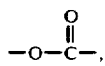

Y is a single bond, and

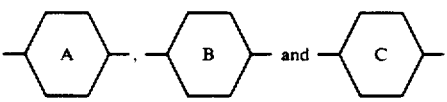

are each

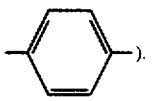

0.53 g of the (2R, 3R)-3-butoxy-2-butanol produced in Example 1 i) and 1.50 g of 4-octyloxyphenyl ester of 4'-hydroxy-4-biphenylcarboxylic acid were subjected to the same procedure as in Example 3 ii) to obtain 0.57 g of the title compound.

The elementary analysis and specific rotation of the compound are shown below.
Elementary analysis
Calcd. for C$_{35}$H$_{48}$O$_5$: C, 76.89; H, 8.48;
Found C, 76.83; H, 8.48.

[α]$^{26}_D$: +4.44° (c=0.844, chloroform)

EXAMPLE 7

Production of 4'-[(1S,2R)-2-butoxy-1-methylpropoxy]-4-biphenyl ester of 4-octyloxybenzoic acid (a compound of the general formula [I']in which n is 0, R$_1$ is n-C$_8$H$_{17}$, R$_2$ and R$_3$ are each CH$_3$, R$_4$ is n-C$_4$H$_9$, Q$_1$, Q$_2$ and Q$_3$ are each —O—, X is

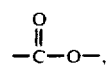

Y is a single bond, and

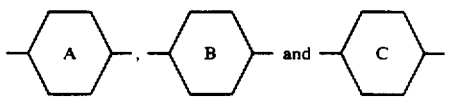

are each

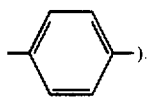

0.53 g of the (2R,3R)3-butoxy-2-butanol and 1.50 g of 4'-hydroxy-4-biphenyl ester of 4-octyloxybenzoic acid were subjected to the same procedure as in Example 3 ii) to obtain 0.61 g of the title compound.

The elementary analysis and specific rotation of the compound are shown below.
Elementary analysis
Calcd. for C$_{35}$H$_{48}$O$_5$: C, 76.89; H, 8.48;
Found C, 76.74; H, 8.59.
[α]$^{26}_D$: +4.75° (c=1.02, chloroform)

EXAMPLE 8

Production of 4'-octyloxy-4-biphenyl ester of 4-[(1S,2R)-2-octyloxy-1-methylpropoxy]-benzoic acid (a compound of the general formula [I'] in which n is 0, R$_1$ and R$_4$ are each n-C$_8$H$_{17}$, R$_2$ and R$_3$ are each CH$_3$, Q$_1$, Q$_2$ and Q$_3$ are each —O—, X is a single bond, Y is

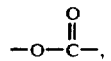

and

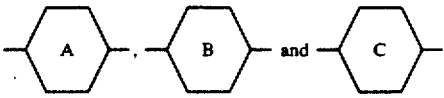

are each

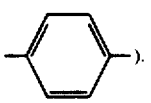

i) production of (2R,3R)-3-octyloxy-2-butanol
5 34 g of (2R,3R)-(−)-2,3-butanediol and 7.59 g of n-octyl aldehyde were subjected to the same procedure as in Example 1 i) to obtain 11.20 g of (2R,3R)-3-octyloxy-2-butanol (b.p. 71°–72° C./1 mmHg).

The $^1$H-NMR and IR spectrum data of the compound are shown below.

$^1$H-NMR (90 MHz, CDCl$_3$)

δ: 0.88 (3H, t), 1.09 (3H, d, J=6.2Hz), 1.14 (3H, d, J=6.1 Hz), 1.00–1.75 (12H, m), 2.76 (1H, d, OH), 3.12 (1H, m), 3.25–3.72 (3H, m)

IR $\nu^{neat}_{max}$ cm$^{-1}$: 3150–3650 ii) Condensation 0.33 g of the (2R,3R)-3-octyloxy-2-butanol produced in the above i) and 0.62 g of 4'-octyloxy-4-biphenyl ester of 4-hydroxybenzoic acid were subjected to the same procedure as in Example 3 ii) to obtain 0.49 g of the title compound.

The $^1$H-NMR, IR spectrum, elementary analysis and specific rotation of the compound are shown below.

$^1$H-NMR (90 MHz, CDCl$_3$)

δ: 0.89 (6H, t), 1.23 (3H, d, J=6.4Hz), 1.36 (3H, d, J=6.2Hz), 1.06–1.96 (24H, m), 3.50 (3H, m), 4.00 (2H, t), 4.40 (1H,m), 6.80–8.20 (12H, m)

IR $\nu^{KBr}_{max}$ cm$^{-1}$: 1730, 1600, 1500, 840, 760

Elementary analysis

Calcd. for C$_{39}$H$_{54}$O$_5$: C, 77.70; H, 9.03;

Found : C, 77,82; H, 8.96.

$[\alpha]^{25}_D$: +5.37° (c=0.614, chloroform)

EXAMPLE 9

Production of 4-[(1S,2R)-2-ethoxycarbonyl-1-methylpropoxycarbonyl]phenyl ester of 4'-octyloxy-4-biphenylcarboxylic acid (a compound of the general formula [I'] in which n is 0, R is n-C$_8$H$_{17}$, R$_2$ and R$_3$ are each CH$_3$, R$_4$ is C$_2$H$_5$, Q$_1$ is —O—, X is a single bond, Q$_2$, Q$_3$ and Y are each

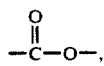

and

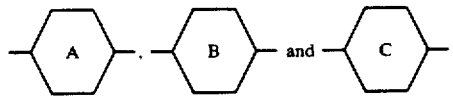

are each

).

i) Production of ethyl ester of (2R,3S)-3-hydroxy-2-methylbutyric acid

The title compound can be obtained according to a known method [R. W. Hoffman et al., Chem. Ber., 114, 2786 (1981)]. In this method, ethyl 2-methyl-3-oxobutyrate was subjected to asymmetric reduction using a baker's yeast to obtain the title compound and its diastereomer, that is, ethyl ester of (2S,3S)-3-hydroxy-2-methylbutyric acid at a ratio of (82:18) to (87:13). In the following Example 9 ii), Examples 10–18 and 21–26, this mixture was used without separation, and the final mixture obtained by condensation with a skeletal compound was subjected to purification such as column chromatography, recrystallization or the like to obtain a single diastereomer.

ii) Esterification 5.00 g of the ethyl ester of (2R,3S)-3-hydroxy-2-methylbutyric acid produced in the above i) was dissolved in 70 ml of dry tetrahydrofuran. Thereto were added 4.31 g of 1,1,1,3,3,3-hexamethyldisilazane and one drop of trimethylsilyl chloride, and the mixture was refluxed for 5 hours. The reaction mixture was concentrated and the residue was subjected to distillation under reduced pressure (b.p. 96° C./30 mmHg) to obtain 5.69 g of trimethylsilyl ether of ethyl ester of (2R,3S)-3-hydroxy-2-methylbutyric acid.

Independently, 2.50 g of 4-(4'-octyloxy-4-biphenylcarbonyloxy)benzoic acid was mixed with 40 ml of thionyl chloride, and the mixture was refluxed for 7 hours. Excessive thionyl chloride was removed by distillation to obtain the corresponding acid chloride. Thereto were added 50 ml of dry acetonitrile, 1.21 g of the above obtained trimethylsilyl ether of ethyl ester of (2R,3S)-3-hydroxy-2-methylbutyric acid and 0.08 g of zinc chloride. The mixture was refluxed for 1.5 hours. After the completion of the reaction, the reaction mixture was concentrated. The residue was subjected to column chromatography [silica gel, developing solvent =chloroform-n-hexane (9:1)] and then to recrystallization from ethanol to obtain 0.51 g of the title compound.

The $^1$H-NMR, IR spectrum, elementary analysis and specific rotation are shown below.

$^1$H-NMR (90 MHz, CDCl$_3$) 0.89 (3H, t), 1.15–1.7 (19H,m), 1.75–1.9 (2H, m), 2.7–2.95 (1H, m), 3.95–4.29 (4H, m), 5.2–5.5 (1H, m), 6.95–8.26 (12H, m)

IR $\nu^{KBr}_{max}$ cm$^{-1}$: 1740, 1710, 1600, 830, 760

Elementary analysis

Calcd. for C$_{35}$H$_{42}$O$_7$: C, 73.15; H, 7.37;

Found C, 73.31; H, 7.41.

$[\alpha]^{27}_D$: +11.6° (c=0.876, chloroform)

EXAMPLE 10

Production of 4-[(1S,2R)-2-butoxycarbonyl-1-methylpropoxycarbonyl]phenyl ester of 4'-octyloxy-4-biphenylcarboxylic acid (a compound of the general formula [I'] in which n is 0, R$_1$ is n-C$_8$H$_{17}$, R$_2$ and R$_3$ are each CH$_3$, R$_4$ is n-C$_4$H$_9$, Q$_1$ is —O—, X is a single bond, Q$_2$, Q$_3$ and Y are each

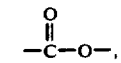

and

are each

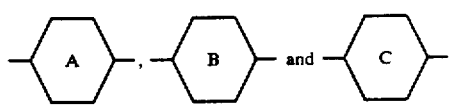

).

i) Production of butyl ester of (2R,3S)-3-hydroxy-2-methyl-butyric acid

This compound can be produced by the following scheme.

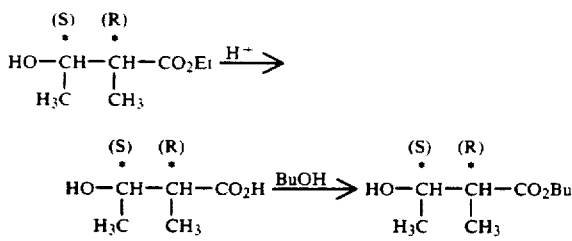

To 160 ml of water was added 8.00 g of the ethyl ester of (2R,3S)-3-hydroxy-2-methylbutyric acid produced in Example 9 i). Further, 40 ml of 36% hydrochloric acid was added. The mixture was heated for 6 hours at 80° C. The reaction mixture was extracted with ethyl acetate. The extract was dried and concentrated. The residue was subjected to distillation under reduced pressure (b.p. 90° C./1 mmHg) to obtain 3.34 g of (2R,3S)-3-hydroxy-2-methylbutyric acid. This compound was dissolved in 150 ml of n-butanol, and 0.2 ml of concentrated sulfuric acid was added. The mixture was refluxed for 7 hours with removing water produced by a molecular sieve (3A). The mixture was concentrated under reduced pressure and the residue was subjected to distillation under reduced pressure (b.p. 65° C./1 mmHg) to obtain 3.28 g of butyl ester of (2R,3S)-3-hydroxy-2-methylbutyric acid.

The $^1$H-NMR and IR spectrum of this compound are shown below.

$^1$H-NMR (90 MHz, CDCl$_3$)

δ: 0.86–1.71 (13H, m), 2.37–2.57 (2H, m), 3.85–4.2 (3H, m)

IR $\nu^{neat}_{max}$ cm$^{-1}$: 3400, 1730, 1460 ii) Esterification

The butyl ester of (2R,3S)-3-hydroxy-2-methylbutyric acid produced in the above i) was dissolved in 50 ml of dry tetrahydrofuran. Thereto were added 18.2 g of 1,1,1,3,3,3-hexamethyldisilazane and one drop of trimethylsilyl chloride, and the mixture was refluxed for 6 hours. The mixture was concentrated and the residue was subjected to distillation under reduced pressure (b.p. 130° C./47 mmHg) to obtain 4.15 g of trimethylsilyl ether of butyl ester of (2R,3S)-3-hydroxy-2-methylbutyric acid.

Independently, 2.50 g of 4-(4'-octyloxy-4-biphenylcarbonyloxy)benzoic acid was mixed with 40 ml of thionyl chloride, and the mixture was refluxed for 5 hours. Excessive thionyl chloride was removed under reduced pressure to obtain an acid chloride. This acid chloride was dissolved in 50 ml of dry acetonitrile, 1.42 g of the above obtained trimethylsilyl ether of butyl ester of (2R,3S)-3-hydroxy-2-methylbutyric acid and 0.08 g of zinc chloride. The mixture was refluxed for 3 hours. After the completion of the reaction, the mixture was concentrated under reduced pressure and the residue was subjected to rough purification by column chromatography [silica gel, developing solvent=dichloromethane-n-hexane (9:1)] and then to column chromatography (silica gel, developing solvent=dichloromethane) and further to recrystallization from ethyl acetate-n-hexane to obtain 1.52 g of the title compound.

The $^1$H-NMR, IR spectrum, elementary analysis and specific rotation of the compound are shown below.

$^1$H-NMR (90 MHz, CDCl$_3$)

δ: 0.8–1.0 (6H, m), 1.25–1.5 (20H, m), 1.6–1.95 (2H, m), 1.6–1.95 (1H, m), 4.02 (2H, t), 4.10 (2H, t), 5.2–5.55 (1H, m), 6.92–8.25 (12H, m)

IR $\nu^{KBr}_{max}$ cm$^{-1}$: 1740, 1730, 1720, 1605, 830, 760

Elementary analysis

Calcd. for C$_{37}$H$_{48}$O$_7$: C, 73.73; H, 7.69;

Found: C, 73.90; H, 7.76.

[α]$^{25}_D$: +13.7° (c=1.25, chloroform)

EXAMPLE 11

Production of 4-[(2R,3S)-3-methoxy-2-methylbutyloxy]phenyl ester of 4'-octyloxy-4-biphenylcarboxylic acid (a compound of the general formula [I'] in which n is 0, R$_1$ is n-C$_8$H$_{17}$, R$_2$, R$_3$ and R$_4$ are each CH$_3$, Q$_1$ and Q$_3$ are each —O—, X is a single bond, Y is

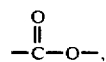

Q$_2$ is

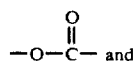

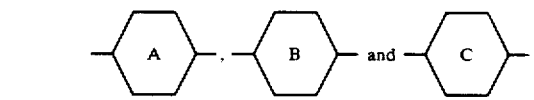

are each

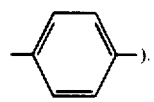

i) Production of (2R,3S)-3-methoxy 2-methylbutyric

This optically active carboxylic acid can be produced by the following scheme.

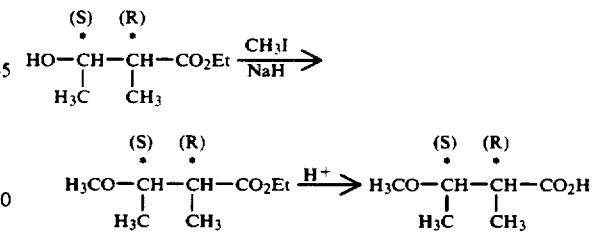

In 150 ml of N,N-dimethylormamide were dissolved 8.20 g of the ethyl ester of (2R,3S)-3-hydroxy-2-methylbutyric acid produced in Example 9 i) and 78.0 g of methyl iodide. To the solution was added in small portions 2.46 g of about 60% oily sodium hydride with ice cooling, and the mixture was stirred for 1 hour with ice cooling. The mixture was poured into 300 ml of ethyl acetate and the mixture was stirred for 10 minutes. The insoluble materials were removed by filtration and the filtrate was washed with water three times. The organic layer was dried and concentrated. The residue was subjected to distillation under reduced pressure (b.p. 80° C./30 mmHg) to obtain 6.87 g of ethyl ester of (2R,3S)-3-methoxy-2-methylbutyric acid.

2.55 g of this methyl ether compound was dissolved in 50 ml of dioxane. To the solution were added 10 ml of concentrated (36%) hydrochloric acid and 50 ml of water. The mixture was heated for 5 hours at 90° C. The mixture was poured into 100 ml of water. The mixture was extracted with ethyl acetate four times. The extract was dried and concentrated and the residue was subjected to distillation under reduced pressure (b.p. 105° C./1 mmHg) to obtain 1.49 g of (2R,3S)-3-methoxy-2-methylbutyric acid.

The $^1$H-NMR and IR spectrum of this compound are shown below.

$^1$H-NMR (90 MHz, CDCl$_3$)
δ: 1.15 (3H, s), 1.23 (3H, s), 2.5–2.8 (1H, m), 3.39 (3H, s) 3.47–3.74 (1H, m), 6.0 (1H, b)
IR $v^{neat}_{max}$ cm$^{-1}$: 3450, 1710, 1100 ii) Esterification

In 40 ml of dry tetrahydrofuran were dissolved 0.79 g of the (2R,3S)-3-methoxy-2-methylbutyric acid produced in the above i), 2.5 g of 4-hydroxyphenyl ester of 4'-octyloxy-4-biphenylcarboxylic acid and 2.66 g of tributylamine. Thereto was added 1.84 g of 2-chloro-1-methylpyridium iodide, and the mixture was refluxed for 7 hours. The insoluble materials were removed by filtration and the filtrate was concentrated under reduced pressure. The residue was subjected to column chromatography [silica gel, developing solvent = chloroform-n-hexane (4:1)] and then to recrystallization from ethanol to obtain 0.36 g of the title compound.

The $^1$H-NMR, IR spectrum, elementary analysis and specific rotation of the compound are shown below.

$^1$H-NMR (90 MHz, CDCl$_3$)
δ: 0.90 (3H, t), 1.05–1.6 (16H, m), 1.8 (2H, b), 2.65–2.9 (1H, m), 3.40 (3H, s), 3.6–3.82 (1H, m), 4.01 (2H, t), 6.94–8.25 (12H, m)
IR $v^{KBr}_{max}$ cm$^{-1}$: 1 1760, 1730, 1610, 1510, 1100, 830
Elementary analysis
Calcd. for C 006 C, 74.41; H, 7.57;
Found C, 74.69; H, 7.52.
$[\alpha]^{28}_D$: −5.69° (c=1.14, chloroform)

EXAMPLE 12

Production of 4'-octyloxy-4-biphenyl ester of 4-[(2R,3S)-3-methoxy-2-methylbutyloxy]-benzoic acid (a compound of the general formula [I'] in which n is 0, R$_1$ is n-C$_8$H$_{17}$, R$_2$, R$_3$ and R$_4$ are each CH$_3$, Q$_1$ and Q$_3$ are each —O—, X is a single bond, Y and Q$_2$ are each

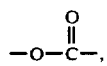

and

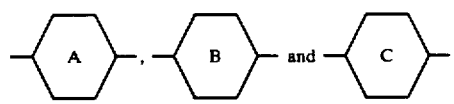

are each

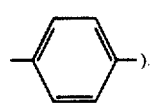

0.70 g of the (2R,3S)-3-methoxy-2-methylbutyric acid produced in Example 11 i) and 2.22 g of 4'-octyloxy-4-biphenyl ester of 4-hydroxybenzoic acid were subjected to the same procedure as in Example 11 ii) to obtain 0.52 g of the title compound.

The elementary analysis and specific rotation of the compound are shown below.

Elementary analysis
Calcd. for C$_{33}$H$_{40}$O$_6$: C, 74.41; H, 7.57;
Found C, 74.58; H, 7.59.
$[\alpha]^{27}_D$: −5.75° (c=0.828, chloroform)

EXAMPLE 13

Production of 4'-[(1R,2S)-2-methoxy-1-methylpropionylcarbonyloxy]-4-biphenyl ester of 4-octyloxybenzoic acid (a compound of the general formula [I'] in which n is 0, R$_1$ is n-C$_8$H$_{17}$, R$_2$, R$_3$ and R$_4$ are each CH$_3$. Q$_1$ and Q$_3$ are each —O—, X is

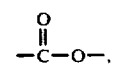

Y is a single bond, Q$_2$ is

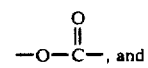

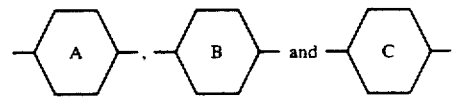

are each

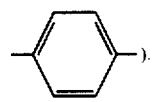

0.48 g of the (2R,3S)-3-methoxy-2-methylbutyric acid produced in Example 11 i) and 1.0 g of 4'- hydroxy-4-biphenyl ester of 4-octyloxybenzoic acid were mixed with 150 ml of dichloromethane. Thereto was added 1.35 g of triphenylphosphine bromide, and the mixture was refluxed for 7 hours. The reaction mixture was concentrated under reduced pressure. The residue was subjected to column chromatography [silica gel, developing solvent: chloroform-n-hexane (9:1)] and then to recrystallization from ethanol to obtain 0.63 g of the title compound.

The elementary analysis and specific rotation of the compound are shown below.

Elementary analysis
Calcd. for C$_{33}$H$_{40}$O$_6$: C, 74.41; H, 7.57;
Found: C, 74.52; H, 7.59.
$[\alpha]^{23}_D$: −8.99° (c=1.06, chloroform)

EXAMPLE 14

Production of 4-octyloxyphenyl ester of 4'-[(2R,3S)-3-methoxy-2-methylbutyryloxy-4-biphenylcarboxylic acid (a compound of the general formula [I'] in which n is 0, R$_1$ is n-C$_8$H$_{17}$, R$_2$, R$_3$ and R$_4$ are each CH$_3$, Q$_1$ and Q$_3$ are each —O— X and Q are each

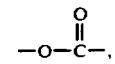

Y is a single bond, and

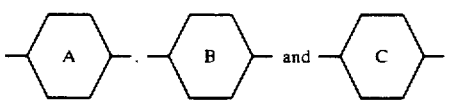

are each

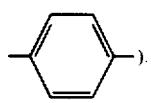).

0.48 g of the (2R,3S)-3-methoxy-2-methylbutyric acid produced in Example 11 i) and 1.0 g of 4-octyloxyphenyl ester of 4'-hydroxy-4-biphenylcarboxylic acid were subjected to the same procedure as in Example 13 to obtain 0.22 g of the title compound.

The elementary analysis and specific rotation of the compound are shown below.

Elementary analysis
Calcd. for $C_{33}H_{40}O_6$: C, 74.41; H, 7.57;
Found C, 74.66; H, 7.65.
$[\alpha]^{24}_D$: −93.7° (c=0.354, chloroform)

EXAMPLE 15

Production of 4-[(2R,3S)-3-butoxy-2-methylbutyryloxy]phenyl ester of 4'-octyloxy-4-biphenylcarboxylic acid (a compound of the general formula [I'] in which n is 0, $R_1$ is n-$C_8H_{17}$, $R_2$ and $R_3$ are each $CH_3$, $R_4$ is n-$C_4H_9$, $Q_1$ and $Q_3$ are each —O—, X is a single bond, Y is

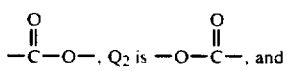

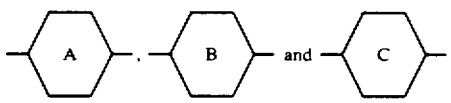

are each

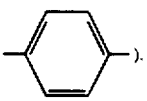).

i) Production of (2R,3S) 3-butoxy-2-methylbutyric acid

This optically active carboxylic acid can be produced by the following scheme.

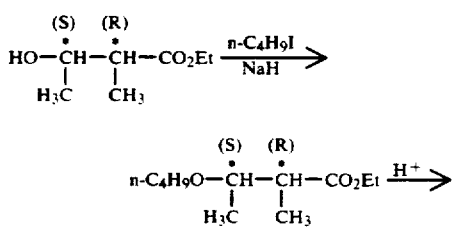

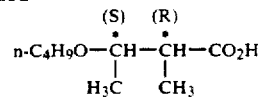

In 150 ml of N,N-dimethylformamide were dissolved 15.0 g of the ethyl ester of (2R,3S)-3-hydroxy-2-methylbutyric acid produced in Example 9 i) and 56.6 g of n-butyl iodide. To the solution was added in small portions 7.89 g of about 60% oily sodium hydride with ice cooling. The mixture was stirred for hours with ice cooling and poured into 300 ml of ethyl acetate. The resulting mixture was stirred for minutes. The insoluble materials were removed by filtration and the filtrate was washed with water four times. The organic layer was dried and concentrated. The residue was subjected to distillation under reduced pressure (b.p. 90°-95° C./30 mmHg) to obtain 8.32 g of ethyl ester of (2R,3S)-3-butoxy-2-methylbutyric acid.

1.78 g of this compound was dissolved in ml of dioxane. Thereto were added 5 ml of concentrated (36%) hydrochloric acid and 20 ml of water. The mixture was refluxed for 20 hours. The mixture was diluted with 20 ml of water, and the mixture was extracted with ethyl acetate five times. The extract was dried and concentrated. The residue was subjected to distillation under reduced pressure (b.p. 100–105° C./1 mmHg) to obtain 1.17 g of (2R,3S)-3-butoxy-2-methylbutyric acid.

$^1$H-NMR spectrum of this compound is shown below.

$^1$H-NMR (90 MHz, $CDCl_3$)

δ: 0.91 (3H, t), 1.15 (3H, s), 1.22 (3H, s), 1.3–1.6 (4H, m), 2.47–2.75 (1H, m), 3.29–3.8 (3H, m), 8.9 (1H, b)

ii) Esterification

To 1.1 g of the (2R,3S)-3-butoxy-2-methylbutyric acid produced in the above i) was added in small portions 5 ml of oxalyl chloride at room temperature. The mixture was stirred for 2 hours at room temperature and then for 30 minutes at 50° C. Excess oxalyl chloride was removed by distillation under reduced pressure. The residue was subjected to Kugel-rohr distillation under reduced pressure to obtain 0.88 g of (2R,3S)-3-butoxy-2-methylbutyric acid chloride.

0.88 g of this acid chloride and 1.00 g of 4-hydroxyphenyl ester of 4'-octyloxy-4-biphenylcarboxylic acid were dissolved in 20 ml of dry tetrahydrofuran.

Thereto was added 0.38 g of dry pyridine, and the mixture was stirred overnight at room temperature. The reaction mixture was concentrated. The residue was subjected to column chromatography (silica gel, developing solvent=dichloromethane) and then to recrystallization from ethyl acetate-methanol to obtain 0.52 g of the title compound.

The $^1$H-NMR, IR spectrum, elementary analysis and specific rotation of the compound are shown below.

$^1$H-NMR (90 MHz, $CDCl_3$)

δ: 0.9 (3H, t), 0.93 (3H, t), 1.15–1.6 (20H, m), 1.7–1.95 (2H, m), 2.6–2.9 (1H, m), 3.35–3.9 (3H, m), 4.05 (2H, t), 6.85–8.25 (12H, m)

IR $\nu^{KBr}_{max}$ cm$^{-1}$ 1750, 1730, 1605, 1505

Elementary analysis
Calcd. for $C_{36}H_{46}O_6$: C, 75.23; H, 8.07;
Found C, 75.02; H, 8.00.
$[\alpha]^{24}_D$: +6.63° (c=0.532, chloroform)

EXAMPLE 16

Production of 4'-octyloxy-4-biphenyl ester of 4-[(2R,3S)-3-butoxy-2-methylbutyryloxy]benzoic acid (a compound of the general formula [I'] in which n is 0, $R_1$ is n-$C_8H_{17}$, $R_2$ and $R_3$ are each $CH_3$, $R_4$ is n-$C_4H_9$, $Q_1$ and $Q_3$ are each —O—, X is a single bond, $Q_2$ and Y are each

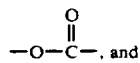

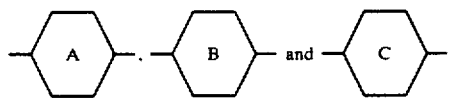

are each

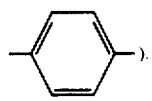

0.75 g of the (2R,3S)-3-butoxy-2-methylbutyric acid chloride produced in Example 15 ii) and 1.00 g of 4'-octyloxy-4-biphenyl ester of 4-hydroxybenzoic acid were subjected to the same procedure as in Example 15 ii) to obtain 0.85 g of the title compound.

The elementary analysis and specific rotation of this compound are shown below.

Elementary analysis

Calcd. for $C_{36}H_{46}O_6$: C, 75.23; H, 8.07;

Found C, 75.15; H, 8.05.

$[\alpha]^{24}_D$: −0.29° (c = 1.02, chloroform)

EXAMPLE 17

Production of 4'-[(2R,3S)-3-butoxy-2-methylbutyryloxy]-4-biphenyl ester of 4-octyloxybenzoic acid (a compound of the general formula [I'] in which n is 0, $R_1$ is n-$C_8H_{17}$, $R_2$ and $R_3$ are each $CH_3$, $R_4$ is n-$C_4H_9$, $Q_1$ and $Q_3$ are each —O—, X is

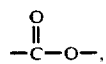

Y is a single bond, $Q_2$ is

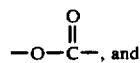

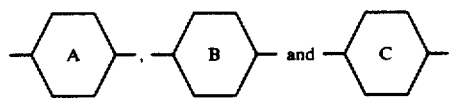

are each

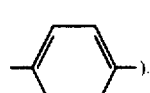

0.75 g of the (2R,3S)-3-butoxy-2-methylbutyric acid chloride produced in Example 15 ii) and 1.00 g of 4'-hydroxy-4-biphenyl ester of 4-octyloxybenzoic acid were subjected to the same procedure as in Example 15 ii) to obtain 0.62 g of the title compound.

The elementary analysis and specific rotation of this compound are shown below.

Elementary analysis

Calcd. for $C_{36}H_{46}O_6$: C, 75.23; H, 8.07;

Found C, 75.02; H, 8.07.

$[\alpha]^{24}_D$: −47.1° (c = 0.738, chloroform)

EXAMPLE 18

Production of 4-octyloxyphenyl ester of 4'-[(2R,3S)-3-butoxy-2-methylbutyloxy]-4-biphenylcarboxylic acid (a compound of the general formula [I'] in which n is 0, $R_1$ is n-$C_8H_{17}$, $R_2$ and $R_3$ are each $CH_3$, $R_4$ is n-$C_4H_9$, $Q_1$ and $Q_3$ are each —O—, X and $Q_2$ are each

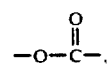

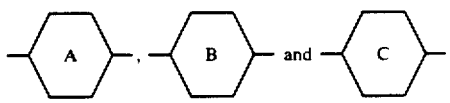

Y is a single bond and are each

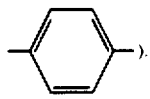

0.75 g of the (2R,3S)-3-butoxy-2-methylbutyric acid chloride produced in Example 15 ii) and 1.0 g of 4-octyloxyphenyl ester of 4'-hydroxy-4-biphenylcarboxylic acid were subjected to the same procedure as in Example 15 ii) to obtain 0.65 g of the title compound.

The elementary analysis and specific rotation of this compound are shown below.

Elementary analysis

Calcd. for $C_{36}H_{46}O_6$:C, 75.23; H, 8.07;

Found C, 75.33; H, 7.97.

$[\alpha]^{24}_D$: +0.40° (c = 0.646, chloroform)

EXAMPLE 19

Production of (1S,2R)-2-butoxy-1-methylpropyl ester of 4'-octyloxy-4-biphenylcarboxlic acid (a compound of the general formula [I'] in which n is 0, $R_1$ is n-$C_8H_{17}$, $R_2$ and $R_3$ are each $CH_3$, $R_4$ is n-$C_4H_9$, $Q_1$ and $Q_3$ are each —O—, $Q_2$ is

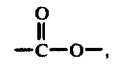

X is a single bond, and

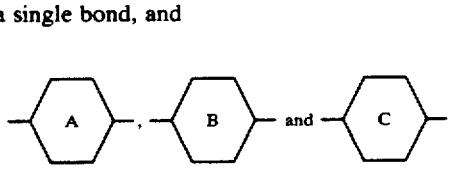

are each 0.45 g of the (2R,3R)-3-butoxy-2-butanol produced in Example 1 i) and 1.00 g of 4'-octyloxy-4-biphenylcarboxylic acid were subjected to the same procedure as in Example 2 to obtain 0.67 g of the title compound.

The elementary analysis and specific rotation of the compound are shown below.
Elementary analysis
Calcd. for $C_{29}H_{42}O_4$: C, 76.61; H, 9.31;
Found C, 76.52; H, 9.10.
$[\alpha]^{26}_D$: +15.5° (c=1.09, chloroform)

EXAMPLE 20

Production of 4-[(1S,2R)-2-butoxy-1-methylpropoxy-4'-octyloxybiphenyl] (a compound of the general formula [I''] in which n is 0, R is n-$C_8H_{17}$, $R_2$ and $R_3$ are each $CH_3$, $R_4$ is n-$C_4H_9$, $Q_1$, $Q_2$ and $Q_3$ are each —O—, X is a single bond, and

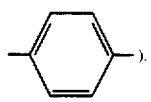

are

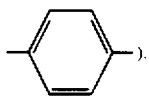

0.49 g of the (2R,3R)-3-butoxy-2-butanol produced in Example 1 i) and 1.00 g of 4'-octyloxybiphenyl-4-ol were subjected to the same procedure as in Example 3 ii) to obtain 0.49 g of the title compound.

The elementary analysis and specific rotation of the compound are shown below.
Elementary analysis
Calcd. for $C_{28}H_{42}O_3$: 203 C, 78.83; H, 9.92;
Found C, 78.87; H, 10.01;
$[\alpha]^{26}_D$: +5.70° (c=1.07, chloroform)

EXAMPLE 21

Production of (1S,2R)-2-butoxycarbonyl-1-methylpropyl ester of 4'-octyloxy-4-biphenylcarboxylic acid (a compound of the general formula [I''] in which n is 0, $R_1$ is n-$C_8H_{17}$, $R_2$ and $R_3$ are each $CH_3$, $R_4$ is n-$C_4H_9$, $Q_1$ is —O—, $Q_2$ and $Q_3$ are each $$-\overset{O}{\underset{\|}{C}}-O-,$$

X is a single bond, and

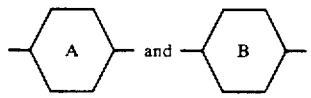

are each

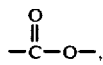

1.0 g of 4'-octyloxy-4-biphenylcarboxylic acid was mixed with 5 ml of thionyl chloride. The mixture was refluxed for 5 hours. Excess thionyl chloride was removed by distillation under reduced pressure to obtain an acid chloride. This acid chloride was mixed with 0.86 g of the ethyl ester of (2R,3S)-2-methyl-3-trimethylsiloxybutyric acid produced in Example 10 ii), 25 ml of acetonitrile and 0.038 g of zinc chloride. The mixture was refluxed for 5 hours. After the completion of the reaction, the mixture was concentrated under reduced pressure. The residue was subjected to column chromatography (silica gel, developing solvent=dichloromethane) and then to recrystallization from ethanol to obtain 0.76 g of the title compound.

The specific rotation of the compound is shown
$[\alpha]^{30}_D$: +22.5° (C=1.18, chloroform)

EXAMPLE 22

Production of 4'-octyloxy-4-biphenyl ester of (2R,3S)-3-butoxy-2-methylbutyric acid (a compound of the general formula [I''] in which n is 0, $R_1$ is n-$C_8H_{17}$, $R_2$ and $R_3$ are each $CH_3$, $R_4$ is n-$C_4H_9$, $Q_1$ and $Q_3$ are each —O—, $Q_2$ is $$-O-\overset{O}{\underset{\|}{C}}-,$$

X is a single bond, and

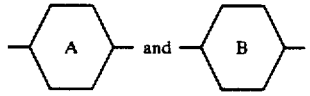

are each

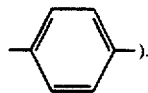

1.27 g of the 3-butoxy-2-methylbutyric acid octyloxybiphenyl-4-ol were subjected to the same procedure as in Example 15 ii) to obtain 0.94 g of the title compound.

The elementary analysis and specific rotatary power of the compound are shown below.
Elementary analysis
Calcd. for $C_{29}H_{42}O_4$: C, 76.61; H, 9.31;
Found C, 76.74, H, 9.48.
$[\alpha]^{25}_D$: +41.7° (c=1.18, chloroform)

EXAMPLE 23

Production of 4'-octyloxy-4-biphenyl ester of (2R,3S)-3-methoxy-2-methylbutyric acid (a compound of the general formula [I''] in which n is 0, $R_1$ is n-$C_8H_{17}$, $R_2$ and $R_3$ are each $CH_3$, $Q_1$ and $Q_3$ are each —O—, $Q_2$ is

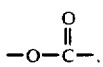

X is a single bond, and

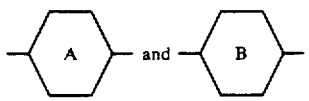

are each

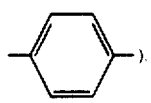

0.58 g of the (2R,3S)-3-methoxy-2-methylbutyric acid produced in Example 11 i) and 1.0 g of 4'-octyloxybiphenyl-4-ol were subjected to the same procedure as in Example 13 to obtain 0.11 g of the title compound.

The elementary analysis and specific rotation of the compound are shown below.

Elementary analysis
Calcd. for $C_{26}H_{36}O_4$: C, 75.69; H, 8.80;
Found C, 75.84; H, 8.91.
$[\alpha]^{26}_D$: $-15.5°$ (c=0.462, chloroform)

EXAMPLE 24

Production of 4-cotyloxyphenyl ester of 4'-[(2R,3S)-3-ethoxy-2-methylbutyryloxy]-4-biphenylcarboxylic acid (a compound of the general formula [I'] in which n is 0, $R_1$ is n-$C_8H_{17}$, $R_2$ and $R_3$ are each $CH_3$, $R_4$ is $C_2H_5$, $Q_1$ and $Q_3$ are each —O—, X and $Q_2$ are each

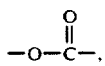

Y is a single bond, and

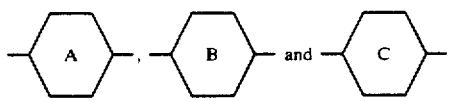

are each

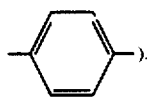

i) Production of (2R,3S)-3-ethoxy-2-methylbutyric acid chloride

This optically active carboxylic acid can be produced by the following scheme.

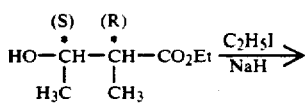

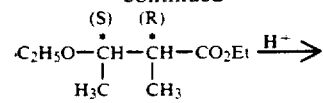

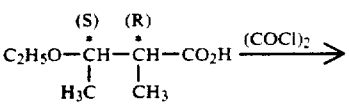

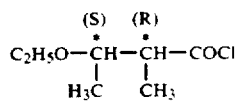

5.0 g of the (2R,3S)-3 hydroxy-2-methylbutyric acid ester produced in Example 9 i) and 15.0 g of ethyl iodide were dissolved in 50 ml of N,N-dimethylformamide. To this solution was added in small portions 2.05 g of about 60% oily sodium hydride with ice cooling. The mixture was stirred for 2 hours with ice cooling and then poured into 300 ml of ethyl acetate. The resulting mixture was stirred for 10 minutes. The insoluble materials were removed by filtration and the filtrate was washed with water four times. The organic layer was dried and concentrated. The residue was subjected to distillation under reduced pressure (b.p. 57–60° C./28 mmHg) to obtain 2.38 g of ethyl ester of (2R,3S)-3-ethoxy-2-methylbutyric acid.

This compound was dissolved in 30 ml of dioxane. To the solution were added concentrated (36%) hydrochloric acid and 50 ml of water. The mixture was refluxed for 6 hours. After the completion of the reaction, the mixture was extracted with ethyl acetate five times. The extract was dried and concentrated. To the residue was added in small portions 7 ml of oxalyl chloride at room temperature. The mixture was stirred for 1 hour at 40° C. Excess oxalyl chloride was removed by distillation under reduced pressure. The residue was subjected to Kugel-rohr distillation to obtain 1.18 g of (2R,3S)-3-ethoxy-2-methylbutyric acid chloride.

ii) Esterification 0.38 g of the (2R,3S)-3-ethoxy-2-methylbutyric acid chloride produced in the above i) and 100 g of 4-octyloxyphenyl ester of 4'-hydroxy-4-biphenylcarboxylic acid were dissolved in 20 ml of dry tetrahydrofuran. Thereto was added 0.38 g of dry pyridine, and the mixture was stirred overnight at room temperature. The mixture was concentrated. The residue was subjected to rough purification by column chromatography (silica gel, developing solvent=dichloromethane) and then to column chromatography [silica gel, developing solvent=n-hexane ethyl acetate (95:5)] and further to recrystallization from ethanol to obtain 0.29 g of the title compound.

$^1$H-NMR, IR spectrum, elementary analysis and specific rotation of the compound are shown below.

IR $\nu^{KBr}_{max}$ cm$^{-1}$: 1 1760, 1740, 1520
$^1$H-NMR (90 MHz, CDCl$_3$)
δ: 0.89 (3H, t), 1.14–1.50 (19H, m), 1.8 (2H, b), 2.65–2.95 (1H, m), 3.35–4.03 (5H, m), 6.86–8.28 (12H, m)

Elementary analysis
Calcd. for $C_{34}H_{42}O_6$: C, 74.70; H, 7.74;
Found C, 74.87; H, 7.75.
$[\alpha]^{26}_D$: $-19.5°$ (c=0.650, chloroform)

EXAMPLE 25

Production of 4-propoxyphenyl ester of 4'-[(2R,3S)-3-ethoxy-2-methylbutyryloxy]-4-biphenylcarboxylic acid (a compound of the general formula [I'] in which n is 0, $R_1$ is n-$C_3H_7$, $R_2$ and $R_3$ are each $CH_3$, $R_4$ is $C_2H_5$, $Q_1$ and $Q_3$ are each —O—, X and $Q_2$ are each

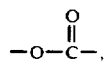

Y is a single bond, and

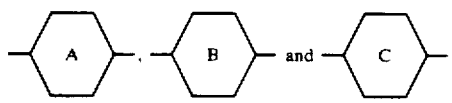

are each

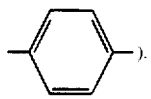

0.39 g of the (2R,3S)-3-ethoxy-2-methylbutyric acid chloride produced in Example 24 i) and 0.83 g of 4-propoxyphenyl ester of 4'-hydroxy-4-biphenylcarboxylic acid were subjected to the same procedure as in Example 24 ii) to obtain 0.20 g of the title compound.

The elementary analysis and specific rotation of the compound are shown below.

Elementary analysis
Calcd. for $C_{29}H_{32}O_6$: C, 73.09; H, 6.77;
Found C, 73.17; H, 6.70.
$[\alpha]^{25}_D$: −14.6° (c=0.642, chloroform)

EXAMPLE 26

Production of 4-octylphenyl ester of 4'-[(2R,3S)-3-ethoxy-2-methylbutyryloxy]-4-biphenylcarboxylic acid (a compound of the general formula [I'] in which n is 0, $R_1$ is n-$C_8H_{17}$, $R_2$ and $R_3$ are each $CH_3$, $R_4$ is $C_2H_5$, $Q_1$ and Y are each a single bond, X and $Q_2$ are each

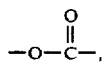

$Q_3$ is —O—, and

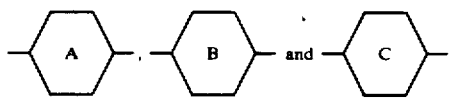

are each

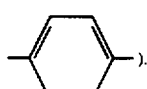

0.39 g of the (2R,3S)-3-ethoxy-2-methylbutyric acid chloride produced in Example 24 i) and 0.95 g of 4-octylphenyl ester of 4'-hydroxy-4-biphenylcarboxylic acid were subjected to the same procedure as in Example 24 ii) to obtain 0.48 g of the title compound.

The elementary analysis and specific rotation of the compound are shown below.

Elementary analysis
Calcd. for $C_{34}H_{42}O_5$: C, 76.95; H, 7.98;
Found C, 76.66; H, 7.94.
$[\alpha]^{26}_D$: −16.6° (c=0.866, chloroform)

EXAMPLE 27

Production of 4'-octyloxy-4-biphenyl ester of 4-[(1R,2S)-2-butoxy-1-methylpropoxy]-benzoic acid (a compound of the general formula [I'] in which n is 0, $R_1$ is n-$C_8H_{17}$, $R_2$ and $R_3$ are each $CH_3$, $R_4$ is n-$C_4H_9$, $Q_1$, $Q_2$ and $Q_3$ are each —O—, X is a single bond, Y is

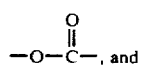

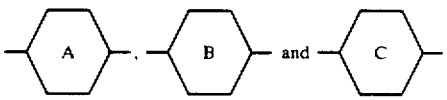

are each

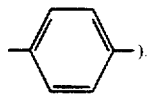

i) Production of (2S,3S)-3-butoxy-2-butanol 4.00 g of (2S,3S)-(+)-2,3-butanediol and 4.04 g of n-butyl aldehyde were subjected to the same procedure as in Example 1 i) to obtain 4.14 g of (2S,3S)-3-butoxy-2-butanol (b.p. 68–71° C./33 mmHg). The $^1$H-NMR and IR spectrum of this compound were completely agreed with those of (2R,3R)-3-butoxy-2-butanol.

ii) Condensation 0.35 g of the (2S,3S)-butoxy-2-butanol produced in the above i) and 1.00 g of 4'-octyloxy-4-biphenyl ester of 4-hydroxybenzoic acid were subjected to the same procedure as in Example 3 ii) to obtain 0.63 g of the title compound.

The elementary analysis and specific rotatory power of the compound are shown below.

Elementary analysis
Calcd. for $C_{35}H_{48}O_5$: C, 76.89; H, 8.48;
Found C, 76.89; H, 8.53.
$[\alpha]^{25}_D$: −6.60° (c=1.03, chloroform)

EXAMPLE 28

Production of 4'-octyloxy-4-biphenyl ester of 4-[(1S,2S)-2-butoxy-1-methylpropoxy]benzoic acid (a compound of the general formula [I'] in which n is 0, $R_1$ is $C_8H_{17}$, $R_2$ and $R_3$ are each $CH_3$, $R_4$ is n-$C_4H_9$, $Q_1$, $Q_2$ and $Q_3$ are each —O—, X is a single bond, Y is

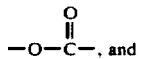

41

-continued

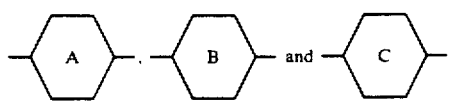

are each

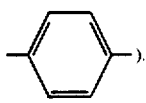

i) Production of (2R, 3S)-3-butoxy-2-butanol

This optically active alcohol was produced by subjecting the (2S,3S)-3-butoxy-2-butanol produced in Example 27 i) to the inversion of hydroxyl group in the same manner as in Example b 3 i).

The title alcohol can also be produced from (2R,3R)-(−)-2,3-butanediol in the following scheme.

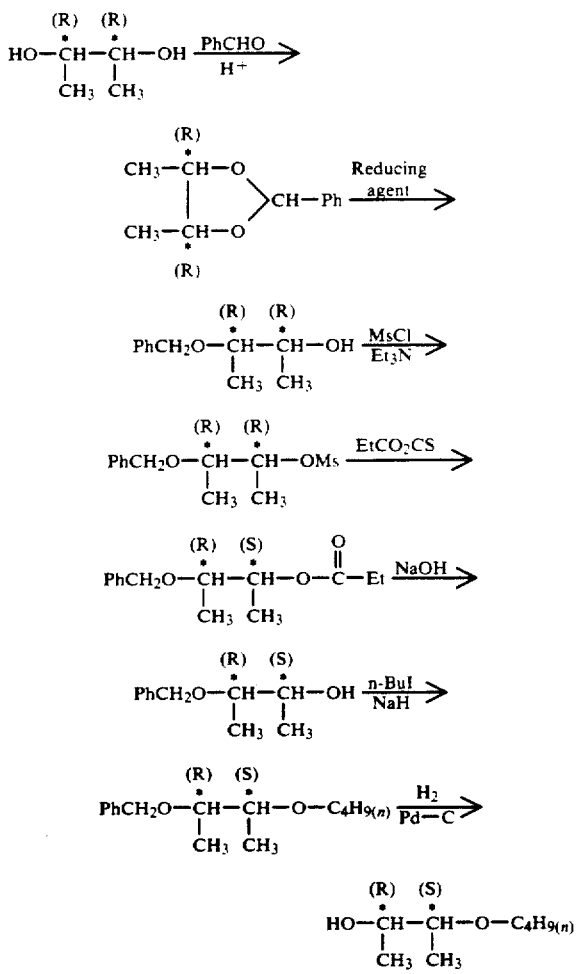

That is, 5.15 g of (2R,3R)-(−)-2,3-butanediol and 6.06 g of benzaldehyde were dissolved in 100 ml of benzene. Thereto was added 0.23 g of p-toluenesulfonic acid monohydrate. The mixture was refluxed for 3 hours with dehydrating according to a conventional method. After the completion of the reaction, 0.1 ml of pyridine was added. The solvent was removed by distillation under reduced pressure. The residue was subjected to

42 distillation under reduced pressure (b.p. 56°-59° C./mmHg) to obtain 9.87 g of a benzylidene compound.

13.87 g of aluminum chloride was dissolved in 100 ml of dry ether with ice cooling. Thereto was added 0.99 g of lithium aluminum hydride in small portions. Thereto was dropwise added 9.27 g of the above obtained benzylidene compound with ice cooling. The mixture was stirred overnight at room temperature. After the completion of the reaction, 100 ml of 10% sulfuric acid was added with stirring under ice cooling. The ether layer was separated and the aqueous layer was extracted with ether twice. The combined ether layer was dried and concentrated. The concentrate was subjected to distillation under reduced pressure (b.p. 72°-74° C./1 mmHg) to obtain 9.03 g of (2R,3R)-3-benzyloxy-2-butanol.

In 30 ml of dichloromethane were dissolved 3.00 g of (2R,3R)-3-benzyloxy-2-butanol and 2.19 g of triethylamine. Thereto was dropwise added 2.48 g of methanesulfonyl chloride with stirring under ice cooling. The mixture was stirred for 3 hours at room temperature. The mixture was poured into water. The resulting dichloromethane layer was separated. The aqueous layer was extracted with dichloromethane twice. The combined dichloromethane solution was washed with dilute hydrochloric acid and an aqueous sodium bicarbonate solution in this order, dried and concentrated. The residue was subjected to column chromatography (silica gel, developing solvent=dichloromethane) to obtain 4.14 g of oily (2R,3R)-3-benzyloxy-2-butyl ester of methanesulfonic acid.

10.85 g of cesium carbonate was dissolved in 200 ml of methanol. 7.41 g of propionic acid was added dropwise. The mixture was stirred for 1 hour at room temperature. Methanol was removed by distillation. The residue was mixed with toluene and subjected to distillation to remove toluene (100 ml×three times), whereby a white powder of cesium propionate was obtained. This powder and 4.07 g of the above obtained (2R,3R)-3- benzyloxy-2-butyl ester of methanesulfonic acid were dissolved in 120 ml of dry N,N-dimethylformamide. The mixture was heated at 100° C. overnight. After the completion of the reaction, the mixture was poured into water and extracted with ether three times. The extract was washed with water (two times), dilute hydrochloric acid (once) and an aqueous sodium bicarbonate solution (once) in this order, dried and concentrated. The residue was subjected to Kugel-rohr distillation (1 mmHg) to obtain 2.81 g of (2S,3R)-3-benzyloxy-2-butyl ester of propionic acid.

2.70 g of (2S,3R)-3-benzyloxy-2-butyl ester of propionic acid was dissolved in 40 ml of methanol. Thereto was added 14 ml of a 1 N solution of sodium hydroxide in methanol. The mixture was stirred overnight at room temperature. After the completion of the reaction, methanol was removed by distillation. The residue was diluted with water and extracted with dichloromethane three times. The extract was dried and concentrated. The residue was subjected to Kugel-rohr distillation (1 mmHg) to obtain 2.00 g of (2S,3R)-3-benzyloxy-2-butanol.

1.90 g of (2S,3R)-3-benzyloxy-2-butanol was dissolved in 50 ml of dry N,N-dimethylformamide. Thereto was added in small portions 2.53 g of about 60% oily sodium hydride. The mixture was stirred for 1 hour at room temperature. 11.63 g of butyl iodide was dropped with ice cooling. The mixture was stirred overnight at room temperature. The reaction mixture was poured into water. The resulting mixture was extracted with ether three times. The extract was washed with water three times, dried and concentrated. The residue was subjected to Kugel-rohr distillation (1 mmHg) to obtain 2.05 g of (2R,3S)-2-benzyloxy-3butoxybutane.

1.94 g of (2R,3S)-2-benzyloxy-3-butoxybutane was dissolved in a mixture of 80 ml of ethanol and 8 ml of 2 N hydrochloric acid. Thereto was added 200 mg of 5% palladium carbon. The mixture was subjected to hydrogenation at the atmospheric pressure at room temperature. After the completion of the reaction, the catalyst was removed by filtration and the filtrate was subjected to distillation. The residue was diluted with water and extracted with dichloromethane three times. The extract was dried and concentrated. The residue was subjected to Kugel-rohr distillation (30 mmHg) to obtain 0.76 g of (2R,3S)-3-butoxy-2-butanol. The $^1$H-NMR and IR spectrum of this compound were completely agreed with those of (2S,3R)-3-butoxy-2-butanol.

ii) Condensation 0.35 g of the (2R,3S)-3-butoxy-2-butanol produced in the above i) and 1.00 g of 4'-octyloxy-4-biphenyl ester of 4-hydroxybenzoic acid were subjected to the same procedure as in Example 3 ii) to obtain 0.91 g of the title compound.

The elementary analysis and specific rotatory power of the compound are shown below.
Elementary analysis
Calcd. for $C_{35}H_{46}O_5$: C, 76.89; H, 8.48;
$[\alpha]^{24}_D$: 0 (c = 1.03, chloroform)

TEST EXAMPLES 1–28

The optically active compounds produced in Examples 1–28 were measured for phases, phase transition temperatures and spontaneous polarization. The results of these measurements are shown in Table 1.

Incidentally, the measurements of phases and phase transition temperatures were determined by using a polarizing microscope and DSC (differential scanning calorimetry).

The measurement of spontaneous polarization was conducted in accordance with the above mentioned Sowyer-Tower method. The spontaneous polarization is a value at a temperature which is 10° C. lower than the upper limit of chiral smectic C phase.

In Table 1, each phase (each liquid crystal phase, etc.) was expressed in the following abbreviation form.
Iso: Isotropic liquid phase
$S_A$: Smectic A phase
Sc*: Chiral smectic C phase
$S_1$, $S_2$: Smectic phase which is not identified.
Ch: Cholesteric phase
K: Crystalline phase

TABLE 1

| Test No. | Optically active compound*1 R$_4$ | Q$_1$ | Q$_2$ | Q$_3$ | M | Example No. | Phases and phase transition temperatures | Spontaneous polarization (nC/cm$^2$) |
|---|---|---|---|---|---|---|---|---|
| 1 | —C$_4$H$_9$, | —O—, | O=C—O—, | —O—, | (structure) | 1(1R, 2R) | Iso ⇌ 147 S$_A$ ⇌ 113 Sc* ⇌ K | 3.5 |
| 2 | —C$_4$H$_9$, | —O—, | O=C—O—, | —O—, | (structure) | 2(1S, 2R) | Iso ⇌ 143 S$_A$ ⇌ 115 Sc* ⇌ 82 K | 27 |
| 3 | —C$_2$H$_5$, | —O—, | O=C—O—, | O=C—O—, | (structure) | 9 | Iso ⇌ 143 S$_A$ ⇌ 109 Sc* ⇌ 90 K | 27 |
| 4 | —C$_4$H$_9$, | —O—, | O=C—O—, | O=C—O—, | (structure) | 10 | Iso ⇌ 126 S$_A$ ⇌ 93 Sc* ⇌ 76 K | 14.5 |
| 5 | —C$_4$H$_9$, | —O—, | —O—, | —O—, | (structure) | 5 | Iso ⇌ 145 S$_A$ ⇌ 101 Sc* ⇌ 67 K, S$_1$ | 21 |
| 6 | —C$_4$H$_9$, | —O—, | —O—, | —O—, | (structure) | 3(1R, 2R) | Iso ⇌ 94 Ch ⇌ 86 Sc* ⇌ 76 K | 68 |
| 7 | —C$_4$H$_9$, | —O—, | —O—, | —O—, | (structure) | 4(1S, 2R) | Iso ⇌ 113 Ch ⇌ 88 Sc* ⇌ 73 K | 27 |
| 8 | —C$_8$H$_{17}$, | —O—, | —O—, | —O—, | (structure) | 8 | Iso ⇌ 101 Ch ⇌ 83 Sc* ⇌ 64 K | 33 |

TABLE 1-continued

| Test No. | Optically active compound*1 | | | | | | Measurements | |
|---|---|---|---|---|---|---|---|---|
| | $R_4$ | $Q_1$ | $Q_2$ | $Q_3$ | M | Example No. | Phases and phase transition temperatures | Spontaneous polarization (nC/cm²) |
| 9 | $-C_4H_9$ | $-O-$ | $-O-$ | $-O-$ | (biphenyl–COO–phenyl) | 6 | Iso ⇌(112) $S_A$ ⇌(91) $Sc^*$ ⇌(53) $S_1$ → $S_2$ → K | 45 |
| 10 | $-C_4H_9$ | $-O-$ | $-O-$ | $-O-$ | (biphenyl–COO–phenyl) | 7 | Iso ⇌(120) Ch ⇌(90) $Sc^*$ ⇌(65) $S_1$ ⇌(57) K | 26 |
| 11 | $-C_4H_9$ | $-O-$ | $-O-$ | $-O-$ | (phenyl–COO–biphenyl) | 27 | Iso ⇌(114.5/89.7) Ch ⇌(53.9) $Sc^*$ ⇌(86.4) K | 44 |
| 12 | $-CH_3$ | $-O-$ | $-O-$ | $-O-$ | (phenyl–COO–biphenyl) | 11 | Iso ⇌(178/163) Ch ⇌(165) $S_A$ ⇌(136) $Sc^*$ ⇌(57) $S_1$ → (50) K | 21 |
| 13 | $-C_4H_9$ | $-O-$ | $-O-$ | $-O-$ | (phenyl–COO–biphenyl) | 15 | Iso ⇌(163) Ch ⇌(161) $S_A$ ⇌(127) $Sc^*$ ⇌(61) $S_1$ → $S_2$ → K | 30 |
| 14 | $-CH_3$ | $-O-$ | $-O-$ | $-O-$ | (phenyl–COO–biphenyl) | 13 | Iso ⇌(159) Ch ⇌(112) $Sc^*$ ⇌(74) $S_1$ → K | 44 |
| 15 | $-C_4H_9$ | $-O-$ | $-O-$ | $-O-$ | (biphenyl–COO–phenyl) | 17 | Iso ⇌(151) Ch ⇌(119) $Sc^*$ ⇌(70) $S_1$ → K | 44 |

TABLE 1-continued

| Test No. | Optically active compound*[1] | | | | | Example No. | Measurements | Spontaneous polarization ($nC/cm^2$) |
|---|---|---|---|---|---|---|---|---|
| | $R_4$ | $Q_1$ | $Q_2$ | $Q_3$ | M | | Phases and phase transition temperatures | |
| 16 | —$CH_3$, | —O—, | —O—, | —O—, | [biphenyl-C(=O)O-phenyl] | 12 | Iso ⇌157 Ch ⇌120 Sc* ⇌94 K | 11 |
| 17 | —$C_4H_9$, | —O—, | —O—, | —O—, | [biphenyl-C(=O)O-phenyl] | 16 | Iso ⇌145 Ch ⇌121 Sc* ⇌98 K | 26 |
| 18 | —$CH_3$, | —O—, | —O—, | —O—, | [biphenyl-C(=O)O-phenyl] | 14 | Iso ⇌155 Ch ⇌118 Sc* ⇌46 K, $S_1$ | 57 |
| 19 | —$C_4H_9$, | —O—, | —O—, | —O—, | [biphenyl-C(=O)O-phenyl] | 18 | Iso ⇌145 Ch ⇌123 Sc* ⇌75 K | 45 |
| 20 | —$C_2H_5$, | —O—, | —O—, | —O—, | [biphenyl-C(=O)O-phenyl] | 24 | Iso ⇌153 Ch ⇌121 Sc* ⇌74 K, $S_1$ | 73 |
| 21 | —$C_4H_9$, | —O—, | —O—C(=O)—, | —O—, | [biphenyl] | 19 | Iso ⇌58 K | Not available |
| 22 | —$C_4H_9$, | —O—, | —O—, | —O—, | [biphenyl] | 20 | Iso ⇌33 K | Not available |
| 23 | —$C_4H_9$, | —O—, | —O—C(=O)—, | —C(=O)—O—, | [biphenyl] | 21 | Iso ⇌45 K | Not available |

TABLE 1-continued

| Test No. | Optically active compound*1 | | | | | Measurements | |
|---|---|---|---|---|---|---|---|
| | R₄ | Q₁ | Q₂ | Q₃ | M | Example No. / Phases and phase transition temperatures | Spontaneous polarization (nC/cm²) |
| 24 | —C₄H₉ | —O— | O=C / —O—C— | —O— | biphenyl | 22; Iso ⇌(41) Ch ⇌(36) Sc* ⇌(30) K | 30 |
| 25 | —C₄H₉ | —O— | O=C / —O—C— | —O— | biphenyl | 23; Iso ⇌(49) Ch ⇌(46) Sc* ⇌(41) K, S₁ | Not available |
| 26 | —C₂H₅ | —O— | O=C / —O—C— | —O— | terphenyl ester | 25; Iso ⇌(163.4/135.3) Ch ⇌(117.3) K | Not available |
| 27 | —C₂H₅ | — | O=C / —O—C— | —O— | terphenyl ester | 26; Iso ⇌(128.8/101.1) Ch ⇌(64.7/76.0) Sc* ⇌ K | 36 |
| 28 | —C₄H₉ | —O— | O=C / —O—C— | —O— | biphenyl ester | 28; Iso ⇌(41.3) Ch ⇌(83.8) Sc* ⇌(64.7/76.0) K | Not available |

*¹Compound represented by the general formula n-C₈H₁₇—Q₁—M—Q₂—CH—CH—Q₃—R₄
                   |    |
                   CH₃  CH₃

EXAMPLES 29-90

The compounds of Examples 29-90 were produced by a similar procedure as that described previously. Example Nos., structural formulae, phases, phase transition temperatures and elementary analyses of these compounds are shown in Table 2. As to the compounds containing a dichiral side chain component whose production has not been explained above (these compounds are given with a * mark in Table 2), the production of such a component is described in Reference Examples 1-5 which appear after Table 2. Incidentally, the structural formulae of compounds whose elementary analyses are not given in Table 2 were determined based on various spectral data.

TABLE 2

| Example No. | Structural formula | Phases and Phase transition temperatures (°C) | Spontaneous polarization (nC/cm²) | Elementary analysis (Compositional formula, calculated value and observed value) |
|---|---|---|---|---|
| 29 | n-C₈H₁₇—⟨O⟩—⟨O⟩—C(=O)—O—CH(S)(CH₃)—CH(R)(CH₃)—O—C₆H₁₃(*1) | K ⇌(54.2/65.6) Sc* ⇌(85.6) Ch ⇌(107.6) Iso | 43 | C₃₇H₅₈O₃: C, 77.31; H, 8.77. C, 77.57; H, 8.88. |
| 30 | n-C₈H₁₇O—⟨O⟩—⟨O⟩—C(=O)—O—CH(R)(CH₃)—CH(S)(CH₃)—OPr | K ⇌(53.7/84.1) Sc* ⇌(126.3) Ch ⇌(150.5) Iso | 29 | C₃₅H₄₄O₆: C, 74.97; H, 7.91. C, 74.98; H, 7.69. |
| 31 | n-C₈H₁₇O—⟨O⟩—⟨O⟩—C(=O)—O—CH(R)(CH₃)—CH(S)(CH₃)—OBu(n) | K ⇌(33.5/37.5) Sc* ⇌(46.3) Ch ⇌(50.2) Iso | 92 | C₂₈H₄₀O₄: C, 76.33; H, 9.15. C, 76.04; H, 9.17. |
| 32 | n-C₈H₁₇—⟨O⟩—⟨O⟩—C(=O)—O—CH(R)(CH₃)—CH(S)(CH₃)—OPr | K ⇌(25.6/53.0) Sc* ⇌(56.2) Ch ⇌(81.3) Iso | 42 | C₃₅H₄₆O₄: C, 79.21; H, 8.74. C, 79.33; H, 8.78. |
| 33 | n-C₁₄H₂₉O—⟨O⟩—⟨O⟩—C(=O)—O—CH(R)(CH₃)—CH(S)(CH₃)—OPr | K ⇌(64.4/72.5) Sc* ⇌(124.1) Ch ⇌(137.1) Iso | 48 | C₄₁H₅₆O₆: C, 76.36; H, 8.75. C, 76.22; H, 8.73. |
| 34 | n-C₈H₁₇O—⟨O⟩—⟨O⟩—C(=O)—O—CH(S)(CH₃)—CH(R)(CH₃)—OPr | k ⇌(7.9) S₁ ⇌(21.3) Iso; −8 ~ −26 | — | C₂₉H₄₂O₅: C, 74.33; H, 8.60. C, 74.62; H, 8.87. |
| 35 | n-C₈H₁₇O—⟨O⟩—⟨O⟩—CH₂—O—C(=O)—CH(R)(CH₃)—CH(S)(CH₃)—OCH₃ | K ⇌(21.8/55.2) S₂ ⇌(49.3/62.6) S₁ ⇌(85.7) Sc* ⇌(127.3) S_A ⇌(131.7) Iso | 32.5 | C₃₃H₄₂O₅: C, 76.42; H, 8.16. C, 76.37; H, 8.04. |
| 36 | n-C₁₀H₂₁O—⟨O⟩—⟨O⟩—C(=O)—O—CH(R)(CH₃)—CH(S)(CH₃)—OCH₃ | K ⇌(37.0) Sc* ⇌(46.3) S_A ⇌(52.2) Iso | 46.4 | C₂₈H₄₀O₄: C, 76.33; H, 9.15. C, 76.11; H, 9.20. |

TABLE 2-continued

| Example No. | Structural formula | Phases and Phase transition temperatures (°C) | Spontaneous polarization (nC/cm²) | Elementary analysis (Compositional formula, calculated value and observed value) |
|---|---|---|---|---|
| 37 | n-C₈H₁₇O–⟨⟩–⟨⟩–O–C(=O)–CH(S)(CH₃)–CH(S)(CH₃)–OCH₃ (*2) | K ⇌(23.5/31.8) Sc* ⇌(32.6) Ch ⇌(33.0/38.6–42) Iso | 8 | C₂₆H₃₆O₄: C, 75.69; H, 8.80. C, 75.83; H, 8.86. |
| 38 | n-C₈H₁₇O–⟨⟩–⟨⟩–O–C(=O)–CH(S)(CH₃)–CH(CH₃)–OCH₃ (*2) | K ⇌(85.1/99.1) Sc* ⇌(116.0) Ch ⇌(151.1) Iso | 8 (−15° C.) | C₂₇H₄₀O₆: C, 74.41; H, 7.57. C, 74.47; H, 7.54. |
| 39 | n-C₈H₁₇O–⟨⟩–⟨⟩–C(=O)O–⟨⟩(N≡C)–O–CH(S)(CH₃)–CH(R)(CH₃)–OBu(n) | K ⇌(57.9) S₂ ⇌(59.5) S₁ ⇌(98.0) Sc* ⇌(104.1) Iso; S₄ ⇌(54.7/113.7) Iso | — | C₃₄H₄₅O₅: C, 74.56; H, 8.28; N, 2.56. C, 74.64; H, 8.31; N, 2.25. |
| 40 | n-C₁₂H₂₅O–⟨⟩–⟨⟩–O–C(=O)–CH(R)(CH₃)–CH(S)(CH₃)–OCH₃ | K ⇌(47.4/47.4) Sc* ⇌(54.7) Iso | — | C₃₀H₄₄O₄: C, 76.88; H, 9.46. C, 76.64; H, 9.51. |
| 41 | n-C₈H₁₇O–⟨⟩–⟨⟩–O–CH(R)(CH₃)–CH(R)(CH₃)–OBu(n) | K ⇌(−18.3) Iso | — | C₂₉H₄₂O₄: C, 76.61; H, 9.31. C, 76.97; H, 9.48. |
| 42 | ⟨⟩–C(=O)O–⟨⟩–O–CH(S)(CH₃)–CH(R)(CH₃)–OBu(n) | K ⇌(18.4/30.3) Iso | — | C₂₉H₄₂O₅: C, 74.01; H, 8.99. C, 73.99; H, 9.02. |
| 43 | n-C₅H₁₁–⟨cyclohexyl⟩–⟨⟩–C(=O)O–⟨⟩–O–C(=O)–CH(R)(CH₃)–CH(CH₃)–OBu(n) | K ⇌(64.2) S₁ ⇌(69.6) S₂ ⇌(87.7/78.3–87.5) Iso | — | C₃₂H₄₆O₅: C, 80.29; H, 9.69. C, 80.17; H, 9.57. |
| 44 | n-C₈H₁₇O–⟨⟩–⟨⟩–CH₂O–⟨⟩–O–CH(S)(CH₃)–CH(R)(CH₃)–OBu(n) | K ⇌(26.6/52.3) S₁ ⇌(56.4) Sc* ⇌(110.3) Iso | 34.5 | C₃₅H₄₈O₄: C, 78.91; H, 9.08. C, 79.22; H, 9.14. |

TABLE 2-continued

| Example No. | Structural formula | Phases and Phase transition temperatures (°C.) | Spontaneous polarization (nC/cm²) | Elementary analysis (Compositional formula, calculated value and observed value) |
|---|---|---|---|---|
| 45 | n-C₈H₁₇O—⌬—⌬—CH₂O—⌬—O—C(=O)—CH(R)—CH(S)—OCH₃ with CH₃, CH₃ | K ⇌(51.4/76.7) S₂ ⇌(90.8/95.1) S₁ ⇌(106.1/—) ; Sc* ⇌(—/137.0) Iso | 38 | C₃₁H₄₂O₅: C, 76.42; H, 8.16. C, 76.30; H, 8.19. |
| 46 | n-C₈H₁₇O—⌬—⌬—O—C(=O)—CH(S)—CH(S)—OCH₃(*1) with Et, CH₃ | K ⇌(29.2/75.0) Sc* ⇌(64.2/77.2) Ch ⇌(85.0-97.0) Iso | small | C₃₄H₄₂O₆: C, 74.70; H, 7.74. C, 74.53; H, 7.65. |
| 47 | n-C₈H₁₇O—⌬—⌬—O—CH₂—⌬—O—CH(S)—CH(R)—OBu(n) with CH₃, CH₃ | K ⇌(95.9/—) Sc* ⇌(104.1/—) Iso | 28 (99° C.) | C₃₅H₄₈O₄: C, 78.91; H, 9.08. C, 79.05; H, 9.14. |
| 48 | ⌬—⌬—O—C(=O)—⌬—O—CH(S)—CH(S)—OPr(*2) with CH₃, CH₃ | K ⇌(8.0/90.5) Sc* ⇌(13.0/—) S₄ ⇌(21.3/112.8) Iso; CH ⇌(54.5/—) | — | C₂₈H₄₀O₄: C, 76.33; H, 9.15. C, 76.38; H, 9.28. |
| 49 | n-C₈H₁₇O—⌬—⌬—O—C(=O)—⌬—O—CH(R)—CH(R)—OBu(n) with CH₃, CH₃ | K ⇌(11.3/54.8) S₂ ⇌(22.6/—) S₁ ⇌(35.2/—) Sc* ⇌(↓/—) Iso | 35.6 | C₃₅H₄₆O₅: C, 76.89; H, 8.48. C, 76.98; H, 8.51. |
| 50 | n-C₈H₁₇O—⌬—⌬—O—C(=O)—⌬—O—CH(R)—CH—OBu(n) with CH₃ | K ⇌(13.7/54.9) Sc* ⇌(77.7/—) Iso | — | C₃₅H₄₆O₆: C, 76.89; H, 8.48. C, 77.00; H, 8.54. |
| 51 | n-C₈H₁₇O—⌬—⌬—O—C(=O)—⌬—O—CH(S)—CH—OBu(n) with CH₃ | K ⇌(13.6/54.5) Sc* ⇌(77.2/—) Iso | small | C₃₅H₄₆O₅: C, 76.89; H, 8.48. C, 76.72; H, 8.47. |
| 52 | n-C₆H₁₃O—⌬—⌬—O—C(=O)—⌬—O—CH(R)—CH(S)—OCH₃ with CH₃, CH₃ | K ⇌(39.6/42.4) Sc* ⇌(46.2/—) Ch ⇌(46.9/—) Iso | 156 (42° C.) | C₂₄H₃₂O₄: C, 74.97; H, 8.39. C, 75.06; H, 8.41. |

TABLE 2-continued

| Example No. | Structural formula | Phases and Phase transition temperatures (°C.) | Spontaneous polarization (nC/cm²) | Elementary analysis (Compositional formula, calculated value and observed value) |
|---|---|---|---|---|
| 53 | n-C₇H₁₅O–⟨⟩–⟨⟩–O–C(=O)–CH(R)–CH(S)(CH₃)–OCH₃ with CH₃ | K ⇌(26.0/19.4) S₁ ⇌(28.2) Sc* ⇌(42.8) Ch ⇌(43.3) Iso | 110 (40° C.) | C₂₅H₃₄O₄: C, 75.34; H, 8.60. C, 75.41; H, 8.63. |
| 54 | n-C₆H₁₃O–⟨⟩–⟨⟩–O–C(=O)–CH(R)–CH(S)(CH₃)–OBu(n) with CH₃ | K ⇌(26.3/48.8) Sc* ⇌(43.7) Ch ⇌(48.8) Iso | 78.8 (38° C.) | C₂₇H₃₈O₄: C, 76.02; H, 8.98. C, 76.25; H, 9.08. |
| 55 | n-C₇H₁₅O–⟨⟩–⟨⟩–O–C(=O)–CH(R)–CH(S)(CH₃)–OBu(n) with CH₃ | K ⇌(−21.0/38.0) Sc* ⇌(41.6) Ch ⇌(44.5) Iso | 82 | C₂₈H₄₀O₄: C, 76.33; H, 9.15. C, 76.17; H, 9.18. |
| 56 | n-C₈H₁₇C(=O)O–⟨⟩–⟨⟩–O–CH(S)–CH(R)(CH₃)–OBu(n) with CH₃ | K ⇌(28.2/40.4) Iso | — | C₂₉H₄₂O₄: C, 76.61; H, 9.31. C, 76.43; H, 9.27. |
| 57 | n-C₅H₁₁O–⟨⟩–⟨⟩–O–C(=O)–CH(S)–CH(R)(CH₃)–OCH₃ with CH₃ | K ⇌(43.7/50.3) Iso | — | C₂₃H₃₀O₄: C, 74.56; H, 8.16. C, 74.67; H, 8.03. |
| 58 | n-C₈H₁₇C(=O)O–⟨⟩–⟨⟩–O–C(=O)–CH(R)–CH(S)(CH₃)–OCH₃ with CH₃ | K ⇌(35.9/37.5) Sc* ⇌(46.9) Iso | 111 | C₂₇H₃₆O₄: C, 73.61; H, 8.24. C, 73.84; H, 8.35. |
| 59 | n-C₆H₁₃O–⟨⟩–⟨⟩–O–C(=O)–CH(S)–CH(CH₃)–OCH₃(*²) with CH₃ | K ⇌(33.2) Iso | — | C₂₄H₃₂O₄: C, 74.97; H, 8.39. C, 74.73; H, 8.45. |

TABLE 2-continued

| Example No. | Structural formula | Phases and Phase transition temperatures (°C) | Spontaneous polarization (nC/cm²) | Elementary analysis (Compositional formula, calculated value and observed value) |
|---|---|---|---|---|
| 60 | n-C₉H₁₉O—⟨phenyl⟩—⟨phenyl⟩—O—C(=O)—CH(R)—CH(S)—OBu(n) with CH₃, CH₃ | K ⇌ 36.3/42.2 Sc* ⇌ 51.2 Ch ⇌ 52.4 Iso | 60 | C₂₉H₄₄O₄: C, 76.27; H, 9.71. C, 76.31; H, 9.36. |
| 61 | n-C₈H₁₇C(=O)—⟨phenyl⟩—⟨phenyl⟩—O—C(=O)—CH(R)—CH(S)—OBu(n) with CH₃, CH₃ | K ⇌ 35.2/46.6 S₂ ⇌ 38.1 Sc* ⇌ 56.2 S₁ 49.0 Iso | 25 (−6° C.) | C₃₀H₄₂O₅: C, 74.65; H, 8.77. C, 74.40; H, 8.48. |
| 62 | n-C₈H₁₇C(=O)—⟨phenyl⟩—⟨phenyl⟩—O—C(=O)—CH(R)—CH(S)—OCH₃ with CH₃, CH₃ | K ⇌ 77.8/84.7 Iso | — | C₂₇H₃₆O₅: C, 76.45; H, 8.55. C, 76.50; H, 8.70. |
| 63 | n-C₉H₁₉O—C(=O)—⟨phenyl⟩—⟨phenyl⟩—O—C(=O)—CH(R)—CH(S)—OCH₃ with CH₃, CH₃ | K ⇌ 0.4/23.7 Iso | — | C₂₇H₃₆O₅: C, 73.61; H, 8.24. C, 73.83; H, 8.21. |
| 64 | n-C₉H₁₉—⟨phenyl⟩—⟨phenyl⟩—O—C(=O)—CH(R)—CH(S)—OCH₃ with CH₃, CH₃ | K ⇌ −7.4/31.2 Sc* ⇌ 13.4 S₄ ⇌ 20.8 Iso | 90 | C₂₇H₃₈O₃: C, 78.98; H, 9.33. C, 79.01; H, 9.35. |
| 65 | n-C₈H₁₇O—⟨phenyl⟩—⟨phenyl⟩—O—C(=O)—CH(R)—CH(S)—OCH₃ with CH₃, CH₃ | K ⇌ 0.3/36.8 Sc* ⇌ 10.5 Ch ⇌ 19.5 Iso | 78 (−5° C.) | C₂₇H₃₈O₆: C, 71.03; H, 7.95. C, 71.13; H, 8.09. |
| 66 | n-C₆H₁₃—⟨phenyl⟩—⟨phenyl⟩—O—C(=O)—CH(R)—CH(S)—OC₃H₇ with CH₃, CH₃ | K ⇌ 22.9/53.2 S₂ ⇌ 27.9 S₁ ⇌ 37.6 Sc* 35.4 Ch 56.8 Iso | 96 | |
| 67 | n-C₈H₁₇O—⟨phenyl⟩—⟨phenyl⟩—O—C(=O)—CH(R)—CH(S)—OCH₃(*4) with Et, CH₃ | K ⇌ 30.5 Iso | — | C₂₇H₃₈O₄: C, 76.02; H, 8.98. C, 75.98; H, 9.17. |

TABLE 2-continued

| Example No. | Structural formula | Phases and Phase transition temperatures (°C.) | Spontaneous polarization (nC/cm²) | Elementary analysis (Compositional formula, calculated value and observed value) |
|---|---|---|---|---|
| 68 | n-C₉H₁₉—C(=O)—O—⟨phenyl⟩—⟨phenyl⟩—O—C(=O)—CH(R)—CH(S)—OCH₃ with CH₃, CH₃ | K ⇌(44.0) Sc* ⇌(52.0) Iso | 78 (−5° C.) | C₂₈H₃₈O₅: C, 73.98; H, 8.43. C, 74.01; H, 8.54. |
| 69 | n-C₇H₁₅—C(=O)—O—⟨phenyl⟩—⟨phenyl⟩—O—C(=O)—CH(R)—CH(S)—OCH₃ with CH₃, CH₃ | K ⇌(31.9/36.9) Sc* ⇌(45.5) Iso | 119 | C₂₆H₃₄O₅: C, 73.21; H, 8.03. C, 73.25; H, 8.18. |
| 70 | n-C₆H₁₃—C(=O)—O—⟨phenyl⟩—⟨phenyl⟩—O—C(=O)—CH(R)—CH(S)—OCH₃ with CH₃, CH₃ | K ⇌(16.2/23.1) (S₁) ⇌(24.5/35.0) Sc* ⇌(39.0) S₂ ⇌(25.7) S₁ ⇌(31.6) Iso | 143 (−5° C.) | C₂₅H₃₂O₅: C, 72.79; H, 7.82. C, 73.01; H, 7.82. |
| 71 | n-C₇H₁₅—O—⟨phenyl⟩—⟨phenyl⟩—O—C(=O)—CH(R)—CH(S)—OC₃H₇ with CH₃, CH₃ | K ⇌(20.6/27.2) Sc* ⇌(58.0) Iso | 63 | C₂₇H₃₈O₄: C, 76.02; H, 8.98. C, 76.36; H, 8.94. |
| 72 | n-C₈H₁₇—C(=O)—O—⟨phenyl⟩—⟨phenyl⟩—O—C(=O)—CH(R)—CH(S)—OC₃H₇ with CH₃, CH₃ | K ⇌(22.7/32.0) S₁ ⇌(50.0) Sc* ⇌(58-64) Iso | 42 | |
| 73 | n-C₈H₁₇—O—⟨phenyl⟩—C(=O)—O—⟨phenyl⟩—O—C(=O)—CH(R)—CH(S)—OCH₃ with CH₃, CH₃ | K ⇌(34.5) Iso | — | C₂₇H₃₆O₆: C, 71.03; H, 7.95. C, 71.22; H, 8.05. |
| 74 | n-C₈H₁₇O—⟨pyrimidine⟩—⟨phenyl⟩—O—C(=O)—CH(R)—CH(S)—OCH₃ with CH₃, CH₃ | K ⇌(6.8) Sc* ⇌(27.0) Ch ⇌(35.6) Iso; 48 51.6 | 131 | C₂₄H₃₄N₂O₄: C, 69.54; H, 8.27; N, 6.76. C, 69.82; H, 8.37; N, 6.79. |

TABLE 2-continued

| Example No. | Structural formula | Phases and Phase transition temperatures (°C.) | Spontaneous polarization (nC/cm²) | Elementary analysis (Compositional formula, calculated value and observed value) |
|---|---|---|---|---|
| 75 | n-C₈H₁₇O—[pyridine]—[pyridine]—O—C(=O)—CH(R)—CH(S)—OC₃H₇ with CH₃, CH₃ | K ⇌(−2.0/6.4) Sc* ⇌(35.0) S₁ ⇌(43.3) → Ch →(49.5) Iso | 54.5 | — |
| 76 | n-C₈H₁₇O—[pyridine]—[pyridine]—O—C(=O)—CH(R)—CH(S)—OBu(n) with CH₃, CH₃ | K ⇌(21.1/45.6) Sc* ⇌(28.2) Ch ⇌(41.6) Iso | 49.2 (−5° C.) | C₂₇H₄₀N₂O₄: C, 71.02; H, 8.83; N, 6.13. C, 71.31; H, 8.83; N, 6.19. |
| 77 | n-C₈H₁₇—[biphenyl]—O—C(=O)—CH(R)—CH(S)—OC₂H₅ with CH₃, CH₃ | K ⇌(22.0/36.3) Sc* ⇌(26.2) Iso | 55 (6-7° C.) | C₂₇H₁₈O₃: C, 78.98; H, 9.38. C, 78.81; H, 9.42. |
| 78 | n-C₈H₁₇—[phenyl]—C(=O)O—[phenyl]—O—C(=O)—CH(R)—CH(•S)—C₃H₇ with CH₃, OCH₃ | K ⇌(2.7) Sc* ⇌(103.5) Ch ⇌(133.1) Iso | 7.4 | C₃₅H₄₄O₆: C, 74.97; H, 7.91. C, 75.09; H, 7.93. |
| 79 | n-C₈H₁₇O—[biphenyl]—O—C(=O)—CH(R)—CH(•S)—C₃H₇ with CH₃, OCH₃ | K ⇌(8.3/27.7) Sc* ⇌(20.5) Ch ⇌(27.7) Iso | 9.7 (18° C.) | C₂₈H₄₀O₄: C, 76.33; H, 9.15. C, 76.35; H, 9.23. |
| 80 | C₁₀H₂₁C(=O)O—[biphenyl]—O—C(=O)—CH(R)—CH(S)—OCH₃ with CH₃, CH₃ | K ⇌(46.7) Sc* ⇌(54.7) Iso | 61 (−5° C.) | C₂₉H₄₀O₅: C, 74.33; H, 8.60. C, 74.16; H, 8.71. |
| 81 | C₅H₁₁C(=O)O—[biphenyl]—O—C(=O)—CH(R)—CH(S)—OCH₃ with CH₃, CH₃ | K ⇌(−5.0/17.6) S₁ ⇌(40.2) Sc* ⇌(43.4) Iso | 168 (41° C.) | C₂₄H₃₀O₅: C, 72.34; H, 7.59. C, 72.27; H, 7.69. |
| 82 | n-C₈H₁₇—[biphenyl]—O—C(=O)—CH(R)—CH(S)—OC₃H₇ with CH₃, CH₃ | K ⇌(22.8/35.6) Iso | — | C₂₈H₄₀O₃: C, 79.20; H, 9.49. C, 79.37; H, 9.60. |

TABLE 2-continued

| Example No. | Structural formula | Phases and Phase transition temperatures (°C) | Spontaneous polarization (nC/cm²) | Elementary analysis (Compositional formula, calculated value and observed value) |
|---|---|---|---|---|
| 83 | n-C₉H₁₉—⟨benzene⟩—⟨benzene⟩—O—C(=O)—CH(R)—CH(S)—OC₂H₅ with CH₃, CH₃ | K ⇌(−13.2) Sc* ⇌(12.9) S_A ⇌(21.0) Iso; 27.7 | 48.2 | C₂₈H₄₀O₃: C, 79.20; H, 9.49. C, 79.34; H, 9.60. |
| 84 | n-C₆H₁₃—⟨pyrimidine⟩—⟨benzene⟩—O—C(=O)—CH(R)—CH(S)—OCH₃ with CH₃, CH₃ | K ⇌(30.1/41.5) Iso | — | |
| 85 | n-C₇H₁₅—⟨pyrimidine⟩—⟨benzene⟩—O—C(=O)—CH(R)—CH(S)—OCH₃ with CH₃, CH₃ | K ⇌(32.1/54.8) Iso | — | |
| 86 | n-C₈H₁₇—⟨pyrimidine⟩—⟨benzene⟩—O—C(=O)—CH(R)—CH(S)—OCH₃ with CH₃, CH₃ | K ⇌(17.7/50.8) Iso | — | |
| 87 | n-C₈H₁₇—⟨benzene⟩—⟨benzene⟩—O—C(=O)—CH(R)—CH(S)—OCH₃ with CH₃, CH₃ | K ⇌(−18.9) Sc* ⇌(10.3) S_A ⇌(14.6) Iso; 32.2 | 94 | |
| 88 | n-C₈H₁₇—⟨pyrimidine⟩—⟨benzene⟩—O—C(=O)—CH(R)—CH(S)—OC₂H₅ with CH₃, CH₃ | K ⇌(0.3/23.6) Iso | — | C₂₄H₃₄N₂O₃: C, 72.33; H, 8.60; N, 7.03. C, 72.34; H, 8.68; N, 6.98. |
| 89 | n-C₈H₁₇—⟨pyrimidine⟩—⟨benzene⟩—O—CH(R)—CH(S)—OC₃H₇ with CH₃, CH₃ | K ⇌(−12.8) S₂ ⇌(−8.1) S₁ ⇌(−1.9) Iso; 16.1 | — | |

TABLE 2-continued

| Example No. | Structural formula | Phases and Phase transition temperatures (°C) | Spontaneous polarization (nC/cm²) | Elementary analysis (Compositional formula, calculated value and observed value) |
|---|---|---|---|---|
| 90 | 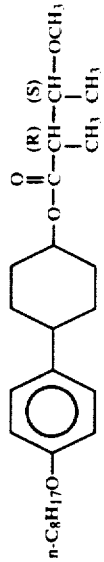 | K ⇌(−6.9) S₂ ⇌(4.6) S₁ ⇌(8.3) Iso; 25.2 | — | C₂₆H₄₂O₄: C, 74.60; H, 10.11. C, 74.78; H, 10.12. |

Note:
—: not available
(a1)See Reference Example 1.
(a2)See Reference Example 2.
(a3)See Reference Example 3.
(a4)See Reference Example 4.
(a5)See Reference Example 5.

EXAMPLES 90A (1)–(6)

These compounds were produced by the procedure similar to that described above. The example Nos., structures, phases, transition temperatures, values of spontaneous polarization and elemental analysis are summarized in the following Table. The chemical structure of Compound of Example No. 96 was determined based on the various spectral data.

TABLE 2a

| Example No. | Structure | Phase Transition Temperature (°C) | Spontaneous Polarization (nC/cm²) | Molecular Formula | Elemental Analysis Calculated Value / Found Value |
|---|---|---|---|---|---|
| 90A(1) | n-C₆H₁₃–⟨phenyl⟩–⟨phenyl⟩–O–C(=O)(R)–*CH(CH₃)–*CH(CH₃)–OCH₃ (S) | K $\xleftrightarrow{5.2}$ Iso | — | $C_{24}H_{32}O_3$ | C, 78.22; H, 8.75. C, 78.44; H, 8.87. |
| 90A(2) | n-C₇H₁₅–⟨phenyl⟩–⟨phenyl⟩–O–C(=O)(R)–*CH(CH₃)–*CH(CH₃)–OCH₃ (S) | $S_1 \xleftrightarrow{-17.8} Sc^* \xleftrightarrow{9.0} S_4 \xleftrightarrow{13.2}$ Iso | 127.0 | $C_{25}H_{34}O_3$ | C, 78.49; H, 8.96. C, 78.48; H, 9.03. |
| 90A(3) | n-C₈H₁₇O–⟨phenyl⟩–⟨cyclohexyl⟩–O–C(=O)(R)–*CH(CH₃)–*CH(CH₃)–OBu(n) (S) | K $\xleftrightarrow{-35.8} S_2 \xleftrightarrow{28.5} S_1 \xleftrightarrow{11.8}$ Iso / $\xleftrightarrow{11.8}$ | — | $C_{29}H_{48}O_4$ | C, 75.61; H, 10.50. C, 75.37; H, 10.62. |
| 90A(4) | n-C₉H₁₉–⟨pyridyl⟩–⟨phenyl⟩–O–C(=O)(R)–*CH(CH₃)–*CH(CH₃)–OCH₃ (S) | K $\xleftrightarrow{20.1}_{60.6}$ Iso | — | $C_{25}H_{36}N_2O_3$ | C, 72.78; H, 8.80. C, 72.68; H, 8.46. |
| 90A(5) | n-C₉H₁₉–⟨pyridyl⟩–⟨phenyl⟩–O–C(=O)(R)–*CH(CH₃)–*CH(CH₃)–OC₂H₅ (S) | K $\xleftrightarrow{10.8}_{30.8}$ Iso | — | $C_{26}H_{38}N_2O_3$ | C, 73.20; H, 8.98. C, 73.31; H, 9.07. |
| 90A(6) | n-C₉H₁₉C(=O)–O–⟨phenyl⟩–⟨phenyl⟩–O–C(=O)(S)–*CH(CH₃)–*CH(CH₃)–OCH₃ (S) | K $\xleftrightarrow{43.3}$ Iso | — | | |

Production of the novel dichiral compounds used in the above Examples is explained in the following Reference Examples.

REFERENCE EXAMPLE 1

Production of (2R, 3R)-3-hexyloxy-2-butanol

The title compound was obtained in the same procedure as in Example 1 i) except that hexyl aldehyde was used in place of n-butyl aldehyde.

REFERENCE EXAMPLE 2

Production of (2R, 3S)-2-methyl-3-propoxybutyric acid

The title compound was obtained by, according to the procedure of Example 15, carrying out etherification using n-propyl iodide in place of n-butyl iodide and then hydrolysis.

REFERENCE EXAMPLE 3

Production of (2S, 3S)-3-methoxy-2-methylbutyric acid

The title compound was produced in accordance with the process described in a literature [G. Frater et al., Tetrahedron, 40, 1269 (1984)]. This compound was converted to a methyl ether compound and then subjected to hydrolysis according to the procedure of Example 11 i) to obtain a corresponding (2S, 3S)-3-methoxy-2-methylbutyric acid. That is, the title compound was produced by using n-methyl iodide in place of n-butyl iodide and then subjected to hydrolysis according to the procedure of Example 15.

REFERENCE EXAMPLE 4

Production of (2S, 3S)-2-ethyl-3-methoxybutyric acid

Similarly to Reference Example 3, the title compound was obtained by employing the process of the literature [G. Frater et al., Tetrahedron, 40, 1269 (1984)] and using ethyl iodide in place of methyl iodide. This compound was converted to a methyl ether compound and then subjected to hydrolysis according to the procedure of Example 11 to obtain a corresponding (2S, 3S)-2-ethyl-3-methoxybutyric acid. Reference Example 5 Production of (2R, 3R)-3-methoxy-2-methylhexanoic acid In accordance with the procedure of Example 9, ethyl ester of 3-oxohexanoic acid as a substrate in place of ethyl ester of 2-methyl-3-oxobutyric acid was subjected to reduction by baker's yeast to obtain ethyl ester of (3R)-3-hydroxyhexanoic acid. This compound was subjected to methylation according to the process of the literature [G. Fráter et al., Tetrahedron, 40, 1269 (1984)] as in Reference Example 3, to obtain ethyl ester of (2R, 3R)-3-hydroxy-2-methylhexanoic acid. This compound was converted to a methyl ether compound and then subjected to hydrolysis in accordance with the procedure of Example 11 to obtain the title compound.

EXAMPLE 91

Production of 4-[(1R, 3R)-3-butoxy-1-methylbutoxycarbonyl]phenyl ester of 4'-octyloxy-4-biphenylcarboxylic acid (a compound of the general formula [I] in which n is 1, $R_1$ is n-$C_8H_{17}$, $R_2$ and $R_3$ are each $CH_3$, $R_4$ is n-$C_4H_9$, $Q_1$ and $Q_3$ are —O—, $Q_2$ and Y are each —C—O—, X is a single bond, and

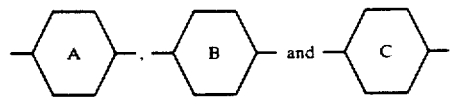

each

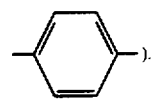

i) Production of (2R, 4R)-4-butoxy-2-pentanol

This optically active alcohol was produced according to the following scheme.

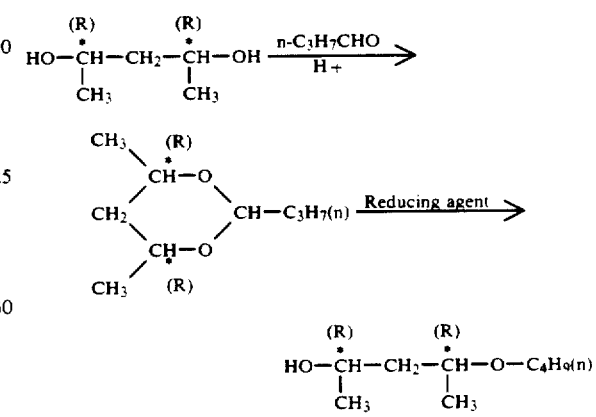

In 50 ml of benzene were dissolved 5.0 g of (2R, 4R)-(−)-2,4-pentanediol and 5.2 g of n-butyl aldehyde. Thereto was added 0.2 g of p-toluenesulfonic acid monohydrate. The mixture was refluxed for 2 hours with removing water, according to a conventional method. After cooling, the reaction mixture was mixed with 80 ml of a 10% aqueous sodium hydrogencarbonate solution. The organic layer was separated, dried and concentrated to obtain 7.7 g of a butylidene form.

12.8 g of aluminum chloride was dissolved in 100 ml of dry ether with ice cooling. Thereto was added 0.9 g of lithium aluminum hydride in small portions. Then, 7.7 g of the butylidene obtained above compound was added with ice cooling. The mixture was stirred overnight at room temperature. To the reaction mixture was added 80 ml of 10% sulfuric acid with stirring under ice cooling. The ether layer was separated and the aqueous layer was extracted with ether twice. The combined ether layer was dried and concentrated. The residue was subjected to column chromatography (Silica gel, developing solvent=chloroform) to obtain 7.10 g of (2R, 4R)-4-butoxy-2-pentanol.

The $^1$H-NMR and IR spectrum of this compound was shown below.

$^1$H-NMR (90 MHz, CDCl$_3$)

ϵ:0.93 (3H, t), 1.21 (3H, d), 1.22 (3H, d), 1.20–1.76 (6H, m), 2.74 (1H, br S), 3.20–3.90 (3H, m), 4.10 (1H, m).

IR $\nu^{neat}_{max}$cm$^{-1}$3150–3600.

ii) Esterification 3.20 g of the (2R, 4R)-4-butoxy-2-pentanol produced in the above i) was dissolved in 50 ml of dry tetrahydrofuran. Thereto were added 1.94 g of 1,1,1,3,3,3,-hexamethyldisilazane and one drop of trimethylsilyl chloride, and the mixture was refluxed for 5 hours. The mixture was concentrated and the residue was subjected to distillation under reduced pressure (b.p. 109° C./27 mmHg) to obtain 3.14 g of a trimethylsilyl ether compound.

Separately, 2.23 g of 4-(4'-octyloxy-4-biphenylcarbonyloxy)benzoic acid was mixed with 10 ml of thionyl chloride. The mixture was stirred for 3 hours at 120° C. and then excess thionyl chloride was removed by distillation to obtain a corresponding acid chloride. It was dissolved in 50 ml of dry acetonitrile. Thereto were added 1.16 g of the above obtained trimethylsilyl ether of (2R, 4R)-4-butoxy-2-pentanol and 0.07 g of zinc chloride. The mixture was refluxed for 1 hour. The mixture was concentrated and the residue was subjected to column chromatography (silica gel, developing solvent=dichloromethane) and then to recrystallization from hexane to obtain 1.21 g of the title compound. The $^1$H-NMR, IR spectrum, elementary analysis and specific rotatory power are shown below.

$^1$H-NMR (90 MHz, CDCl$_3$)

δ:0.73-1.00 (6H, m), 1.17 (3H, d), 1.37 (3H, d), 1.10-2.00 (18H, m), 3.07-3.70 (3H, m), 4.00 (2H, t), 5.33 (1H, m), 6.85-8.30 (12H, m).

IR$^{KRb}_{max}$ cm$^{-1}$: 1730, 1710, 1600, 760.

Elementary analysis

Calcd. for C$_{37}$H$_{48}$O$_6$: C,75.48 ; H, 8.22; :C,75.50; H, 8.23 .

$[\alpha]^{28}_D$: $-48.20°$ (c=0.946, chloroform)

The phase transition temperatures and spontaneous polarizations of the title compound and the compounds produced in Examples 92-107 described below are shown in Table 3. These values may vary depending upon the purity of the compounds.

Incidentally, phase transition temperature was determined by using both of DSC and a polarizing microscope with a hot stage, and spontaneous polarization was determined by the triangular wave voltage application method described in the basic version of "Liquid Crystal" co-compiled by Mitsuji Okano and Shunsuke Kobayashi and published by Baifukan in 1985.

In Table 3, K, Sc*, S$_A$, Ch and Iso are the same as defined previously and S denotes an unidentified smectic phase.

EXAMPLE 92

Production of 4'-octyloxy-4-biphenyl ester of 4-[(1R, 3R)-3-butoxy-1-methylbutoxycarbonyl]benzoic acid (a compound of the general formula [I'] in which n is 1, R$_1$ is n-C$_8$H$_{17}$, R$_2$ and R$_3$ are each CH$_3$, R$_4$ is n-C$_4$H$_9$, Q$_1$ and Q$_3$ are each —O—, Q$_2$ is

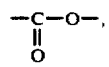

X is a single bond, Y is

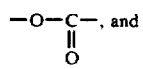

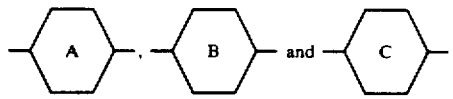

are each

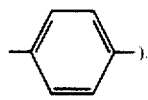

1.16 g of the trimethylsilyl ether derivative of (2R, 4R)-4-butoxy-2-pentanol produced in Example 91 ii) and 2.23 g of 4'-octyloxy-4-biphenyl ester of 4-carboxybenzoic acid were subjected to the same procedure as in Example 91 ii) to obtain 1.13 g of the title compound.

The $^1$H-NMR, IR spectrum, elementary analysis and specific rotatory power of the compound are shown below.

$^1$H-NMR (90 MHz, CDCl$_3$)

δ:0.700-1.00 (6H, m), 1.15 (3H, d), 1.40 (3H, d), 1.05-1.95 (18H, m), 3.06-3.63 (3H, m), 4.00 (2H, t), 5.38 (1H, m), 6.80-8.33 (12H, m).

IR $\nu^{KBr}_{max}$ cm$^{-1}$: 1730, 1715, 1500, 720.

Elementary analysis

Calcd. for C$_{37}$H$_{48}$O$_6$ : C,75.48 ; H, 8.22;

Found : C,75.66 ; H, 8.19.

$[\alpha]^{29}_D$: $-49.99°$ (c=0.932, chloroform)

EXAMPLE 93

Production of 4-[(1S, 3R)-3-butoxy-1-methylbutoxycarbonyl]phenyl ester of 4'-octyloxy-4-biphenylcarboxylic acid (a compound of the general formula [I'] in which n is 1, R$_1$ is n-C$_8$H$_{17}$, R$_2$ and R$_3$ are each CH$_3$, R$_4$ is n-C$_4$H$_9$, Q$_1$ and Q$_3$ are each —O—, Q$_2$ and Y are each

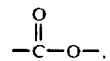

X is a single bond, and

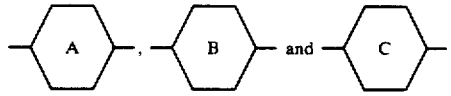

are each

0.40 g of the (2R, 4R)-4-butoxy-2-pentanol produced in Example 91 i), 1.11 g of 4-(4'-octyloxy-4biphenylcarboxylic acid and 0.66 g of triphenylphosphine were dissolved in 30 ml of dry tetrahydrofuran. Thereto was dropwise added 0.44 g of diethyl azodicarboxylate. The mixture was stirred for 30 minutes at room temperature. The solvent was removed by distillation. The residue was subjected to column chromatography (silica gel, developing solvent=chloroform) and then to recrystallization from hexane to obtain 0.72 g of the title compound.

The $^1$H-NMR, IR spectrum, elementary analysis and specific rotation are shown below.

$^1$H-NMR (90 MHz, CDCl$_3$)

δ: 0.73-1.00 (6H, m), 1.18 (3H, d), 1.37 (3H, d), 1.10-2.30 (18H, m), 3.16-3.67 (3H, m), 4.00 (2H, t), 5.30 (1H, m), 6.87-8.30 (12H, m).

IR $\nu^{KBr}_{max}$ cm$^{-1}$: 1735, 1710, 1600, 760.
Elementary analysis
Calcd. for C$_{37}$H$_{48}$O$_6$ C,75.48; H, 8.22;
Found : C,75.66 ; H, 8.29.
$[\alpha]^{26}_D$: +12.21° (c=0.524, chloroform)

EXAMPLE 94

Production of 4'-octyloxy-4-biphenyl ester of 4-[(1S, 3R)-3-butoxy-1-methylbutoxy]benzoic acid (a compound of the general formula [I'] in which n is 1, R$_1$ is n-C$_8$H$_{17}$, R$_2$ and R$_3$ are each CH$_3$, R$_4$ is n-C$_4$H$_9$, Q$_1$, Q$_2$ and Q$_3$ are each —O—, X is a single bond, Y is

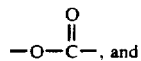, and

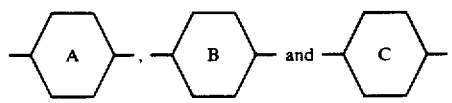

are each

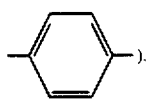).

0.16 g of the (2R, 4R)-4-butoxy-2-pentanol produced in Example 91 i) and 0.21 g of 4'-octyloxy-4biphenyl ester of 4-hydroxybenzoic acid were subjected to the same procedure as in Example 3 to obtain 0.16 g of the title compound.

The $^1$H-NMR, IR spectrum, elementary analysis and specific rotatory power of the compound are shown below.

$^1$H-NMR (90 MHz, CDCl$_3$)

δ: 0.70-1.05 (6H, m), 1.15 (3H, d), 1.40 (3H, d), 1.05-2.30 (18H, m), 3.17-3.70 (3H, m), 4.00 (2H, d), 4.68 (1H, m), 6.80-8.20 (12H, m).

IR $\nu^{KBr}_{max}$ cm$^{-1}$: 1725, 1600, 840, 800, 760.
Elementary analysis
Calcd. for C$_{36}$H$_{48}$O$_5$ : C,77.11 ; H, 8.63;
Found : C,77.34 ; H, 8.66.
$[\alpha]^{28}_D$: +6.77° (c=1.078, chloroform)

EXAMPLE 95

Production of 4-[(1S, 3R)-3-butoxy-1-methylbutoxy]phenyl ester of 4'-octyloxy-4-biphenylcarboxylic acid (a compound of the general formula [I'] in which n is 1, R$_1$ is n-C$_8$H$_{17}$, R$_2$ and R$_3$ are each CH$_3$, R$_4$ is n-C$_4$H$_9$, Q$_1$, Q$_2$ and Q$_3$ are —O—, X is a single bond, Y is

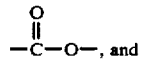, and

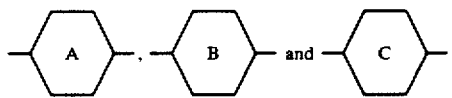

are each

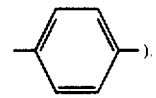).

0.80 g of the (2R, 4R)-4-butoxy-2-pentanol produced in Example 91 i) and 1.05 g of 4-hydroxyphenyl ester of 4'-octyloxy-4-biphenylcarboxylic acid were subjected to the same procedure as in Example 93 to obtain 0.59 g of the title compound.

The $^1$H-NMR, IR spectrum, elementary analysis and specific rotation are shown below.

$^1$H-NMR (90 MHz, CDCl$_3$)

δ: 0.60-1.03 (6H, m), 1.15 (3H, d), 1.35 (3H, d), 1.03-2.30 (18H, m), 3.15-3.70 (3H, m), 4.00 (2H, t), 4.50 (1H, m), 6.70-8.25 (12H, m).

IR $\nu^{KBr}_{max}$ cm$^{-1}$: 1725, 1600, 820, 805, 760.
Elementary analysis
Calcd. for C$_{36}$H$_{48}$O$_5$ : C,77.11 ; H, 8.63;
Found : C,77.18 ; H, 8.67.
$[\alpha]^{28}_D$: +2.23° (c=0.626, chloroform)

EXAMPLE 96

Production of 4'-[(1S, 3R)-3-butoxy-1-methylbutoxy]-4-biphenyl ester of 4-octyloxybenzoic acid (a compound of the general formula [I'] in which n is 1, R$_1$ is n-C$_8$H$_{17}$, R$_2$ and R$_3$ are CH$_3$, R$_4$ is C$_4$H$_9$, Q$_1$, Q$_2$ and Q$_3$ are each —O—, X is

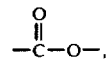,

Y is a single bond, and

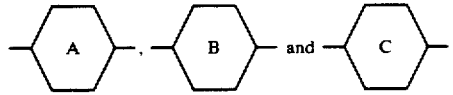

are each

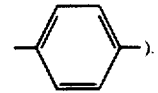).

0.80 g of the (2R, 4R) -4-butoxy-2-pentanol produced in Example 91 i) and 1.05 g of 4'-hydroxy-4-biphenyl ester of 4-octyloxybenzoic acid were subjected to the same procedure as in Example 93 to obtain 0.31 g of the title compound.

The $^1$H-NMR, IR spectrum, elementary analysis and specific rotation of the compound are shown below.

$^1$H-NMR (90 MHz, CDCl$_3$)

δ: 0.73-1.03 (6H, m), 1.15 (3H, d), 1.35 (3H, d), 1.03-2.30 (18H, m), 3.15-3.7 (3H, m), 4.02 (2H , 4.56 (1H, m), 6.75-8.20 (12H, m).

IR $\nu^{KBr}_{max}$ cm$^{-1}$: 1720, 1600, 760.
Elementary analysis
Calcd. for C$_{36}$H$_{48}$O$_5$ : C,77.11 ; H, 8.63;
Found : C,77.31 ; H, 8.70.
$[\alpha]^{29}_D$ : +2.22° (c=0.630, chloroform)

EXAMPLE 97

Production of 4'-octyloxy-4-biphenyl ester of 4-[(1R, 3R)-3-butoxy-1-methylbutoxy]-benzoic acid (a compound of the general formula [I'] in which n is 1, $R_1$ is n-$C_8H_{17}$, $R_2$ and $R_3$ are each $CH_3$, R is n-$C_4H_9$, $Q_1$, $Q_2$ and $Q_3$ are each —O—, X is a single bond, Y is $$-O-\overset{O}{\underset{\|}{C}}-, \text{ and}$$

—⟨A⟩—, —⟨B⟩— and —⟨C⟩— each

—⟨⟩—).

i) Production of (2S, 4R)-4-butoxy-2-pentanol

This optically active alcohol was produced by subjecting the (2R, 4R)-4-butoxy-2-pentanol produced in Example 91 i) to the inversion of hydroxyl group according to the following scheme.

$$\underset{CH_3}{\overset{(R)}{HO-CH}}-CH_2-\underset{CH_3}{\overset{(R)}{CH}}-O-C_4H_9(n) \xrightarrow[\text{EtOOC}-N=N-\text{COOEt}]{\text{Ph}_3P, \text{PhCOOH}}$$

$$\text{Ph}-\overset{O}{\underset{\|}{C}}-O-\underset{CH_3}{\overset{(S)}{CH}}-CH_2-\underset{CH_3}{\overset{(R)}{CH}}-O-C_4H_9(n) \xrightarrow{\text{NaOCH}_3}$$

$$\underset{CH_3}{\overset{(S)}{HO-CH}}-CH_2-\underset{CH_3}{\overset{(R)}{CH}}-O-C_4H_9(n)$$

1.74 g of diethyl azodicarboxylate and 1.22 g of benzoic acid were dissolved in 10 ml of dry ether. Thereto was dropwise added a solution of 1.60 g of (2R, 4R)-4-butoxy-2-pentanol and 2.62 g of triphenylphosphine dissolved in 10 ml of dry ether. The mixture was stirred for 2 days at room temperature.

Ether was removed by distillation under reduced pressure. The residue was subjected to column chromatography (silica gel, developing solvent = chloroform) to obtain 0.82 g of (2S, 4R)-4-butoxy-2-pentyl benzoate.

In 10 ml of methanol were dissolved 0.15 g of sodium hydroxide and 0.82 g of the above obtained (2S, 4R)-4-butoxy-2-pentyl benzoate obtained above. The mixture was stirred overnight at room temperature. Methanol was removed by distillation under reduced pressure. The residue was subjected to column chromatography (silica gel, developing solvent = chloroform) to obtain 0.40 g of (2S, R}-4-butoxy-2pentanol.

The $^1$H-NMR and IR spectrum of this compound are shown below.

$^1$H-NMR (90 MHz, CDCl$_3$)

δ: 0.80-1.03 (3H, m), 1.14 (6H, d), 1.20-1.80 (6H, m), 3.30 (1H, m), 3.45-3.80 (2H, m), 3.90 (1H, br S), 3.95 (1H, m).

IR $\nu^{neat}_{max}$ cm$^{-1}$ : 3150-3650.

ii) Condensation 0.18 g of the (2S, 4R)-4-butoxy-2-pentanol produced in the above i) and 0.21 g of 4'-octyloxy-4biphenyl ester of 4-hydroxybenzoic acid were subjected to the same procedure as in Example 93 to obtain 0.12 g of the title compound. The $^1$H-NMR, IR spectrum, elementary analysis and specific rotatory power are shown below.

$^1$H-NMR (90 MHz, CDCl$_3$)

δ: 0.70-1.05 (6H, m), 1.15 (3H, d), 1.33 (3H, d), 1.05-1.90 (18H, m), 3.15 (1H, m), 3.50 (2H, m), 4.00 (2H, t), 4.80 (1H, m), 6.80-8.20 (12H, m).

IR $\nu^{KBr}_{max}$ cm$^{-1}$ : 1725, 1605, 840, 800, 760.

Elementary analysis

Calcd. for $C_{36}H_{48}O_5$ : C, 77.11 ; H, 8.63;

Found : C, 76.80 ; H, 8.54.

$[\alpha]^{25}_D$: $-31.25°$ (c=0.016, chloroform)

EXAMPLE 98

Production of 4-octyloxyphenyl ester of 4'-[(1S, 3R)-3-butoxy-1-methylbutoxy]-4-biphenylcarboxylic acid (a compound of the general formula [I'] in which n is 1, $R_1$ is n-$C_8H_{17}$, $R_2$ and $R_3$ are each $CH_3$, $R_4$ is n-$C_4H_9$, $Q_1$, $Q_2$ and $Q_3$ are each —O—, X is $$-O-\overset{O}{\underset{\|}{C}}-,$$

Y is a single bond, and

—⟨A⟩—, —⟨B⟩— and —⟨C⟩— are each

—⟨⟩—).

0.40 g of the (2R, 4R)-4-butoxy-2-pentanol produced in Example 91 i) and 0.52 g of 4-octyloxyphenyl ester of 4'-hydroxy-4-biphenylcarboxylic acid were subjected to the same procedure as in Example 93 to obtain 0.44 g of the title compound.

The $^1$H-NMR, IR spectrum, elementary analysis and specific rotatory power of the compound are shown below.

$^1$H-NMR (90 MHz, CDCl$_3$)

δ: 0.75-1.07 (6H, m), 1.18 (3H, d), 1.39 (3H, d), 1.08-2.35 (18H, m), 3.20-3.70 (3H, m), 3.98 (2H, t), 4.63 (1H, m) 6.80-8.30 (12H, m).

IR $\nu^{KBr}_{max}$ cm$^{-1}$ : 1730, 1600, 825, 800, 760.

Elementary analysis

Calcd. for $C_{36}H_{48}O_5$ : C, 77.11 ; H, 8.63;

Found : C, 77.08 ; H, 8.65.

$[\alpha]^{25}_D$: $+3.33°$ (c=0.03, chloroform)

EXAMPLE 99

Production of 4-octyloxyphenyl ester of 4'-[(1S, 3R)-3-ethoxy-1-methylbutoxy]-4-biphenylcarboxylic acid (a compound of the general formula [I'] in which n is 1, R₁ is n-C₈H₁₇, R₂ and R₃ are each CH₃, R₄ is C₂H₅, Q₁, Q₂ and Q₃ are each —O—, X is

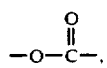

Y is a single bond, and

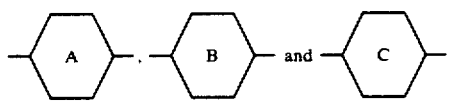

are each

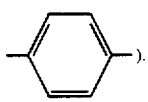

i) Production of (2S, 4R)-4-ethoxy-2-pentanol

This optically active alcohol was produced according to the following scheme.

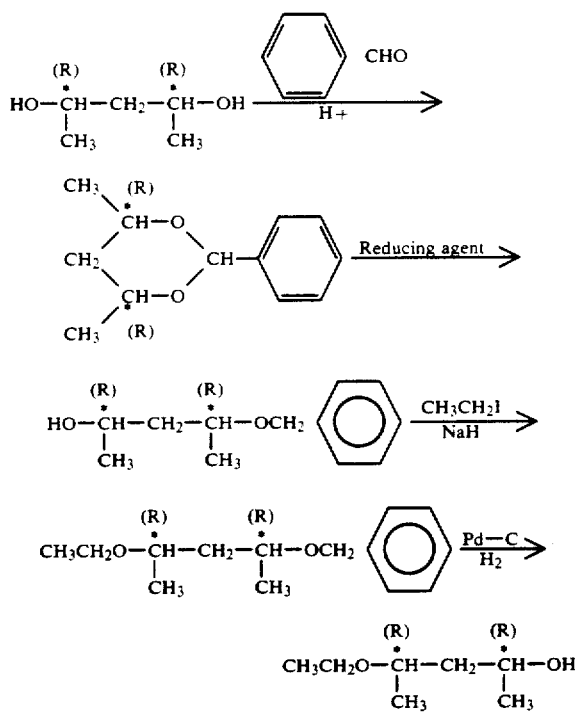

20.0 g of (2R, 4R)-(−)-pentanediol and 20.4 g of benzaldehyde were subjected to the same procedure as in Example 91 i) to obtain 39.9 g of (2R, 4R)-4-benzyloxy-2-pentanol.

In 10 ml of N, N-dimethylformamide were dissolved 2.9 g of the above obtained (2R, 4R)-4-benzyloxy-2-pentanol and 3.0 g of about 60% oily sodium hydride. The mixture was stirred for 2 hours at room temperature. 11.7 g of ethyl iodide was added thereto. The mixture was stirred for 2 hours at room temperature. 100 ml of water and 150 ml of ether were added to the mixture. The ether layer was washed with water, dried and concentrated. The residue was subjected to column chromatography (silica gel, developing solvent=chloroform) to obtain 3.20 g of (2R, 4R)-2-ethoxy-4-benzyloxypentane.

3.20 g of this (2R, 4R)-2-ethoxy-4-benzyloxypentane was dissolved in 50 ml of ethanol. 0.30 g of 0% palladium-carbon and 5 ml of 1 N hydrochloric acid were added, and hydrogenation was carried out at the room temperature at the atmospheric pressure. The catalyst was removed by filtration. The filtrate was concentrated. The residue was subjected to column chromatography (silica gel, developing solvent=chloroform) to obtain 0.91 g of (2R, 4R)-4-ethoxy-2pentanol.

The ¹H-NMR and IR spectrum of the compound are shown below.

¹H-NMR (90 MHz, CDCl₃)
δ: 1.03–1.30 (9H, m),
1.50–1.70 (2H, m),
2.35 (1H, br S),
3.23–4.25 (4H, m).
IR $\nu^{neat}_{max}$ cm⁻¹ : 3150–3600.

ii) Condensation 0.33 g of the (2R, 4R)-4-ethoxy-2-pentanol produced in the above i) and 0.52 g of 4-octyloxyphenyl ester of 4'-hydroxy-4-biphenylcarboxylic acid were subjected to the same procedure as in Example 93 to obtain 0.27 g of the title compound.

The ¹H-MNR, IR spectrum, elementary analysis and specific rotatory power of the compound are shown below.

¹H-NMR (90 MHz, CDCl₃)
δ: 0.70–1.00 (6H, m),
1.00–2.30 (23H, m),
3.30–3.70 (3H, m),
3.97 (2H, t),
4.50–4.80 (1H, m),
6.83–8.30 (12H, m),
IR $\nu^{KBr}_{max}$ cm⁻¹ : 1730, 820, 760.
Elementary analysis
Calcd. for C₃₄H₄₄O₅ : H, 8.33;
Found : C,76.69 ; H, 8.41.
[α]²⁵_D:+2.27° (c=0.264, chloroform)

EXAMPLE 100

Production of 4-octyloxyphenyl ester of 4'-[(1S, 3R)-3-octyloxy-1-methylbutoxy]-4-biphenylcarboxylic acid (a compound of the general formula [I'] in which n is 1, R₁ and R₄ are each n-C₈H₁₇, R₂ and R₃ are each CH₃, Q₁, Q₂ and Q₃ are each —O—, X is

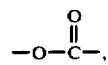

Y is a single bond, and

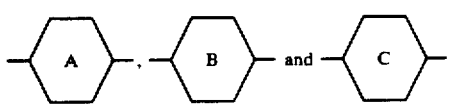

are each

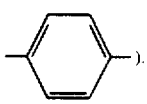

i) Production of (2S, 4R)-4-octyloxy-2-pentanol 5.00 g of (2R, 4R)-(-)-pentanediol and 6.16 g of n-octylaldehyde were subjected to the same procedure as in Example 91 i) to obtain 8.70 g of (2R, 4R)-4-octyloxy-2-pentanol.

ii) Condensation 0.54 g of the (2R, 4R)-4-octyloxy-2-pentanol obtained in the above i) and 0.52 g of 4-octyloxyphenyl ester of 4'-hydroxy-4-biphenylcarboxylic acid were subjected to the same procedure as in Example 93 to obtain 0.49 g of the title compound.

The $^1$H-NMR, IR spectrum, elementary analysis and specific rotatory power of the compound are shown below.

$^1$H-NMR (90 MHz, CDCl$_3$)
δ: 0.75–1.00 (6H, m),
1.15 (3H, d), 1.38 (3H, d),
1.05–2.30 (26H, m),
3.17–3.70 (3H, m),
3.96 (2H, d),
4.35–4.75 (1H, m),
6.80–8.29 (12H, m),
IR $\nu^{KBr}_{max}$ cm$^{-1}$: 1735, 1600, 825, 760.
Elementary analysis
Calcd. for C$_{40}$H$_{56}$O$_5$ : C,77.88 ; H, 9.15;
Found : C,78.02 ; H, 9.27.
$[\alpha]^{25}_D$: +7.92° (c=0.20, chloroform)

EXAMPLE 101

Production of 4-octyloxyphenyl ester of 4'-[(1S, 3R)-3-pentyloxy-1-methylbutoxy]-4-biphenylcarboxylic acid (a compound of the general formula [I'] in which n is 1, R$_1$ is n-C$_8$H$_{17}$, R$_2$ and R$_3$ are each CH$_3$ R$_4$ is n-C$_5$H$_{11}$, Q$_1$, Q$_2$ and Q$_3$ are each —O—, X is

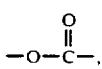

Y is a single bond, and

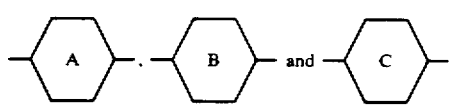

are each

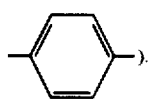

i) Production of (2R, 4R)-4-pentyloxy-2-pentanol 2.90 g of the (2R, 4R)-4-benzyloxy-2-pentanol produced in Example 99 i) and 2.90 g of pentane iodide were subjected to the same procedure as in Example 99 i) to obtain 1.10 g of (2R, 4R)-4-pentyloxy-2-pentanol.

ii) Condensation 0.44 g of the (2R, 4R)-4-pentyloxy-2-pentanol obtained in the above i) and 0.52 g of 4-octyloxyphenyl ester of 4'-hydroxy-4-biphenylcarboxylic acid were subjected to the same procedure as in Example 93 to obtain 0.46 g of the title compound.

The elementary analysis and specific rotatory power of the compound are shown below.

Elementary analysis
Calcd. for C$_{37}$H$_{50}$O$_5$ : C,77.31 ; H, 8.77;
Found : C,77.56 ; H, 8.82.
$[\alpha]^{25}_D$: +4.77° (c=0.31, chloroform)

EXAMPLE 102

Production of 4-propoxyphenyl ester of 4'-[(1S, 3R)-3-octyloxy-1-methylbutoxy]-4-biphenylcarboxylic acid (a compound of the general formula [I'] in which n is 1, R$_1$ is n-C$_3$H$_7$, R$_2$ and R$_3$ are each CH$_3$, R$_4$ is n-C$_8$H$_{17}$, Q$_1$, Q$_2$ and Q$_3$ are each —O—, X is

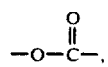

Y is a single bond, and

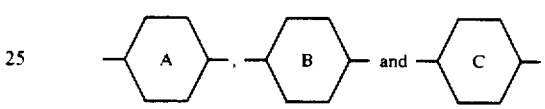

are each

0.54 g of the (2R, 4R)-4-octyloxy-2-pentanol obtained in Example 100 i) and 0.44 g of 4-propoxyphenyl ester of 4'-hydroxy-4-biphenylcarboxylic acid were subjected to the same procedure as in Example 93 to obtain 0.41 g of the title compound.

The elementary analysis and specific rotatory power of the compound are shown below.

Elementary analysis
Calcd. for C$_{35}$H$_{46}$O$_5$ : C,76.89 ; H, 8.48;
Found : C,76.98 ; H, 8.42.
$[\alpha]^{25}_D$: +5.80° (c=0.22, chloroform)

EXAMPLE 103

Production of 4-octylphenyl ester of 4'-[(1S, 3R)-3-butoxy-1-methylbutoxy]-4-biphenylcarboxylic acid (a compound of the general formula [I'] in which n is 1, R$_1$ and R$_4$ are each n-C$_4$H$_9$, R$_2$ and R$_3$ are each CH$_3$, Q$_1$ is a single bond, Q$_2$ and Q$_3$ are each—O—, X is —O—C—, Y is a single bond, and

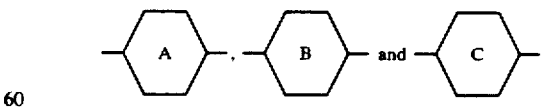

are each

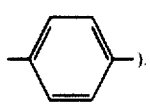

0.40 g of the (2R, 4R)-4-butoxy-2-pentanol produced in Example 91 i) and 0.42 g of 4-octylphenyl ester of 4'-hydroxy-4-biphenylcarboxylic acid were subjected to the same procedure as in Example 93 to obtain the title compound.

The elementary analysis of this compound is shown below.

Elementary analysis

Calcd. for $C_{36}H_{48}O_4$ : C,79.37; H, 8.88;
Found : C,79.47; H, 8.84.

EXAMPLE 104

Production of octyl ester of 4'-[(1S, 3R)-3-octyloxy-1-methylbutoxy]-4-biphenylcarboxylic acid (a compound of the general formula [I'] in which n is 1, $R_1$ and $R_4$ are each n-$C_8H_{17}$, $R_2$ and $R_3$ are each $CH_3$, $Q_1$ is

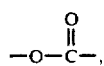

$Q_2$ and $Q_3$ are each —O—, X is a single bond, and

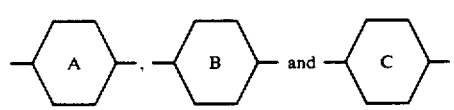

are each

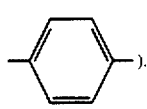

).

0.54 g of the (2R, 4R)-4-octyloxy-2-pentanol obtained in Example 100 i) and 0.41 g of octyl ester of 4'-hydroxy-4-biphenylcarboxylic acid were subjected to the same procedure as in Example 93 to obtain 0.42 g of the title compound.

The elementary analysis of this compound is shown below.

Elementary analysis

Calcd. for $C_{34}H_{52}O_4$: C,77.82 ; H, 9.99;
Found : C,78.15 ; H,10.33.

Example 105

Production of 4-octyloxyphenyl ester of 4-[(1S, 3R)-3-octyloxy-1-methylbutoxy]benzoic acid (a compound of the general formula [I'] in which n is 1, $R_1$ and $R_4$ are each n-$C_8H_{17}$, $R_2$ and $R_3$ are each $CH_3$, $Q_1$, $Q_2$ and $Q_3$ are each—O—, X is

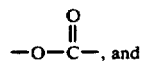

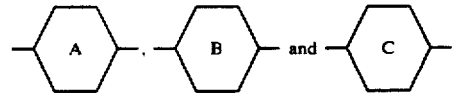

are each

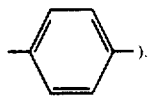

).

0.54 g of the (2R, 4R)-4-octyloxy-2-pentanol obtained in Example 100 i) and 0.43 g of 4-octyloxyphenyl ester of 4-hydroxybenzoic acid were subjected to the same procedure as in Example 93 to obtain 0.52 g of the title compound.

The elementary analysis of this compound is shown below.

Elementary analysis

Calcd. for $C_{35}H_{52}O_4$ : C,75.52 ; H, 9.69;
Found : C,75.68 ; H, 9.84.

EXAMPLE 106

Production of 4-octyloxyphenyl ester of 4'-[(1S, 3R)-3-propoxy-1-methylbutoxy]-4-biphenylcarboxylic acid (a compound of the general formula [I'] in which n is 1, $R_1$ is n-$C_8H_{17}$, $R_2$ and $R_3$ are each $CH_3$, $R_4$ is n-$C_3H_7$, $Q_1$, $Q_2$ and $Q_3$ are each —O—, X is

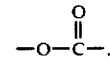

Y is a single bond, and

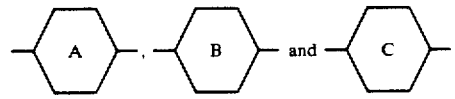

are each

).

i) Production of (2S, 4R)-4-propoxy-2-pentanol 10.0 g of (2R, 4R)-(—)-pentanediol and 7.25 g of propione aldehyde were subjected to the same procedure as in Example 91 i) to obtain 7.44 g of (2R, 4R)-4-propoxy-2-pentanol.

ii) Condensation 0.37 g of the (2R, 4R)-4-propoxy-2-pentanol obtained in the above i) and 0.52 g of 4-octyloxyphenyl ester of 4'-hydroxy-4-biphenylcarboxylic acid were subjected to the same procedure as in Example 93 to obtain 0.45 g of the title compound.

The elementary analysis of this compound is shown below.

Elementary analysis

Calcd. for $C_{35}H_{46}O_5$ : C,76.89 ; H, 8.48;
Found : C,76.97 ; H, 8.53.

EXAMPLE 107

Production of 4-tetradecyloxyphenyl ester of 4'-[(1S, 3R)-3-butoxy-1-methylbutoxy]-4-biphenylcarboxylic acid (a compound of the general formula [I'] in which n is 1, $R_1$ is n-$C_{14}H_{29}$, $R_2$ and $R_3$ are each $CH_3$, $R_4$ is n-$C_4H_9$, $Q_1$, $Q_2$ and $Q_3$ are each—O—, X is

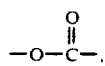

Y is a single bond, and

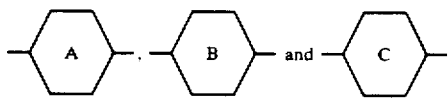

are each

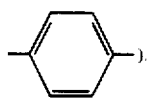

0.40 g of the (2R, 4R)-4-butoxy-2-pentanol obtained in Example 91 i) and 0.63 g of 4-tetradecyloxyphenyl ester of 4'-hydroxy-4-biphenylcarboxylic acid were subjected to the same procedure as in Example 93 to obtain 0.52 g of the title compound.

The elementary analysis of the compound is shown below.

Elementary analysis
Calcd. for $C_{42}H_{60}O_5$: C,78.22 ; H, 9.38;
Found : C,78.39 ; H, 9.44.

The optically active compounds produced in Examples 91-107 were determined for phases, phase transition temperatures and spontaneous polarization. The results of these measurements are shown in Table 3. In Table 3, the arrow mark (←) denotes a phase transition temperature when cooled. The spontaneous polarization is a value at a temperature which is 10° C. lower than the phase transition temperature of $Sc^*$ -$S_A$ (Ch). The other symbols are the same as defined previously.

EXAMPLES 108-114

The compounds of Examples 108-114 were produced in accordance with the previously described processes. Example Nos., structural formulae, phase transition temperatures and elementary analyses of these compounds are shown in Table 3, together with those of the compounds of Examples 91-107. As to the compounds containing a dichiral side chain component whose production has not been explained above (these compounds are given with a * mark in Table 3), the production of component is described in Reference Examples 6-8 which appear after Table 3.

TABLE 3

| Example No. | Structural formula | Phases and Phase transition temperatures (°C.) | Spontaneous Polarization (nC/cm²) |
|---|---|---|---|
| 91 | n-C₈H₁₇O—⟨Ph⟩—⟨Ph⟩—C(=O)O—⟨Ph⟩—C(=O)O—CH(R)(CH₃)—CH₂—CH(OC₄H₉(n))—CH₃ | K ↔68.0↔ Sc* ↔105.4↔ S_A ↔126.4↔ Iso | 52 |
| 92 | n-C₈H₁₇O—⟨Ph⟩—⟨Ph⟩—C(=O)O—⟨Ph⟩—C(=O)O—CH(R)(CH₃)—CH₂—CH(OC₄H₉(n))—CH₃ | K ↔86.0↔ Ch ↔116.6↔ Iso | Not available |
| 93 | n-C₈H₁₇O—⟨Ph⟩—⟨Ph⟩—C(=O)O—⟨Ph⟩—C(=O)O—CH(S)(CH₃)—CH₂—CH(OC₄H₉(n))—CH₃ | K ↔71.0↔ Sc* ↔107.8↔ S_A ↔137.0↔ Iso | 54 |
| 94 | n-C₈H₁₇O—⟨Ph⟩—⟨Ph⟩—C(=O)O—⟨Ph⟩—O—CH(S)(CH₃)—CH₂—CH(OC₄H₉(n))—CH₃ | K ↔62.4↔ S_A ↔64.0↔ Iso | Not available |
| 95 | n-C₈H₁₇O—⟨Ph⟩—⟨Ph⟩—C(=O)O—⟨Ph⟩—O—CH(S)(CH₃)—CH₂—CH(OC₄H₉(n))—CH₃ | K ↔72.0↔ Sc* ↔87.0↔ S_A ↔111.8↔ Iso | 34 |
| 96 | n-C₈H₁₇O—⟨Ph⟩—⟨Ph⟩—⟨Ph⟩—O—CH(S)(CH₃)—CH₂—CH(OC₄H₉(n))—CH₃ | K ↔55.0↔ S_A ↔78.0↔ Iso | Not available |
| 97 | n-C₈H₁₇O—⟨Ph⟩—⟨Ph⟩—C(=O)O—⟨Ph⟩—O—CH(R)(CH₃)—CH₂—CH(OC₄H₉(n))—CH₃ | K ↔65.1↔ Ch ↔80.6↔ Iso | Not available |
| 98 | n-C₈H₁₇O—⟨Ph⟩—⟨Ph⟩—O—C(=O)—⟨Ph⟩—O—CH(S)(CH₃)—CH₂—CH(OC₄H₉(n))—CH₃ | K ↔62.0↔ Iso ↔56.0↔ Sc* | 93 |

TABLE 3-continued

| # | Structure | Phase transitions | Value |
|---|---|---|---|
| 99 | n-C$_8$H$_{17}$O–⟨Ph⟩–C(=O)O–⟨Ph⟩–⟨Ph⟩–O–(S)CH(CH$_3$)–CH$_2$–(R)CH(CH$_3$)–OC$_2$H$_5$ | K $\xleftrightarrow{52.6}$ Sc* $\xleftrightarrow{54.3}$ Ch $\xleftrightarrow{69.6}$ Iso | 74 |
| 100 | n-C$_8$H$_{17}$O–⟨Ph⟩–C(=O)O–⟨Ph⟩–⟨Ph⟩–O–(S)CH(CH$_3$)–CH$_2$–(R)CH(CH$_3$)–OC$_8$H$_{17}$(n) | K $\xleftrightarrow{12.3}$ Sc* $\xleftrightarrow{43.0}$ Ch $\xleftrightarrow{50.6}$ Iso | 48 |
| 101 | n-C$_8$H$_{17}$O–⟨Ph⟩–C(=O)O–⟨Ph⟩–⟨Ph⟩–O–(S)CH(CH$_3$)–CH$_2$–(R)CH(CH$_3$)–OC$_5$H$_{11}$(n) | K $\xleftrightarrow{50.2}$ Ch $\xleftrightarrow{56.4}$ Iso; Sc* at 50.0 | 95 |
| 102 | n-C$_8$H$_{17}$O–⟨Ph⟩–C(=O)O–⟨Ph⟩–⟨Ph⟩–O–(S)CH(CH$_3$)–CH$_2$–(R)CH(CH$_3$)–OC$_8$H$_{17}$(n) | K $\xleftrightarrow{48.9}$ Iso | Not available |
| 103 | n-C$_8$H$_{17}$O–⟨Ph⟩–C(=O)O–⟨Ph⟩–⟨Ph⟩–O–(S)CH(CH$_3$)–CH$_2$–(R)CH(CH$_3$)–OC$_4$H$_9$(n) | K $\xleftrightarrow{41.9}$ Iso | Not available |
| 104 | n-C$_8$H$_{17}$O–⟨Ph⟩–C(=O)O–⟨Ph⟩–⟨Ph⟩–⟨Ph⟩–O–(S)CH(CH$_3$)–CH$_2$–(R)CH(CH$_3$)–OC$_8$H$_{17}$(n) | K $\xleftrightarrow{-3.9}$ Iso | Not available |
| 105 | n-C$_8$H$_{17}$O–⟨Ph⟩–C(=O)O–⟨Ph⟩–⟨Ph⟩–O–(R)CH(CH$_3$)–CH$_2$–(R)CH(CH$_3$)–OC$_8$H$_{17}$(n) | K $\xleftrightarrow{-3.9}$ Iso | Not available |
| 106 | n-C$_8$H$_{17}$O–⟨Ph⟩–C(=O)O–⟨Ph⟩–⟨Ph⟩–O–(S)CH(CH$_3$)–CH$_2$–(R)CH(CH$_3$)–OC$_3$H$_7$(n) | K $\xleftrightarrow{62.6}$ Ch $\xleftrightarrow{64.5}$ Iso; Sc* at 57.5 | Not available |

TABLE 3-continued

| Example No. | Structural formula | Phases and Phase transition temperatures (°C.) | Spontaneous polarization (nC/cm²) | Elemental analysis (Compositional formula, calculated value observed value) |
|---|---|---|---|---|
| 107 | n-C₁₄H₂₉O—〈phenyl〉—COO—〈phenyl〉—O—CH(S)(CH₃)—CH₂—CH(R)(CH₃)—OBu(n) | K ⇌(64.1)(61.9) Ch ⇌(66.2) Iso; Sc* | 50(46°C.) | C₃₆H₄₆O₆: C, 75.23; H, 8.07 : C, 75.38; H, 8.10 |
| 108 | n-C₈H₁₇O—〈phenyl〉—COO—〈phenyl〉—O—CH(S)(CH₃)—CH₂—CH(R)(CH₃)—O—C(=O)—Pr(*1) | K ⇌(51.8)(56.7) Sc* ⇌(75.5) Ch ⇌(75.5) Iso | Not available | C₃₆H₄₆O₆: C, 75.23; H, 8.07 : C, 75.44; H, 8.15 |
| 109 | n-C₈H₁₇O—〈phenyl〉—COO—〈phenyl〉—O—CH(S)(CH₃)—CH₂—CH(R)(CH₃)—O—C(=O)—Pr(*2) | K ⇌(-5.9)(38.3) Sc* ⇌(29.4) Ch ⇌(79.0) Iso | 74 | C₃₆H₅₀O₄: C, 79.08; H, 9.22 : C, 78.77; H, 9.16 |
| 110 | n-C₈H₁₇O—〈phenyl〉—COO—〈phenyl〉—CH₂O—CH(S)(CH₃)—CH₂—CH(R)(CH₃)—OBu(n) | K ⇌(35.2)(50.3) Sc* ⇌(75.7) Iso | 60 | C₃₆H₅₀O₄: C, 79.08; H, 9.22 : C, 78.94; H, 9.30 |
| 111 | n-C₈H₁₇O—〈phenyl〉—〈phenyl〉—O—CH₂—〈phenyl〉—O—CH(S)(CH₃)—CH₂—CH(R)(CH₃)—OBu(n) | K ⇌(43.1)(57.9) Sc* ⇌(69.4) SA ⇌(74.7) Iso | Not available | C₂₉H₄₂O₄: C, 76.61; H, 9.31 : C, 76.71; H, 9.36 |
| 112 | n-C₈H₁₇O—〈phenyl〉—〈phenyl〉—O—C(=O)—CH(R)(CH₃)—CH₂—CH(S)(CH₃)—OC₃H₇(*1) | K ⇌(25.0) Iso | Not available | C₂₈H₄₀O₄: C, 76.33; H, 9.15 : C, 76.16; H, 9.00 |
| 113 | n-C₈H₁₇O—〈phenyl〉—〈phenyl〉—O—C(=O)—CH(S)(CH₃)—CH₂—CH(R)(CH₃)—OEt(*3) | K ⇌(5.1)(18.7) S1 ⇌(7.0) Iso | Not available | C₂₉H₄₂O₅; C, 74.33; H, 8.60 : C, 74.26; H, 8.75 |
| 114 | n-C₈H₁₇C(=O)O—〈phenyl〉—〈phenyl〉—O—C(=O)—CH(S)—CH₂—CH(R)(CH₃)—OEt(*3) | K ⇌(7.3) Iso | Not available | C₂₉H₄₂O₅; C, 74.33; H, 8.60 : C, 74.26; H, 8.75 |

(*1) See Reference Example 6.
(*2) See Reference Example 7.
(*3) See Reference Example 3.

Production of the novel dichiral compounds used in the above Examples is explained in the following Reference Examples.

REFERENCE EXAMPLE 6

Production of (1R, 3R)-3-hydroxy-1-methylbutyl ester of butyric acid

The (2R, 4R)-4-benzyloxy-2-pentanol obtained in Example 99 (a starting material) was subjected to the following scheme to obtain the title compound as a colorless oil.

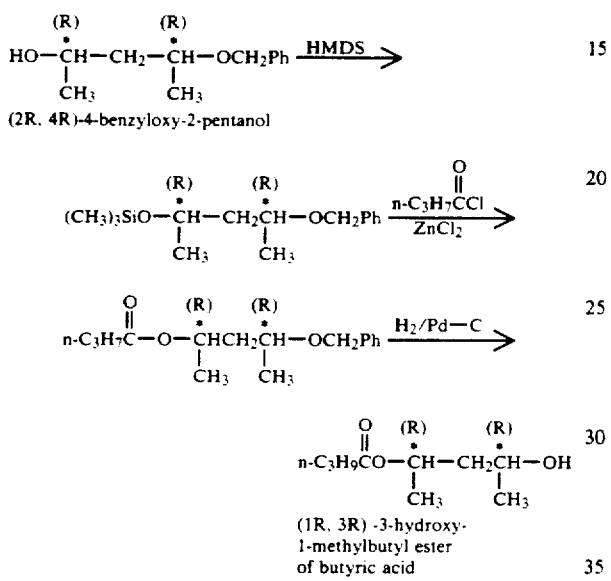

REFERENCE EXAMPLE

Production of (1S, 3R)-3-hydroxy-1-methylbutyl ester of butyric acid

The (2R, 4R)-4-benzyloxy-2-pentanol obtained in Example 99 (a starting material) was subjected to the following scheme to obtain the title compound as a colorless oil.

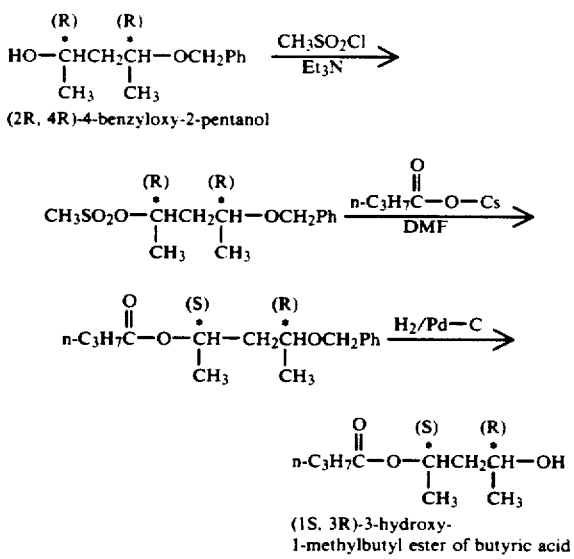

REFERENCE EXAMPLE 8

Production of (2S, 4R)-4-ethoxy-2-methylpentanoic acid

The (2R, 4R)-4-ethoxy-2-pentanol obtained in Example 99 (a starting material) was subjected to the following scheme to obtain the title compound as a colorless oil.

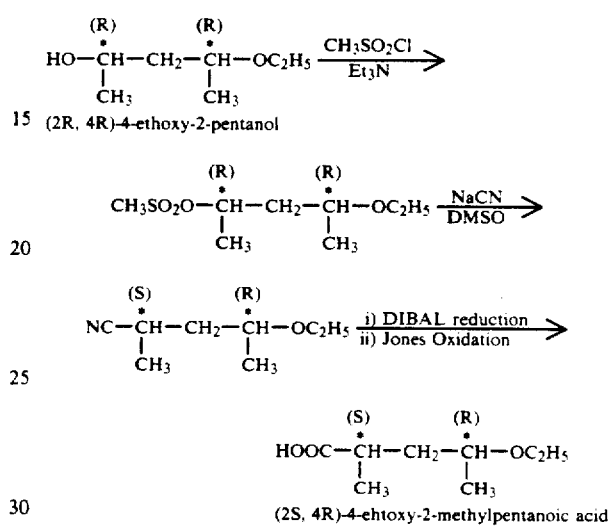

APPLICATION EXAMPLE 1

The optically active compounds of the present invention shown in Table 4 were incorporated into the conventionally known ferroelectric liquid crystal compositions (hereinafter referred to as "the mother liquid crystal(s)") shown in Table 5, to obtain liquid crystal compositions containing the optically active compounds of the present invention.

Each composition and each mother liquid crystal were measured for spontaneous polarization, and the results are shown in Table 4.

Each spontaneous polarization shown in Table 4 is a value at a temperature which is 10° C. lower than the upper limit of chiral smectic C phase, and was measured according to the Sowyer-Tower method described in Japanese Journal of Applied Physics, 24, 1389-1393 (1985).

TABLE 4

| Mother liquid crystal | Optically active compound [I] of present invention | | Spontaneous Polarization (nC/cm$^2$) |
|---|---|---|---|
| | Example No. | Addition amount (wt. %) | |
| A | — | — | 4 |
| A | 9 | 20 | 8.5 |
| A | 6 | 10 | 9 |
| A | 14 | 10 | 10 |
| A | 18 | 20 | 12.5 |
| B | — | — | 1 |
| B | 13 | 20 | 10 |
| C | — | — | <1 |
| C | 18 | 10 | 7 |
| C | 13 | 20 | 11 |

TABLE 5

| Mother liquid crystal | Structural formula |
|---|---|
| A | $C_8H_{17}O$—⟨⟩—CH=N—⟨⟩—$CO_2CH_2\overset{*}{C}HC_2H_5$ |
|   | $\qquad\qquad\qquad\qquad\qquad\qquad\qquad$ $CH_3$ |
|   | $C_8H_{17}O$—⟨⟩—⟨⟩—$CO_2CH_2\overset{*}{C}HC_2H_5$ |
|   | $\qquad\qquad\qquad\qquad\qquad\qquad\qquad$ $CH_3$ |
|   | (Equimolar mixture) |
| B | $C_{10}H_{21}O$—⟨⟩—$CO_2$—⟨⟩—$OCH_2\overset{*}{C}HC_2H_5$ |
|   | $\qquad\qquad\qquad\qquad\qquad\qquad\qquad$ $CH_3$ |
| C | $C_7H_{15}O$—⟨⟩—OCO—⟨⟩—$O(CH_2)_3\overset{*}{C}HC_2H_5$ |
|   | $\qquad\qquad\qquad\qquad\qquad\qquad\qquad$ $CH_3$ |
|   | $C_7H_{15}O$—⟨⟩—OCO—⟨⟩—$O(CH_2)_5\overset{*}{C}HC_2H_5$ |
|   | $\qquad\qquad\qquad\qquad\qquad\qquad\qquad$ $CH_3$ |
|   | (Equimolar mixture) |

As is clear from Table 4, the incorporation of optically active compounds of the present invention into conventionally known ferroelectric liquid crystal compounds (or mixtures) significantly increased the spontaneous polarization of said liquid crystal compounds (or mixtures).

Liquid crystal devices were prepared by sealing each composition shown in the upper column of Table 4 in a cell constituted by (a) an ITO glass obtained by spin coating of a polyimide and subsequent rubbing and (b) a spacer consisting of a polyethylene terephthalate film of 6 mm in thickness. A rectangular wave (40 Vp-p) was applied to the liquid crystal devices at room temperature, and observation by a polarizing microscope was made. A clear optical contrast was observed. Similar observation was made to a liquid crystal device using the mother liquid crystal C alone, but no optical contrast was observed.

As is clear from the above, optical modulators such as display, printer head and the like can be produced by using a liquid crystal composition containing the optically active compound of the present invention.

APPLICATION EXAMPLE 2

The optically active compounds of the present invention shown in Table 6 were incorporated into a mother liquid crystal shown below, and the resulting compositions were measured for spontaneous polarization. The results are shown in Table 6. Incidentally, the spontaneous polarization is a value at a temperature which is 10° C. lower than the upper limit of Sc* phase.

TABLE 6

| Mother liquid crystal | Optically active compound [I] of present invention | | Spontaneous Polarization ($nC/cm^2$) |
|---|---|---|---|
|   | Example No. | Addition amount (wt. %) |   |
| A | 1 | 10 | 7 |
| A | 3 | 20 | 11 |
| A | 5 | 30 | 15 |
| A | 8 | 10 | 10 |
| A | 8 | 30 | 31 |
| A | 10 | 20 | 10 |
| A | — | — | <1 |

Mother liquid crystal A

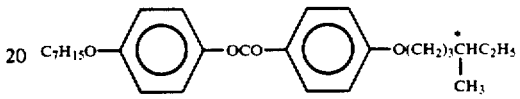

$C_7H_{15}O$—⟨⟩—OCO—⟨⟩—$O(CH_2)_3\overset{*}{C}HC_2H_5$ $\quad CH_3$

Liquid crystal devices were prepared by sealing each composition shown in the upper column of Table 6 in a cell constituted by (a) a glass with transparent electrodes obtained by spin coating of a polyimide and subsequent rubbing and (b) a spacer consisting of a polyethylene terephthalate film of 6 μm in thickness. A rectangular wave (40 Vp-p, 10 Hz) was applied to the liquid crystal devices, and observation by a polarizing microscope was made. An optical response was observed. Similar observation was made to a liquid crystal device using the mother liquid crystal A, but no optical response was obtained even by the application of a higher voltage of 50 Vp-p.

EXAMPLES OF COMPOSITION PREPARATION

The following liquid compositions were prepared using the compound of Example 1 or the compound of Example 91. Using these compositions, liquid crystal devices as shown in FIG. 1 were prepared. All of these devices showed a good optical response when a rectangular wave (40 Vp-p, 10 Hz) was applied at room temperature. Further, each composition was mixed with 3% by weight of an anthraquinone type or azo type dichroic dye, and guest host type liquid crystal devices were prepared in the same manner as above. All of these devices showed a good optical response of guest host type. Thus, it was found that the compound of the present invention is useful as a component of liquid crystal composition.

| Component | Amount (mole %) |
|---|---|
| Liquid crystal composition 1 |   |
| $C_8H_{17}O$—⟨⟩—CH=N—⟨⟩—$CO_2CH_2\overset{*}{C}HC_2H_5$ $\ CH_3$ | 18 |
| $C_8H_{17}O$—⟨⟩—⟨⟩—$CO_2CH_2\overset{*}{C}HC_2H_5$ $\ CH_3$ | 20 |

-continued

| Component | Amount (mole %) |
|---|---|
| 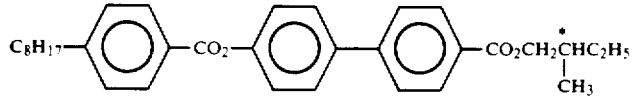 $C_8H_{17}$—〇—$CO_2$—〇—〇—$CO_2CH_2\overset{*}{C}HC_2H_5$ / $CH_3$ | 26 |
| 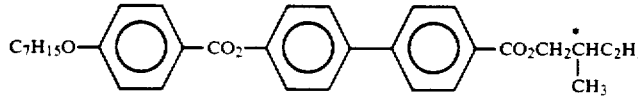 $C_7H_{15}O$—〇—$CO_2$—〇—〇—$CO_2CH_2\overset{*}{C}HC_2H_5$ / $CH_3$ | 27 |
| Compound of Example 1 | 9 |
| Liquid crystal composition 2 | |
| 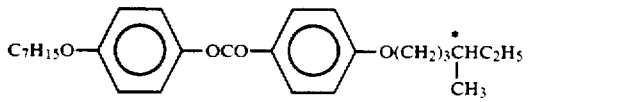 $C_7H_{15}O$—〇—OCO—〇—$O(CH_2)_3\overset{*}{C}HC_2H_5$ / $CH_3$ | 32 |
| 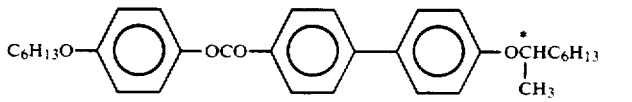 $C_6H_{13}O$—〇—OCO—〇—〇—$O\overset{*}{C}HC_6H_{13}$ / $CH_3$ | 33 |
| 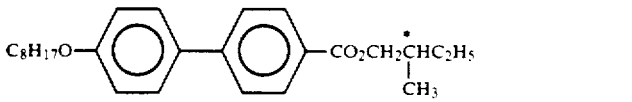 $C_8H_{17}O$—〇—〇—$CO_2CH_2\overset{*}{C}HC_2H_5$ / $CH_3$ | 15 |
| Composition of Example 91 | 20 |
| Liquid crystal composition 3 | |
| 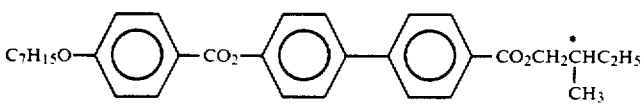 $C_7H_{15}O$—〇—$CO_2$—〇—〇—$CO_2CH_2\overset{*}{C}HC_2H_5$ / $CH_3$ | 15 |
| Compound of Example 1 | 25 |
| 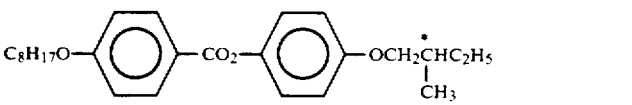 $C_8H_{17}O$—〇—$CO_2$—〇—$OCH_2\overset{*}{C}HC_2H_5$ / $CH_3$ | 35 |
| 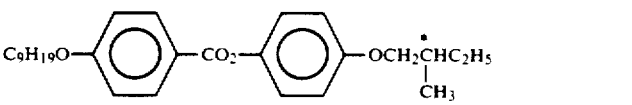 $C_9H_{19}O$—〇—$CO_2$—〇—$OCH_2\overset{*}{C}HC_2H_5$ / $CH_3$ | 25 |
| Liquid crystal composition 4 | |
| 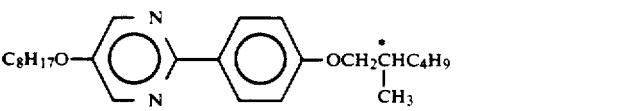 $C_8H_{17}O$—(pyrazine)—〇—$OCH_2\overset{*}{C}HC_4H_9$ / $CH_3$ | 30 |
| 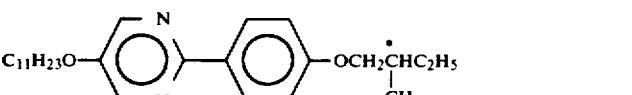 $C_{11}H_{23}O$—(pyrazine)—〇—$OCH_2\overset{*}{C}HC_2H_5$ / $CH_3$ | 30 |
| 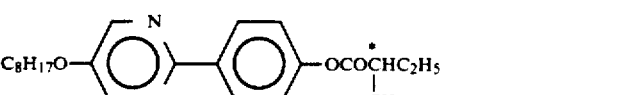 $C_8H_{17}O$—(pyrazine)—〇—$OCO\overset{*}{C}HC_2H_5$ / $CH_3$ | 30 |
| Compound of Example 91 | 10 |

As described in the above Examples and Application Examples, the present invention can provide ferroelectric liquid crystal compounds which have a spontaneous polarization of at least 30 nC/cm² and are stable physically and chemically. Further, the use of these liquid crystal compounds as a component of liquid crystal composition can provide a liquid crystal composition with very high spontaneous polarization.

What is claimed is:

1. An optically active compound exhibiting a spontaneous polarization and represented by the general formula:

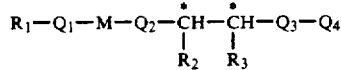

wherein $R_1$ is an alkyl group of 3-14 carbon atoms, $R_2$ and $R_3$ are each a lower alkyl group of 1-3 carbon atoms, $R_4$ is an alkyl group of 1-10 carbon atoms, $Q_1$ is a single bond or an ether bond and $Q_2$ and $Q_3$ ar each an ether bond or a carboxylic acid ester bond, M is,

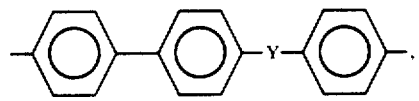

or

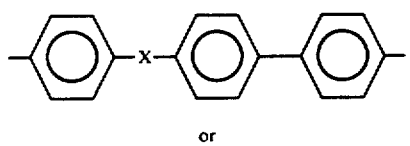

in which X and Y are each a carboxylic acid ester bond and *-marked carbon atoms are each as asymmetric carbon atom.

2. The optically active compound according to claim 1, wherein $R_1$ and $R_4$ are each a straight alkyl chain, $R_2$ and $R_3$ are each a straight alkyl chain, $Q_1$, $Q_2$ and $Q_3$ are each an ether bond, and M is

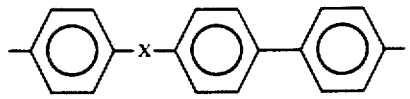

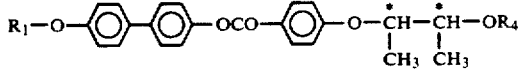

where X is a carboxylic acid ester bond, Y is a single bond.

3. The optically active compound according to claim 1, which is represented by the general formula:

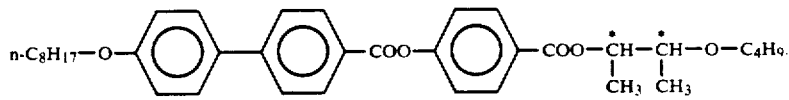

wherein $R_1$ is an alkyl group of 3-14 carbon atoms and $R_4$ is an alkyl group of 1-10 carbon atoms.

4. The optically active compound according to claim 1, which is represented by the formula:

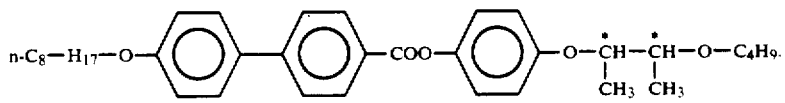

5. The optically active compound according to claim 1, which is represented by the formula:

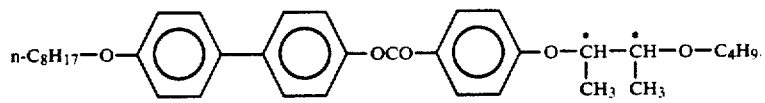

6. The optically active compound according to claim 1, which is represented by the formula:

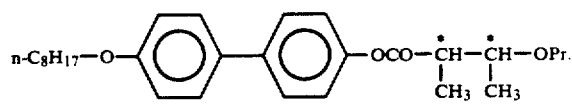

7. The optically active compound according to claim 1, which is represented by the formula:

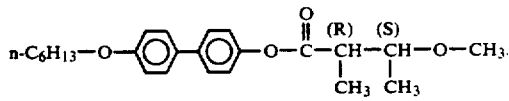

8. A liquid crystal optical device comprising a cell, a spacer and a liquid crystal composition containing at least one compound of claim 1 being sealed in said cell.

9. An optically active compound according to claim 1, which is represented by the formula:

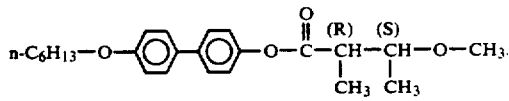

10. An optically active compound according to claim 1, which is represented by the formula:

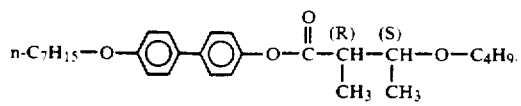

11. An optically active compound according to claim 1, which is represented by the formula:

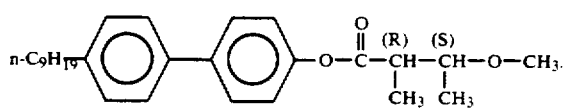

12. An optically active compound according to claim 1, which is represented by the formula:

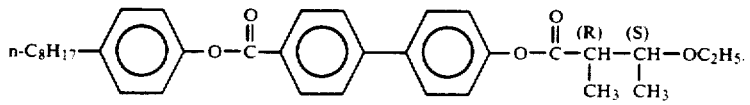

13. An optically active compound exhibiting a spontaneous polarization and represented by the following formula:

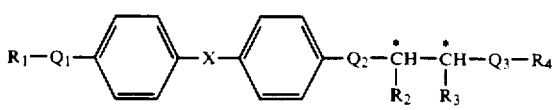

wherein X is a single bond, $R_1$ is an alkyl group of 3-14 carbon atoms, $R_2$ and $R_3$ are independently a lower alkyl group of 1-3 carbon atoms, $R_4$ is an alkyl group of 1-10 carbon atoms, $Q_1$ is a single bond or an ether bond, $Q_2$ and $Q_3$ are each an ether bond or a carboxylic acid and *-marked carbon atoms are each an asymmetrical carbon atom.

* * * * *

UNITED STATES PATENT AND TRADEMARK OFFICE
CERTIFICATE OF CORRECTION

PATENT NO. : 5,167,863
DATED : December 1, 1992
INVENTOR(S) : T. KITAMURA, et al.

It is certified that error appears in the above-identified patent and that said Letters Patent is hereby corrected as shown below:

In column 106, the last two lines of the text in claim 2 should read "where X is a carboxylic acid ester bond".

Signed and Sealed this

Twenty-sixth Day of September, 1995

*Attest:*

BRUCE LEHMAN

*Attesting Officer*     *Commissioner of Patents and Trademarks*